(12) United States Patent
Paster et al.

(10) Patent No.: US 11,357,548 B2
(45) Date of Patent: *Jun. 14, 2022

(54) ROBOTIC ROD BENDERS AND RELATED MECHANICAL AND MOTOR HOUSINGS

(71) Applicant: GLOBUS MEDICAL, INC., Audubon, PA (US)

(72) Inventors: Samuel Paster, North Kingstown, RI (US); Norbert Johnson, North Andover, MA (US); Olivier Chappuis, Lutry (CH); David Cleary, Somerville, MA (US); Sritam Parashar Rout, Dracut, MA (US); Michael Brauckmann, Woburn, MA (US); Kyle VanLeer, Jeffersonville, PA (US)

(73) Assignee: Globus Medical, Inc., Audubon, PA (US)

(*) Notice: Subject to any disclaimer, the term of this patent is extended or adjusted under 35 U.S.C. 154(b) by 359 days.

This patent is subject to a terminal disclaimer.

(21) Appl. No.: 16/560,422

(22) Filed: Sep. 4, 2019

(65) Prior Publication Data

US 2020/0015858 A1 Jan. 16, 2020

Related U.S. Application Data

(63) Continuation-in-part of application No. 16/183,980, filed on Nov. 8, 2018, now Pat. No. 10,898,252.
(Continued)

(51) Int. Cl.
*A61B 17/70* (2006.01)
*A61B 34/10* (2016.01)
(Continued)

(52) U.S. Cl.
CPC .......... *A61B 17/7013* (2013.01); *A61B 34/10* (2016.02); *B21C 51/00* (2013.01);
(Continued)

(58) Field of Classification Search
CPC ................ A61B 17/7013; A61B 34/10; A61B 2034/104; A61B 2034/105;
(Continued)

(56) References Cited

U.S. PATENT DOCUMENTS

| 1,068,626 A | | 7/1913 | Buck | |
|---|---|---|---|---|
| 2,306,223 A | * | 12/1942 | Parker | B21D 7/12 72/1 |

(Continued)

FOREIGN PATENT DOCUMENTS

| EP | 3461444 A1 | 4/2009 |
|---|---|---|
| EP | 3344175 A1 | 7/2018 |

(Continued)

OTHER PUBLICATIONS

US 8,231,638 B2, 07/2012, Swarup et al. (withdrawn)

*Primary Examiner* — Eduardo C Robert
*Assistant Examiner* — David C Comstock

(57) ABSTRACT

Robotic rod benders are disclosed including a motor housing and a mechanical housing coupled with the motor housing. The motor housing may include first and second rod feeding/rotating motors, a brake motor, a bending motor, first and second rod feeding/rotating transmission inputs, a brake transmission input, and a bending transmission input. The mechanical housing may include a rod feeding/rotating subassembly, a brake subassembly, a bending subassembly, first and second rod feeding/rotating transmission outputs, a brake transmission output, and a bending transmission output. Separate motor and mechanical housings are also disclosed.

20 Claims, 50 Drawing Sheets

Related U.S. Application Data

(60) Provisional application No. 62/583,851, filed on Nov. 9, 2017.

(51) Int. Cl.
  *B21C 51/00* (2006.01)
  *B21D 7/06* (2006.01)
  *A61B 17/00* (2006.01)

(52) U.S. Cl.
  CPC .... *B21D 7/066* (2013.01); *A61B 2017/00199* (2013.01); *A61B 2017/00212* (2013.01); *A61B 2017/00398* (2013.01); *A61B 2034/104* (2016.02); *A61B 2034/105* (2016.02); *A61B 2034/108* (2016.02)

(58) Field of Classification Search
  CPC .... A61B 2034/108; A61B 2017/00199; A61B 2017/00212; A61B 2017/00398; B21C 51/00; B21D 7/066
  USPC .......................... 606/261, 262; 72/129, 169
  See application file for complete search history.

(56) References Cited

U.S. PATENT DOCUMENTS

| | | |
|---|---|---|
| 4,150,293 A | 4/1979 | Franke |
| 4,737,038 A | 4/1988 | Dostoomian |
| 4,757,710 A | 7/1988 | Haynes |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |

(56) References Cited

U.S. PATENT DOCUMENTS

| | | |
|---|---|---|
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |

(56) References Cited

U.S. PATENT DOCUMENTS

| | | | |
|---|---|---|---|
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,556,807 B2 | 8/2013 | Scott et al. |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,005,113 B2 | 4/2015 | Scott et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,271,633 B2 | 3/2016 | Scott et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |

(56) References Cited

U.S. PATENT DOCUMENTS

| | | |
|---|---|---|
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,565,997 B2 | 2/2017 | Scott et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 9,962,069 B2 | 5/2018 | Scott et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0262911 A1* | 12/2005 | Dankowicz .......... B21D 7/14 72/31.04 |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |

(56) References Cited

U.S. PATENT DOCUMENTS

| | | |
|---|---|---|
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0311203 A1* | 10/2014 | Crawford .............. B21F 45/008 72/129 |
| 2014/0316420 A1 | 10/2014 | Ballard et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0135793 A1 | 5/2015 | Plummer et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0263646 A1 | 9/2016 | Shazly et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0056086 A1* | 3/2017 | Kostrzewski ............ B21D 7/02 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0228351 A1 | 8/2018 | Scott et al. |
| 2018/0289396 A1* | 10/2018 | McGahan .............. A61B 34/37 |
| 2018/0289408 A1* | 10/2018 | McGahan .......... A61B 17/7011 |
| 2018/0289491 A1 | 10/2018 | McGahan et al. |
| 2019/0336179 A1* | 11/2019 | Pak .................... A61B 17/7074 |
| 2020/0015858 A1 | 1/2020 | Paster et al. |

FOREIGN PATENT DOCUMENTS

| | | |
|---|---|---|
| JP | 2004-9125 A | 1/2004 |
| JP | 2010-162557 A | 7/2010 |
| JP | 2016536051 A | 11/2016 |
| WO | 2013085982 A2 | 6/2013 |
| WO | 2015195843 A2 | 12/2015 |
| WO | WO-2016088130 A1 * | 6/2016 .............. A61B 34/10 |
| WO | 2017221257 A1 | 12/2017 |

\* cited by examiner

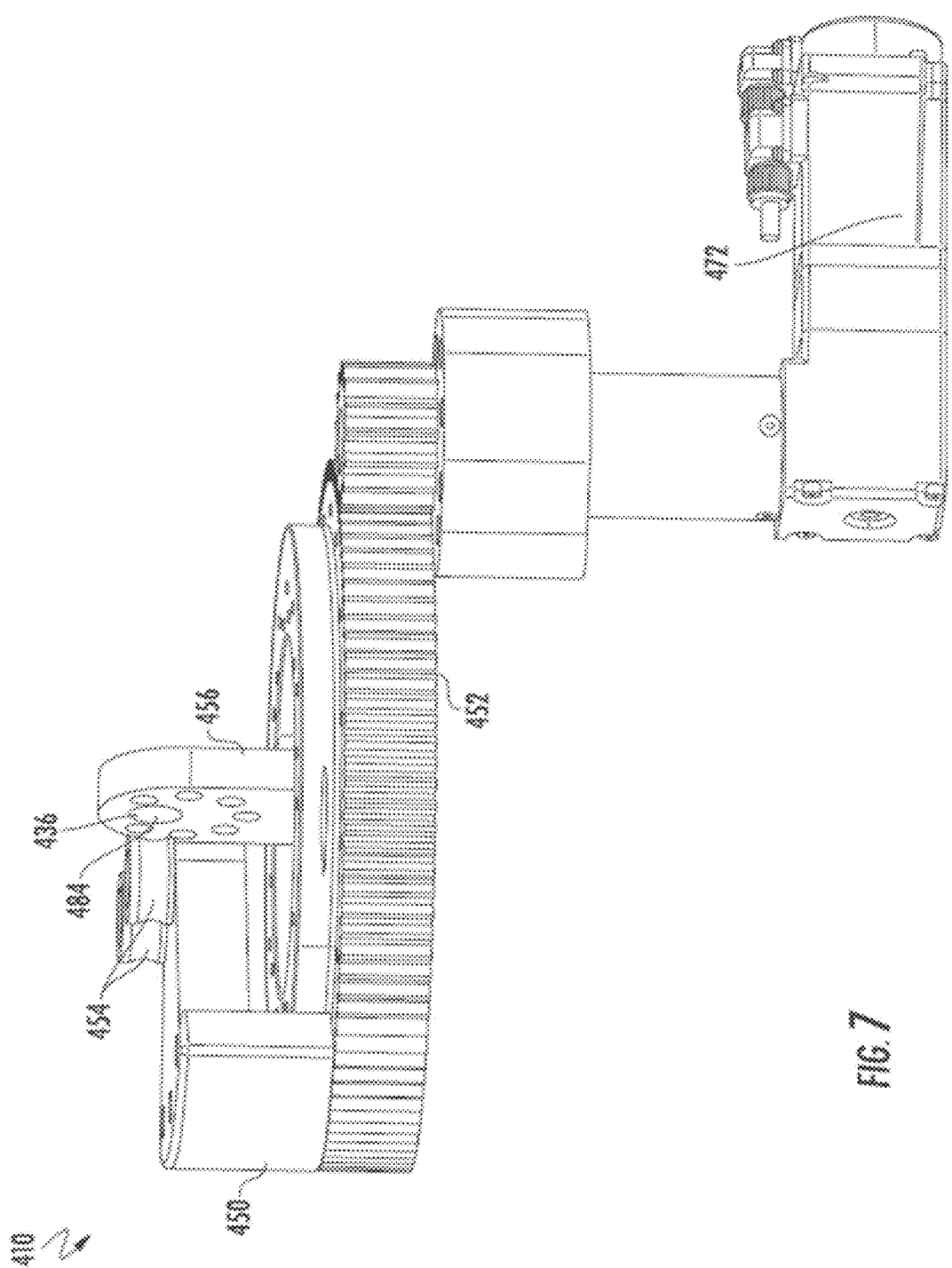

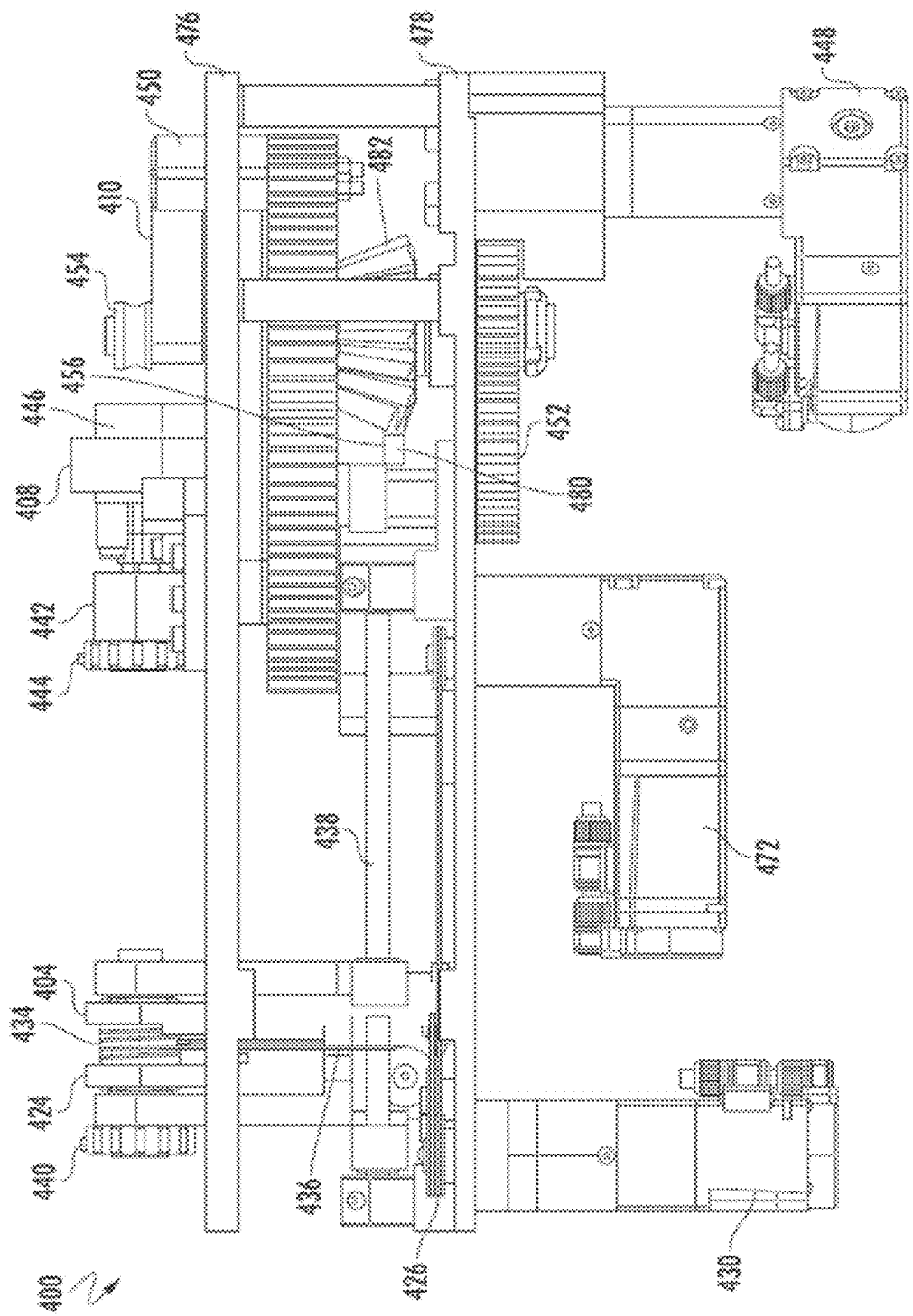

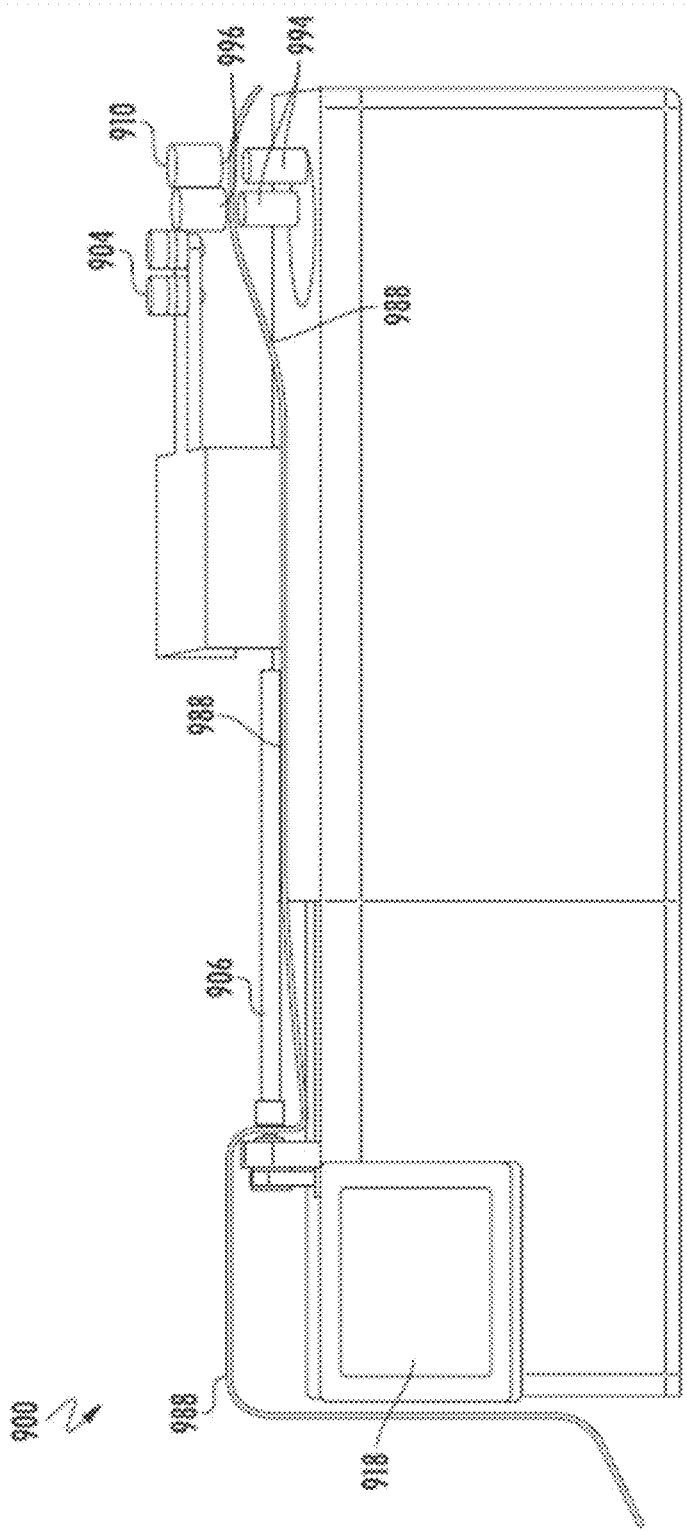

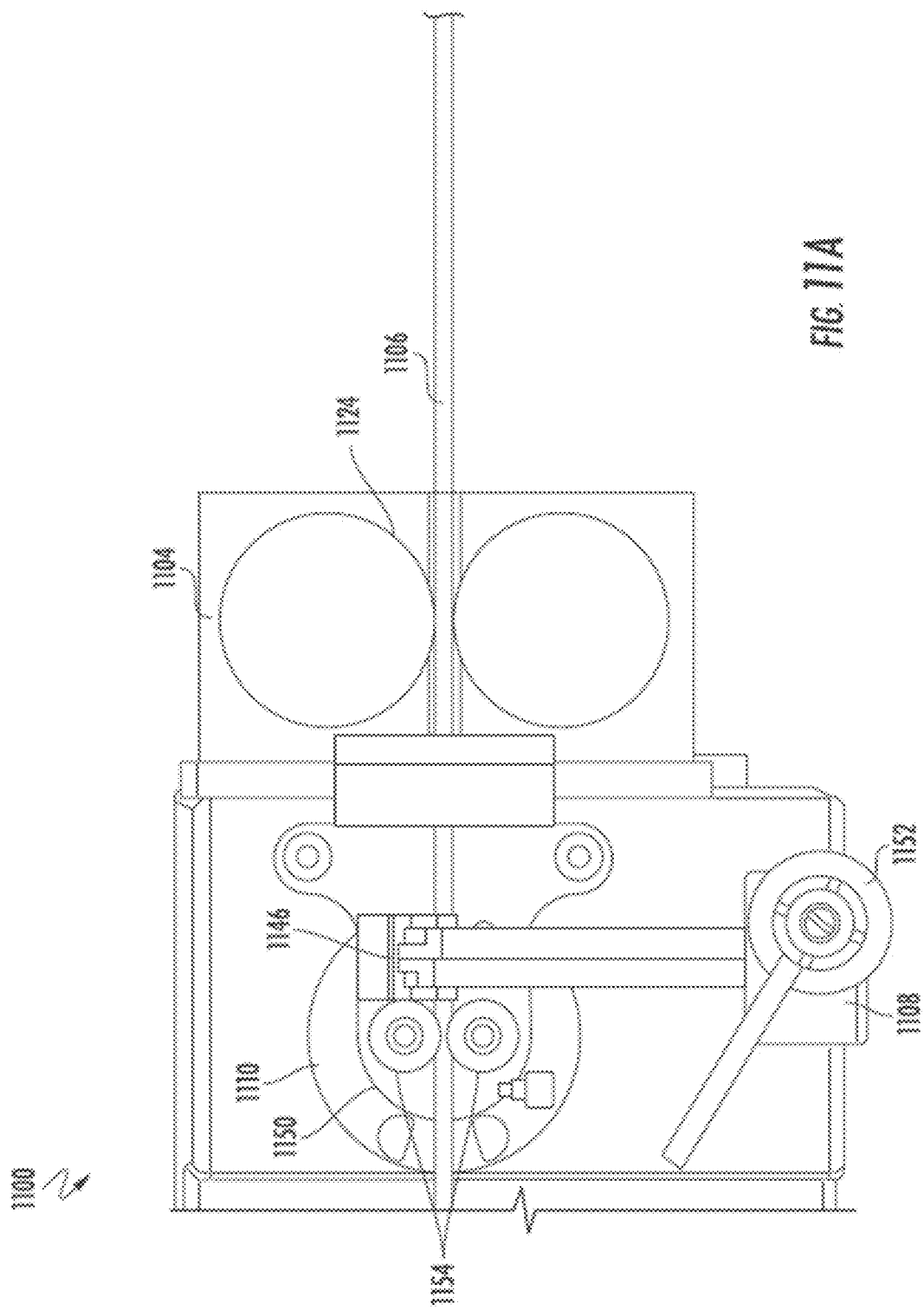

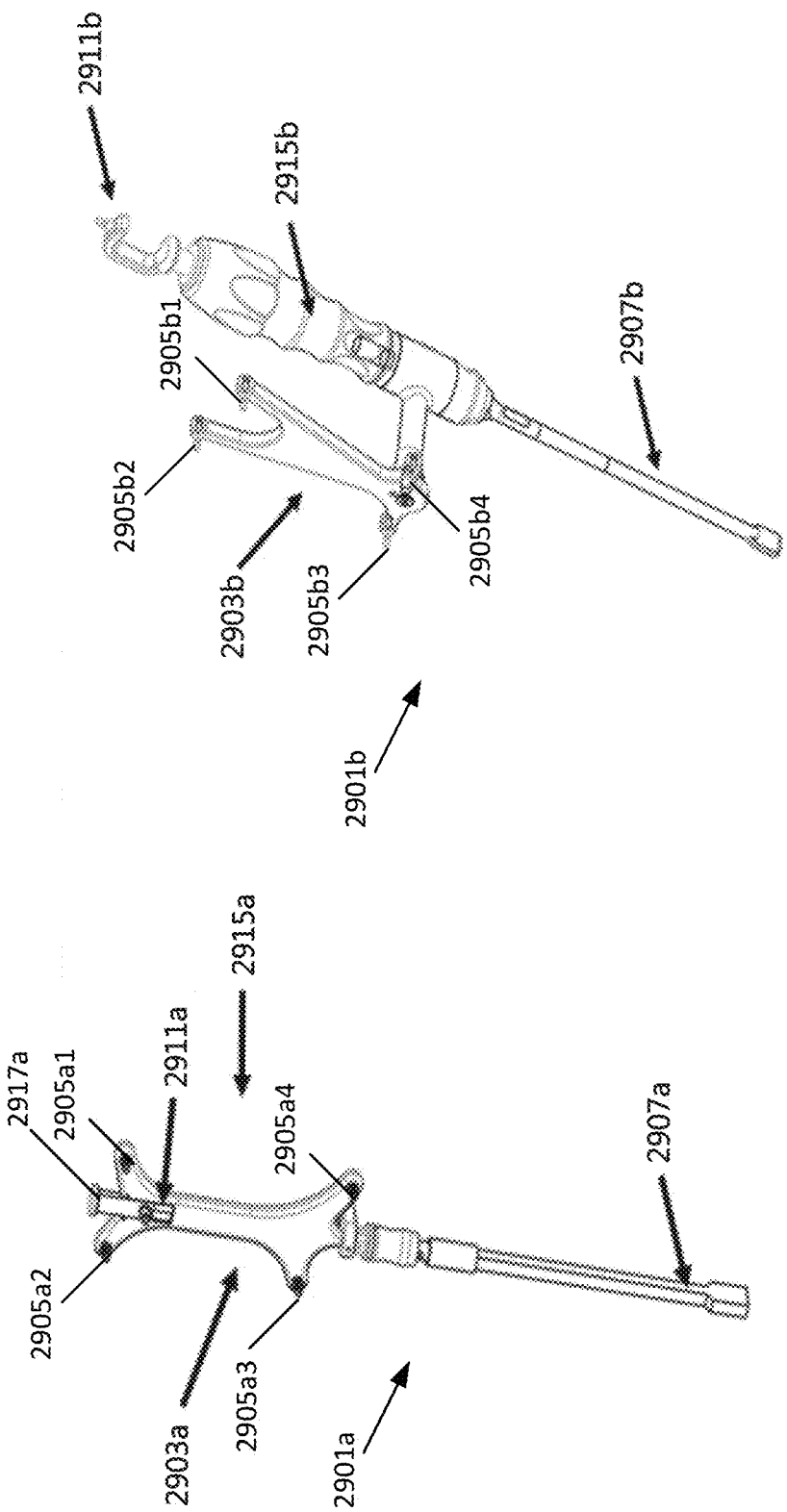

ROBOTIC ROD BENDERS AND RELATED MECHANICAL AND MOTOR HOUSINGS

RELATED APPLICATIONS

This application is a non-provisional application which claims the benefit of priority as a continuation-in-part from U.S. application Ser. No. 16/183,980 filed on Nov. 8, 2018, which claims priority to provisional application Ser. No. 62/583,851 filed on Nov. 9, 2017. The disclosures of both of the above referenced applications are hereby incorporated herein in their entireties by reference.

FIELD

The present disclosure relates to medical devices, and more particularly, surgical robotic systems for bending surgical rods, and related methods and devices.

BACKGROUND

Spinal fusion is a surgical procedure used to correct deformity of the spine by fusing together the painful part of the spine in order to restrict its motion and relieve painful symptoms. Spinal fusion surgery is commonly utilized to treat abnormal spinal curvatures, such as scoliosis and abnormal kyphosis, for example, degenerative disc diseases, spondylolisthesis, trauma resulting in spinal nerve compression, vertebral instability caused by infections or tumors, and other conditions.

Fusion surgery may include the placement of rods and screws using instrumentation and/or the placement of bone graft in between the vertebrae. During surgery, the surgeon may correct the deformity of the spine so as to ensure that the radiographic parameters of the spine in both the sagittal and coronal plane fall within clinically accepted values. While doing so, the surgeon fixes the corrected spine into place using metallic rods. The rods need to conform to the shape of the spine and hence need to be bent accordingly.

Currently, devices such as French bender and power bender are utilized in the operation room in order to bend the rods to the desired curvature. However, these devices require cumbersome manual processes to operate. In addition, use of these devices to bend the rod may also introduce notches on the rod, which may decrease the rod's fatigue life.

SUMMARY

According to some embodiments of inventive concepts, a mechanical housing may be provided for a robotic rod bender where the mechanical housing is configured to couple with a motor housing. The mechanical housing may include a rod feeding subassembly, a brake subassembly, a bending subassembly, a rod feeding transmission output, a brake transmission output, and a bending transmission output. The rod feeding subassembly is configured to feed a surgical rod in a longitudinal direction of the surgical rod. The brake subassembly is configured to receive the rod from the rod feeding subassembly and to fix the surgical rod in place. The bending subassembly is configured to bend the surgical rod while the surgical rod is fixed in place by the brake subassembly. The rod feeding transmission output is configured to provide a first self-indexing output coupling with a rod feeding transmission input from the motor housing and to drive the rod feeding assembly responsive to torque coupled from the rod feeding transmission input. The brake transmission output is configured to provide a second self-indexing output coupling with a brake transmission input from the motor housing and to drive the brake subassembly responsive to torque coupled form the brake transmission input. The bending transmission output is configured to provide a third self-indexing output coupling with a bending transmission input from the motor housing and to drive the bending subassembly responsive to torque coupled from the bending transmission input.

According to some other embodiments of inventive concepts, a motor housing may be provided for a robotic rod bender where the motor housing is configured to couple with a mechanical housing. The motor housing may include a rod feeding motor, a brake motor, a bending motor, a rod feeding transmission input, a brake transmission input, and a bending transmission input. The rod feeding motor is configured to drive a rod feeding subassembly of the mechanical housing. The brake motor is configured to drive a brake subassembly of the mechanical housing. The bending motor is configured to drive a bending subassembly of the mechanical housing. The rod feeding transmission input is configured to provide a first self-indexing input coupling with a rod feeding transmission output from the mechanical housing and to couple torque from the rod feeding motor to the rod feeding transmission output. The brake transmission input is configured to provide a second self-indexing input coupling with a brake transmission output from the mechanical housing and to couple torque from the brake motor to the brake transmission output. The bending transmission input is configured to provide a third self-indexing input coupling with a bending transmission output from the mechanical housing and to couple torque from the bending motor to the bending transmission output.

According to still other embodiments of inventive concepts, a robotic rod bender may include a motor housing and a mechanical housing coupled with the motor housing. The motor housing may include first and second rod feeding/rotating motors, a brake motor, a bending motor, first and second rod feeding/rotating transmission inputs, a brake transmission input, and a bending transmission input. The first rod feeding/rotating transmission input is configured to couple torque from the first rod feeding/rotating motor through a first self-indexing input coupling. The second rod feeding/rotating transmission input is configured to couple torque from the first rod feeding/rotating motor through a second self-indexing input coupling. The brake transmission input is configured to couple torque from the brake motor through a third self-indexing input coupling. The bending transmission input is configured to couple torque from the bending motor through a fourth self-indexing input coupling. The mechanical housing may include a rod feeding/rotating subassembly, a brake subassembly, a bending subassembly, first and second rod feeding/rotating transmission outputs, a brake transmission output, and a bending transmission output. The rod feeding/rotating subassembly is configured to feed a surgical rod in a longitudinal direction of the surgical rod and/or to rotate the surgical rod. The brake subassembly is configured to receive the rod from the rod feeding/rotating subassembly and to fix the surgical rod in place. The bending subassembly is configured to bend the surgical rod while the surgical rod is fixed in place by the brake subassembly. The first rod feeding/rotating transmission output provides a first self-indexing output coupling with the first self-indexing input coupling from the motor housing and is configured to drive the rod feeding/rotating assembly responsive to torque coupled from the first rod feeding/rotating motor. The second rod feeding/rotating transmission output provides a second self-indexing output coupling with the second self-indexing input coupling from the motor housing and is configured to drive the rod feeding/rotating assembly responsive to torque coupled from the second rod feeding/rotating motor. The brake transmission output provides a third self-indexing output coupling with the third self-indexing input coupling from the motor housing and is configured to drive the brake subassembly responsive to torque coupled form the braking motor. The bending transmission output provides a fourth self-indexing output coupling with the fourth self-indexing input coupling from the motor housing and is configured to drive the bending subassembly responsive to torque coupled from the bending motor.

BRIEF DESCRIPTION OF THE DRAWINGS

The accompanying drawings, which are included to provide a further understanding of the disclosure and are incorporated in and constitute a part of this application, illustrate certain non-limiting embodiments of inventive concepts. In the drawings:

FIG. 7 illustrates components of a bending subassembly of the bending robot of FIG. 4, according to some embodiments;

FIG. 8 illustrates a side view of the components of the bending robot of FIG. 4, according to some embodiments;

FIG. 9 illustrates components of a rod feeding subassembly for a bending robot according to another alternative embodiment;

FIGS. 11A and 11B illustrate components of a bending robot according to another alternative embodiments;

FIGS. 29A and B illustrate examples of a rod bender capture probe tip/handle assembly according to some embodiments;

DETAILED DESCRIPTION

Figure 1:
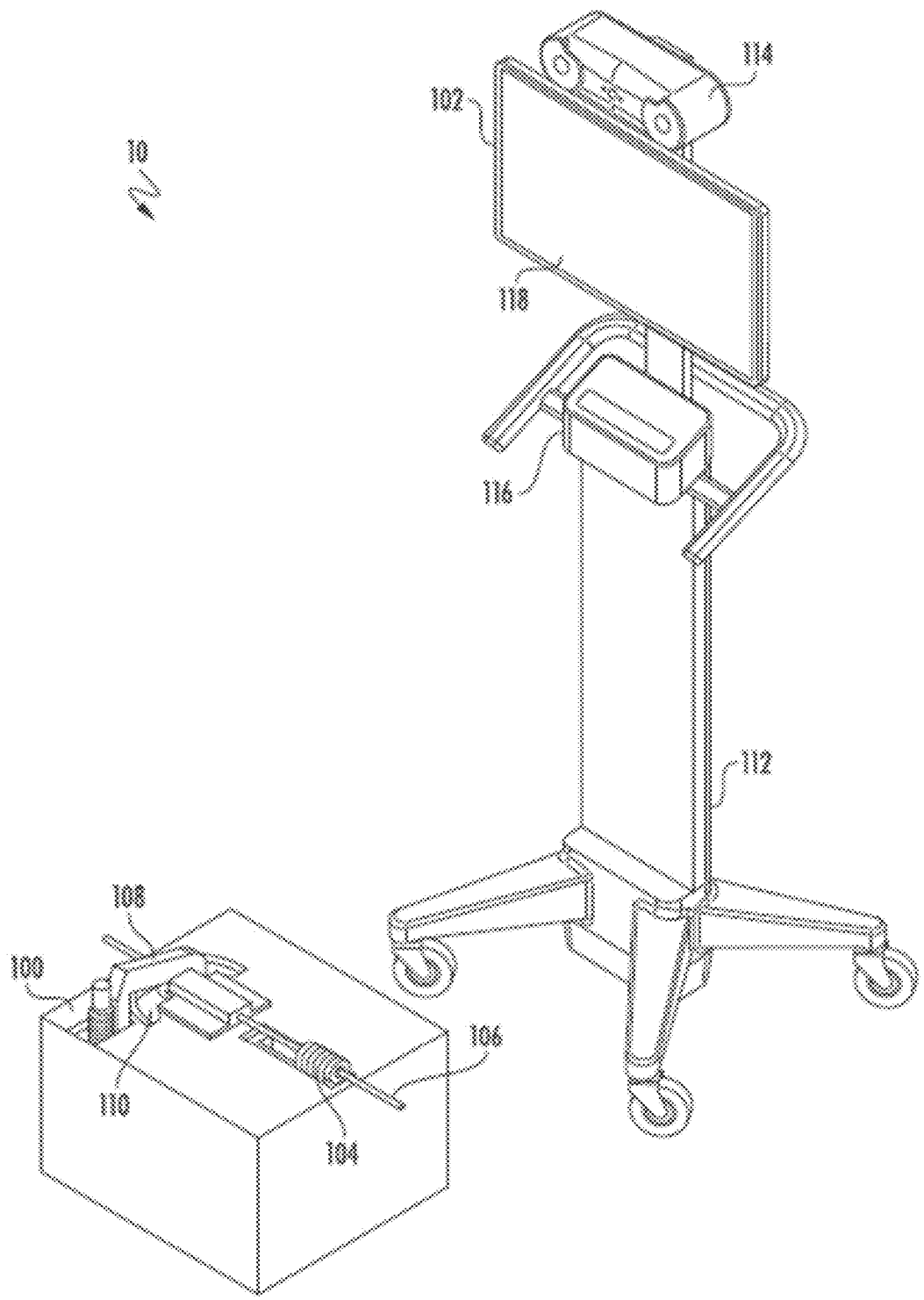
FIG. 1 illustrates a view of a robotic bending system to automatically bend a surgical rod, according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Referring now to FIG. 1, a view of a robotic bending system 10 for automatically bending a surgical rod intraoperatively is illustrated according to some embodiments. The bending system 10 of FIG. 1 includes a bending robot 100 and may also include a controller unit 102 to control and/or monitor the operation of the bending robot 100 and/or other components or devices. The bending robot 100 includes a rod feeding subassembly 104 to receive, feed, and rotate a surgical rod 106, a brake subassembly 108 to retain a first portion of the surgical rod 106 at a particular position, and a bending subassembly 110 to bend a second portion of the surgical rod 106 with respect to the first portion of the surgical rod 106 to define a bend angle between the first and second portions of the surgical rod 106. By feeding and rotating additional sections of the surgical rod 106, additional portions of the surgical rod can be bent to form a number of different shapes suitable for use in spinal fusion surgery or other procedures.

In this example, the controller unit 102 (also referred to as a controller) may include a controller base 112 and a plurality of components, which may be in communication with each other and/or components of the bending robot 100, as desired. For example, the controller unit may include a camera 114 to monitor the bending robot and/or other aspects of the surgery or procedure, an input device 116 to receive instructions from a user before or during the procedure, and a display device 118 to provide visual information to a user before or during the procedure. The robot 100 and/or controller unit 102 may include one or more processor circuits (not shown) configured to execute machine-readable instructions to operate components of the bending robot 100 or other components or devices.

Figure 2:
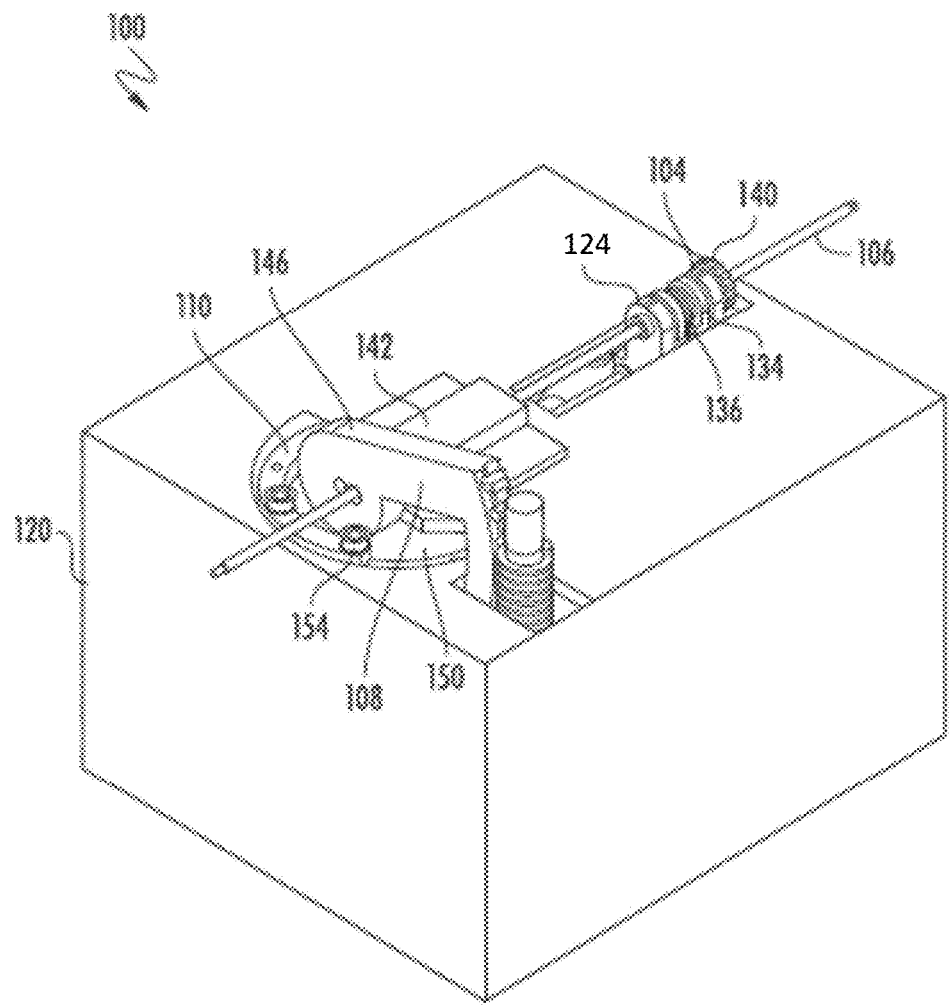
FIG. 2 illustrates a view of a bending robot of the robotic bending system of FIG. 1, according to some embodiments.

Referring now to FIG. 2, a more detailed view of the bending robot 100 of FIG. 1 is illustrated, according to some embodiments. As shown in FIG. 2, the bending robot 100 includes a robot housing 120 that is part of a robot base to house components of the rod feeding subassembly 104, brake subassembly 108, bending subassembly 110, and other components. The rod feeding subassembly 104 includes a rod feeding actuator 124 configured to retain a surgical rod 106 therein, selectively move the surgical rod 106 in a direction parallel to a longitudinal axis of the surgical rod 106, and selectively rotate the surgical rod about the longitudinal axis of the surgical rod 106. The rod feeding actuator 124 includes an actuator spindle 134 with a pulley cable 136 wound therearound, and a retaining ring 140 to retain and align the surgical rod 106. In this example, the retaining ring 140 is sized to hold the surgical rod 106 in place by friction, and to allow the rod to slide through the ring when an appropriate amount of force is applied to the surgical rod 106. The retaining ring 140 in this example may be selectively replaced with a differently sized retaining ring to accommodate a surgical rod having a different diameter. As will be discussed below, a pulley subassembly (not shown) selectively advances and rotates the surgical rod 106 to position the surgical rod 106 in a correct location and orientation with respect to the brake subassembly 108 and the bending subassembly 110. It should also be understood that, while this embodiment uses a pulley subassembly, other types of feeding actuator linkages may be used to transfer power from one or more motors to move and/or rotate the rod feeding actuator 124.

The brake subassembly 108 includes a brake housing 142 and a brake actuator 146 configured to receive the surgical rod 106 from the rod feeding subassembly 104, and selectively fix a first portion of the surgical rod 106 with respect to the brake subassembly 108. In this embodiment, after the brake actuator 146 fixes the surgical rod 106, the rod feeding subassembly 104 moves longitudinally back to its original position and may advance and/or rotate the surgical rod 106 further after the brake actuator 146 is released.

While the brake actuator 146, is engaged, the bending subassembly 110 includes a bending actuator 150 that selectively rotates about a first rotational axis perpendicular to the longitudinal axis of the surgical rod 106 to engage a second portion of the surgical rod 106 and bend the second portion of the surgical rod 106 with respect to the first portion of the surgical rod 106 so that the first portion and the second portion of the surgical rod 106 define a first bend angle. To reduce/prevent notching of the surgical rod 106 during the bending process, a pair of roller bearings 154 positioned on either side of the surgical rod 106 form the engagement points between the surgical rod 106 and the bending actuator 150 during the bending process.

Figure 3:
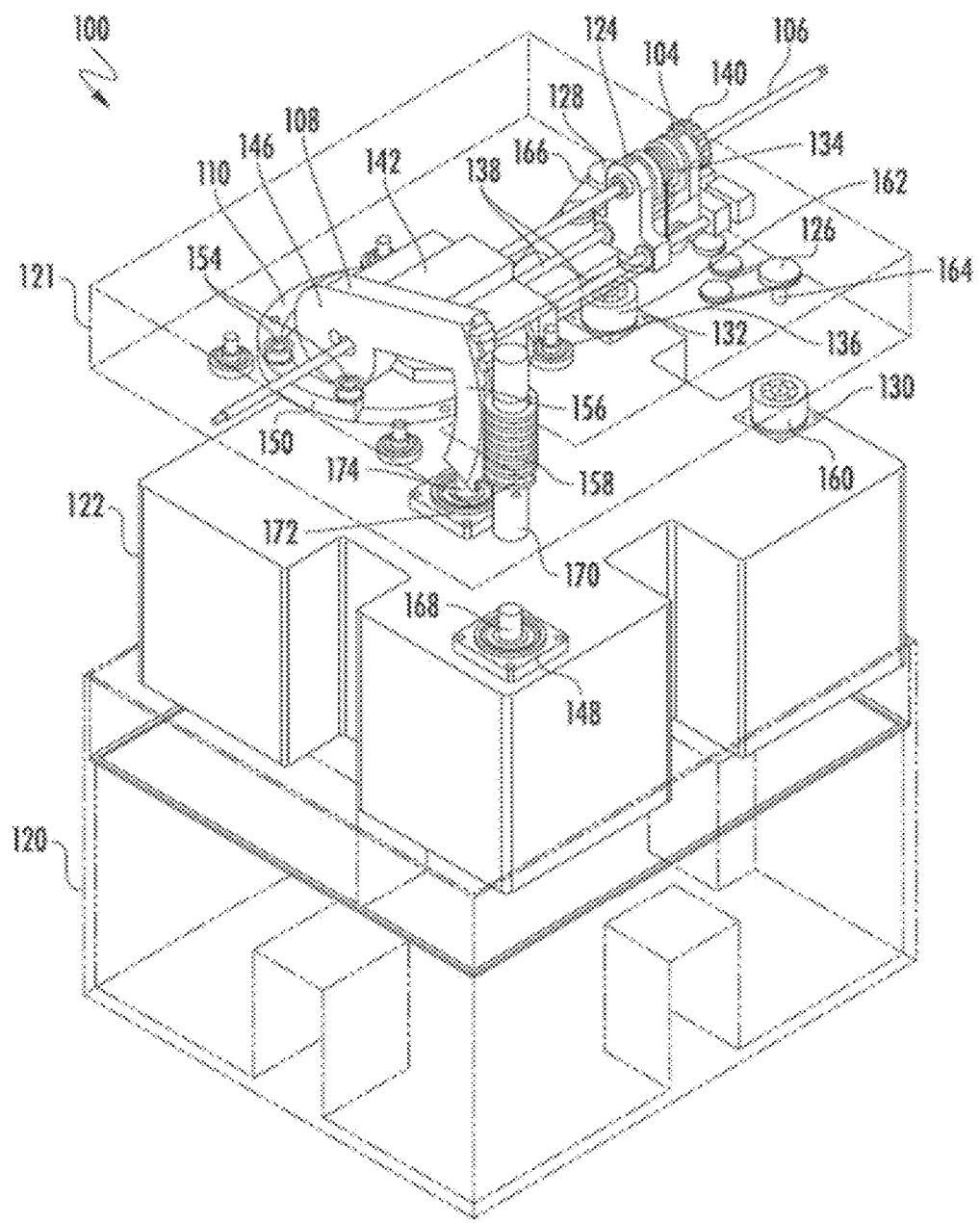
FIG. 3 illustrates a partially disassembled view of the bending robot of FIG. 2, according to some embodiments.

Referring now to FIG. 3, a partially disassembled view of the bending robot 100 of FIG. 2 is illustrated according to some embodiments. In this example, a mechanical housing 121 includes mechanical components of the rod feeding subassembly 104, brake subassembly 108, and bending subassembly 110, and a motor housing 122 includes additional components of the bending robot 100, including a first feeding actuator motor 130, a second feeding actuator motor 132, a brake actuator motor 148, a bending actuator motor 172, and/or additional internal mechanical and/electrical components such as additional linkages and/or electronic processor circuits or other circuits. For example, in some examples a memory coupled to a processor circuit may include machine-readable instructions that, when executed by the processor circuit, cause the processor circuit to cause the rod feeding subassembly 104 to selectively move the surgical rod and selectively rotate the surgical rod 106, cause the brake subassembly 108 to selectively fix the first portion of the surgical rod, and/or cause the bending subassembly 110 to selectively rotate about the first rotational axis to engage the second portion of the surgical rod 106 and bend the second portion of the surgical rod with 106 respect to the first portion of the surgical rod 106.

The mechanical housing 121 is configured to be removably coupled to the motor housing 122 so that the first and second feeding actuator motors 130, 132, brake actuator motor 148, and bending actuator motor 172 can selectively operate the rod feeding subassembly 104, brake subassembly 108, and bending subassembly 110, respectively. In this example, the mechanical housing 121 does not include any electrical or electronic components that could be damaged by conventional preoperative or intraoperative sterilization techniques, such as autoclaving, high-temperature steam sterilization, chemical sterilization, or other techniques. Thus, by disposing the non-sterile motor housing 122 in the sterile robot housing 120, and removably coupling the sterile mechanical housing 121 onto the motor housing 122, intraoperative sterility can be maintained without needing to expose the electrical and/or electronic components of the bending robot 100 to harsh sterilization techniques that may damage these components and may reduce the useful life of these components.

As shown in FIG. 3, the rod feeding subassembly includes a first pulley subassembly 126 configured to engage and be driven by the first feeding actuator motor 130, and a second pulley subassembly 128 configured to engage and be driven by the second feeding actuator motor 132. A pulley cable 136 is wound around first pulley subassembly 126 and the second pulley subassembly 128, as well as the actuator spindle 134 of the rod feeding actuator 124. The first pulley subassembly 126 includes a first pulley transmission input 160 that matingly engages with a first pulley transmission output 164 that is driven by the first feeding actuator motor 130. The first pulley subassembly 126 also includes a second pulley transmission input 162 that matingly engages with a second pulley transmission output 166 that is driven by the second feeding actuator motor 132.

In this embodiment, the directions of rotation of the first feeding actuator motor 130 and the second feeding actuator motor 132 determine the direction of movement and/or rotation of the surgical rod 106. For example, to move the rod feeding actuator 124 in a longitudinal direction along a longitudinal rail subassembly 138 toward the brake subassembly 108 and bending subassembly 110, the first feeding actuator motor 130 rotates counterclockwise and the second feeding actuator motor 132 rotates clockwise. Similarly, to move the rod feeding actuator 124 in a longitudinal direction along the longitudinal rail subassembly 138 away from the brake subassembly 108 and bending subassembly 110, the first feeding actuator motor 130 rotates clockwise and the second feeding actuator motor 132 rotates counterclockwise. To rotate the actuator spindle 134 in a clockwise direction, the first feeding actuator motor 130 rotates clockwise and the second feeding actuator motor 132 also rotates clockwise. To rotate the actuator spindle 134 in a counterclockwise direction, the first feeding actuator motor 130 rotates counterclockwise and the second feeding actuator motor 132 also rotates counterclockwise.

The brake actuator 146 is configured to engage and be driven by the brake actuator motor 148. The brake actuator 146 includes a worm gear 158 having a brake transmission input 168 that matingly engages with a brake transmission output 170 that is driven by the brake actuator motor 148. Driving the worm gear 158 causes a brake gear arm 156 to engage and/or disengage the brake actuator 146 to selectively fix or release the surgical rod 106. In this example, selective operation of the brake actuator motor 148 in a first rotational direction when the brake actuator 146 is in a neutral position causes the brake gear arm 156 to move the brake actuator 146 from the neutral position to an engaged position to selectively fix the first portion of the surgical rod 106 with respect to the brake subassembly 108. Similarly, selective operation of the brake actuator motor 148 in a second rotational direction opposite the first rotational direction when the brake actuator 146 is in the engaged position causes the brake gear arm 156 to move the brake actuator 146 from the engaged position to the neutral position to selectively release the surgical rod 106. In this example, the brake subassembly 108 is a brake and cutting subassembly that further includes an internal blade mechanism (not shown), wherein selective operation of the brake actuator motor 148 in the second rotational direction when the brake actuator 146 is in the neutral position causes a blade of the internal blade mechanism to cut the surgical rod 106. In this example, two internal plates may be slid apart in a reverse scissoring motion, introducing tension to the rod in two different directions and trimming the excess. It should also be understood that an alternative or additional brake actuator linkage may be used in place of or in addition to the worm gear 158 and brake gear arm 156 of the brake subassembly 108.

Similar to the rod feeding subassembly 104 and the brake subassembly 108, the bending actuator 150 of bending subassembly 110 includes a bending transmission output (not shown) that matingly engages with a bending transmission input 174 that is driven by the bending actuator motor 172, and that transfers power from the bending actuator motor 172 through a bending actuator linkage (not shown) to drive the bending actuator 150. Thus, when the sterile mechanical housing 121 is removably coupled to the motor housing 122 in the sterile robot housing 120, the bending robot 100 is able to automatically bend the surgical rod 106 in real-time in a sterile, intraoperative environment. Following each bend, the previously fixed portion of the surgical rod 106 may be advanced and/or rotated by the rod feeding subassembly 104 and another portion may be fixed by the brake subassembly 108. The bending subassembly 110 then bends the previously fixed portion of the surgical rod 106, and so on, until the rod is bent to a desired shape and can be cut and used as part of the spinal fusion surgery or other procedure.

Figure 4:
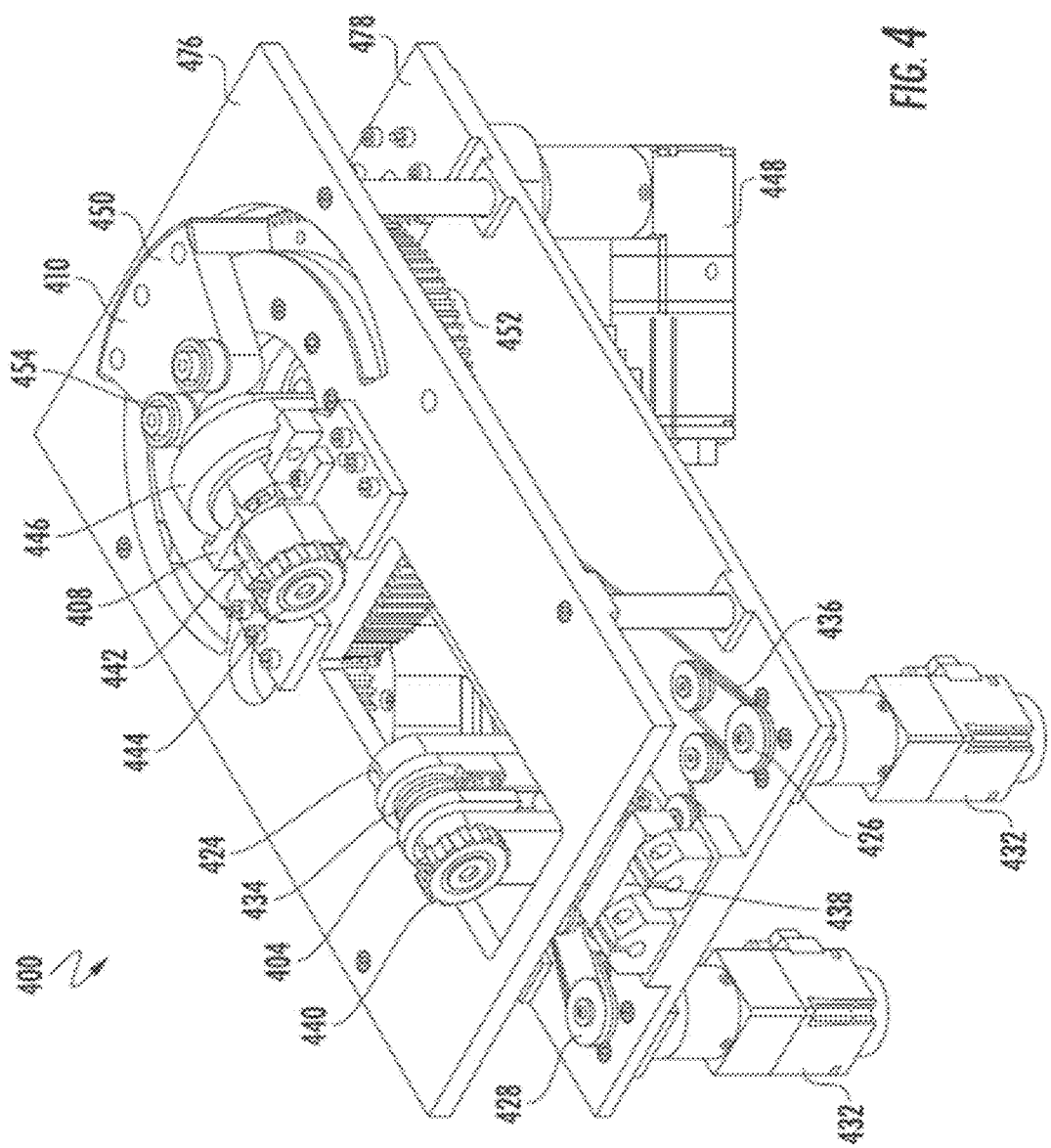
FIG. 4 illustrates an internal view of components of a bending robot according to an alternative embodiment.
Figure 5:
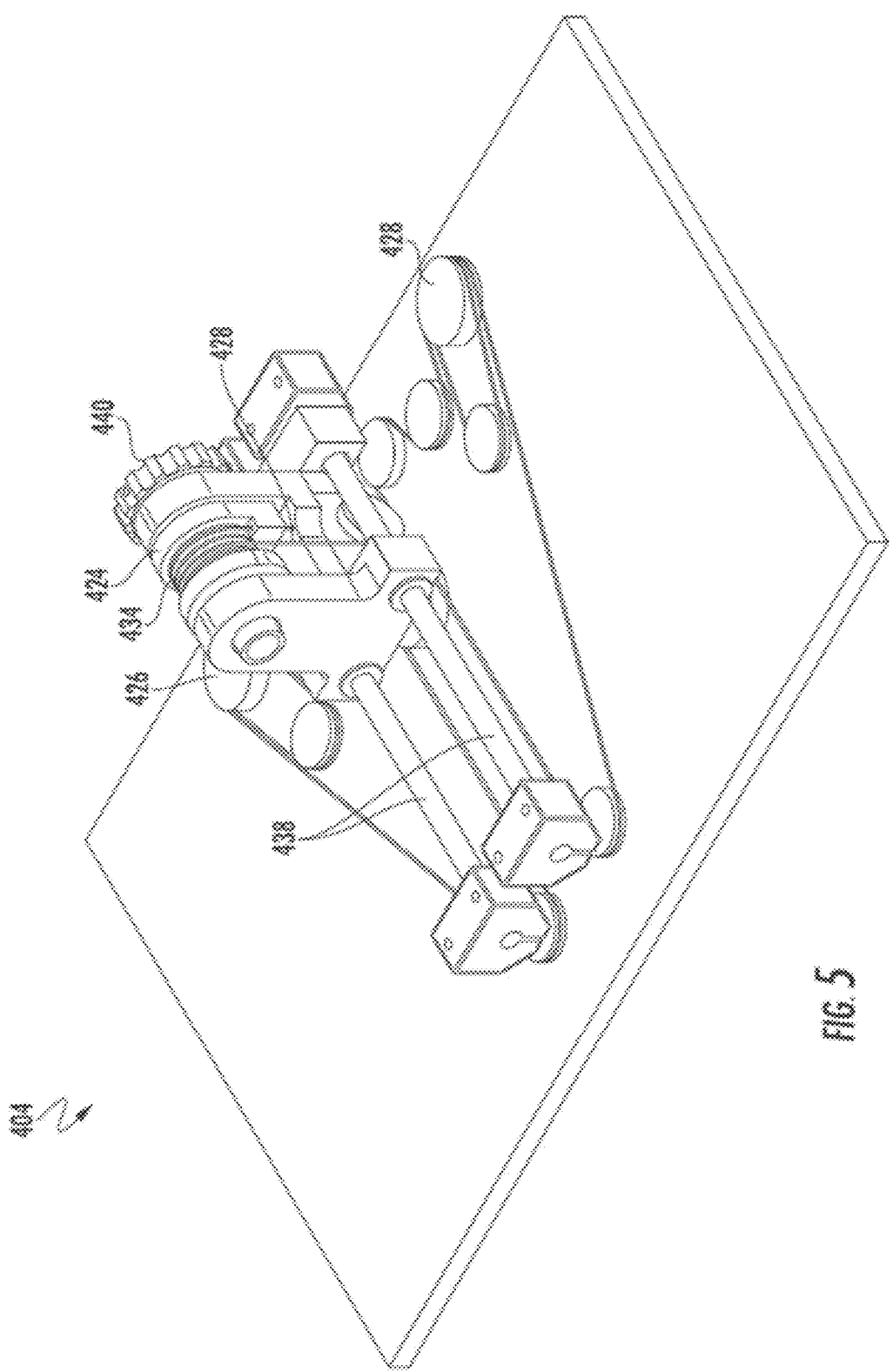
FIG. 5 illustrates components of a rod feeding subassembly of the bending robot of FIG. 4, according to some embodiments.

Referring now to FIGS. 4-7, components of a bending robot 400 according to an alternative embodiment are illustrated. As shown by FIG. 4, the bending robot 400 in this embodiment includes a rod feeding subassembly 404, a brake and cutting subassembly 408, and a bending subassembly 410. As shown by FIGS. 4 and 5, the rod feeding subassembly 404 includes a rod feeding actuator 424 that is selectively longitudinally movable and rotatable via a first pulley subassembly 426 and second pulley subassembly 428. A first feeding actuator motor 430 and a second feeding actuator motor 432 transfer power through the first pulley subassembly 426 and second pulley subassembly 428 via a pulley cable 436 to move the actuator spindle 434 along a longitudinal rail subassembly 438 and rotate the actuator spindle. The actuator spindle 434 includes a removable retaining ring 440 to retain and align the surgical rod (not shown) therein.

Figure 6:
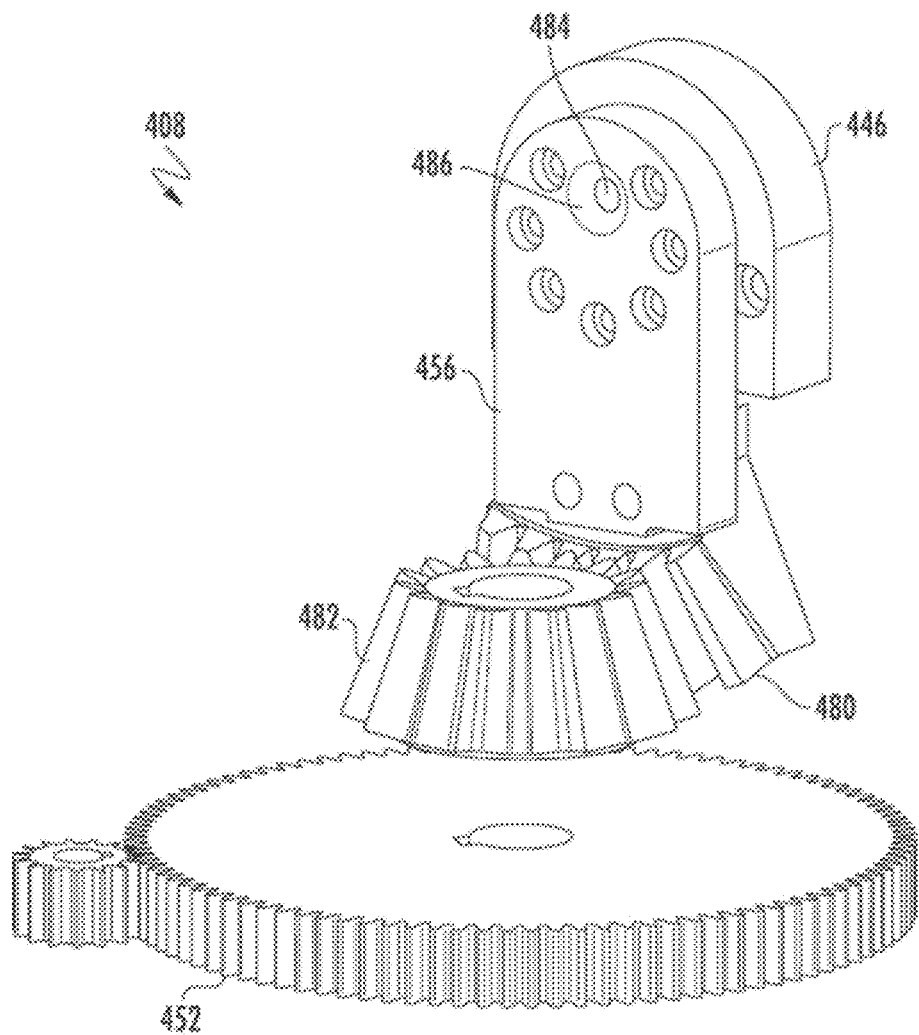
FIG. 6 illustrates components of a brake and cutting subassembly of the bending robot of FIG. 4, according to some embodiments.

As shown by FIGS. 4, the brake and cutting subassembly 408 includes a brake housing 442 having a retaining ring 444 similar to the retaining ring 440 of the rod feeding subassembly 404, to receive and align the surgical rod. A brake actuator 448 is controlled by a brake actuator motor 448 to selectively fix and/or release the surgical rod. As shown by FIG. 6, the brake actuator 446 includes a brake gear subassembly including a brake gear 482. In this example, the brake gear is coaxial with, but independently rotatable with respect to, the main gear of the bending gear subassembly 452. This arrangement is to conserve internal space, but it should be understood that other mechanical arrangements may be used to achieve the same or similar functionality. In this example, rotating the brake gear 482 causes the brake gear arm 456 to rotate in a first direction from a neutral position, wherein the surgical rod can be freely moved and rotated with respect to through-hole 484, to an engaged position, wherein the brake gear arm rotates to compress the surgical rod within the through-hole and fix the surgical rod in place. In this embodiment, rotating the brake arm from the neutral position in an opposite direction causes a blade of an internal blade mechanism (not shown) to cut the surgical rod.

Referring now to FIG. 7, the bending subassembly 410 includes a bending actuator 450 controlled by a bending actuator motor 472 via a bending gear subassembly 452. A pair of roller bearings 454 are configured to engage the surgical rod when the bending actuator 450 is rotated to bend the surgical rod to a predetermined bend angle.

FIG. 8 illustrates a side view of the components of the bending robot 400 of FIG. 4. As shown by FIG. 8, the components of the bending robot 400 in this example are coupled to an upper support structure 476 and a lower support structure 478 coupled to and spaced apart from the upper support structure 476, to provide structural support for the components of the bending robot 400 while allowing for easier access to the components of the bending robot 400 for maintenance and repair, for example.

Many techniques are available to sterilize and reduce/prevent contamination of a surgical rod being bent in an intraoperative environment. For example, the embodiment of FIGS. 2 and 3 includes a removable mechanical housing 121 that can be completely sterilized using conventional sterilization techniques without risking damage to the electrical or other components of the separate motor housing 122. In another example illustrated in FIG. 9, a bending robot 900 includes a rod feeding subassembly 904 and a bending subassembly 910 to feed, rotate and bend a surgical rod 906. In this example, the bending robot 900 includes integrated computing components, including an integrated display 918, to control the bending robot 900.

In the embodiment of FIG. 9, a sterile drape 988 may cover the non-sterilized components of the bending robot 400, with sterilized components being coupled to the non-sterilized components via magnetic connectors 990, 994 of the sterilized components matingly coupling to complementary magnetic connectors 992, 996 (e.g., male-female connections) of the non-sterilized components, with motion of the components being transferred through the drape 988. While magnetic connections are used in this embodiment, it should be understood that other connections, such as a tight-fit mechanism that allows for transferring mechanical motion without compromising the integrity of the drape 988, may be used. For example, in this and other embodiments, the rotatable components do not require a range of motion of more than 180 degrees. Because of this relatively small range of rotation, using a tight fit mechanism is possible without tearing or otherwise unduly straining the drape 988.

Figure 10A:
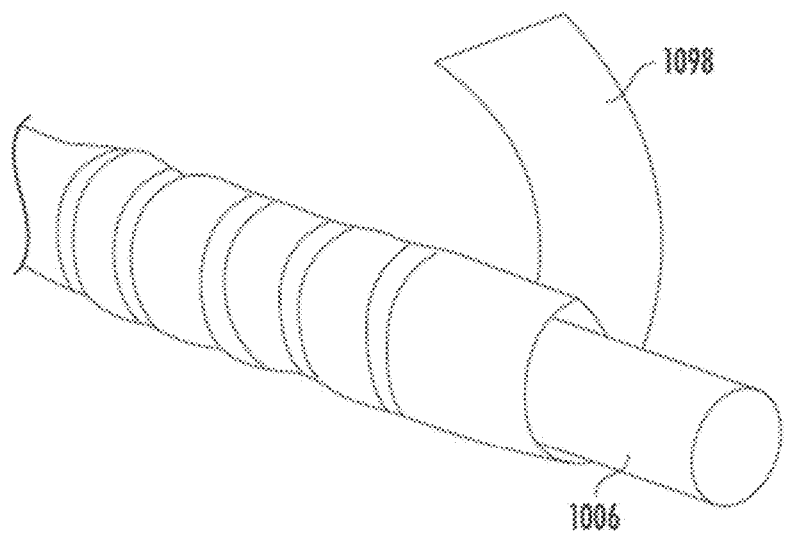
FIGS. 10A-D illustrate surgical rods having removable sterile sleeves, according to some embodiments.

In some embodiments, a sterile surgical rod may be sealed within a sterile sleeve or wrap, which is then bent intraoperatively in a non-sterile environment. In this regard, FIGS. 10A-D illustrate surgical rods having removable sterile sleeves as illustrated, according to some embodiments. Referring to FIG. 10A, a sterile surgical rod 1006 is wrapped in a spiral sterile wrap 1098 material. Following bending of the surgical rod 1006, the spiral sterile wrap 1098 may be removed and the sterile surgical rod 1006 may be delivered into the sterile intraoperative environment.

Figure 10B:
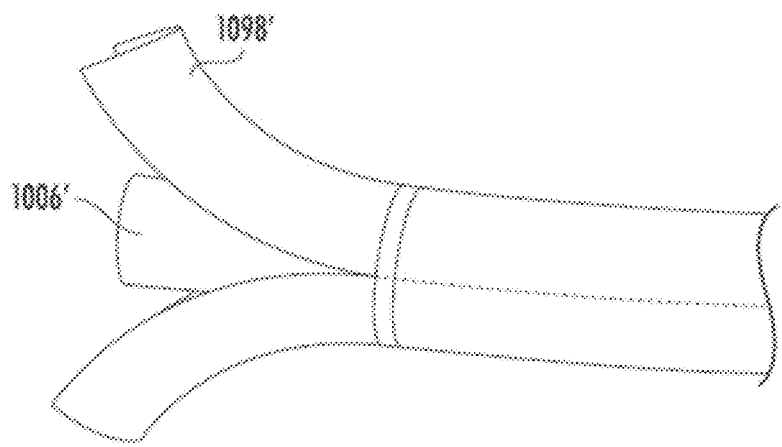
Figure 10C:
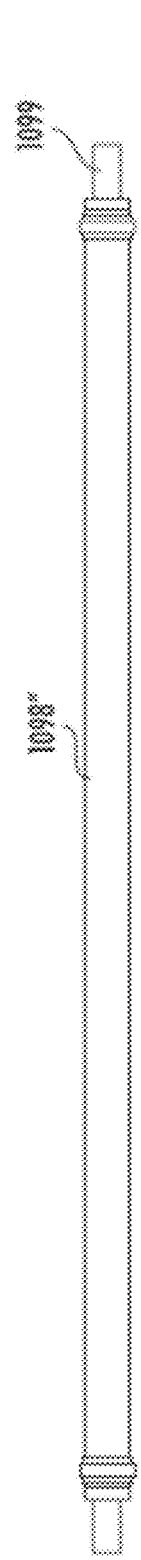
Figure 10D:

Similarly, FIG. 10B illustrates another sterile surgical rod 1006' having a sterile sleeve 1098' that may be peeled away from the sterile surgical rod 1006' following bending of the sterile surgical rod 1006'. FIGS. 10C and 10D illustrate a sterile surgical rod 1006" disposed in a sterile flexible shaft 1098", which is sealed at either end by removable caps 1099. A bending robot in a non-sterile environment may be configured to bend the flexible shaft 1098", thereby bending the sterile surgical rod 1006" within the flexible shaft 1098" without contacting or contaminating the sterile surgical rod 1006".

Following the bending process, the sterile surgical rod 1006" may be removed from the flexible shaft 1098" and delivered into the sterile intraoperative environment. In these and other embodiments, the coverings for the sterile surgical rods 1006, 1006', 1006" may have a uniform outer diameter, so that different surgical rod diameters may be used without the need for a bending robot to adjust to different outside diameters of the respective coverings.

Figure 11B:
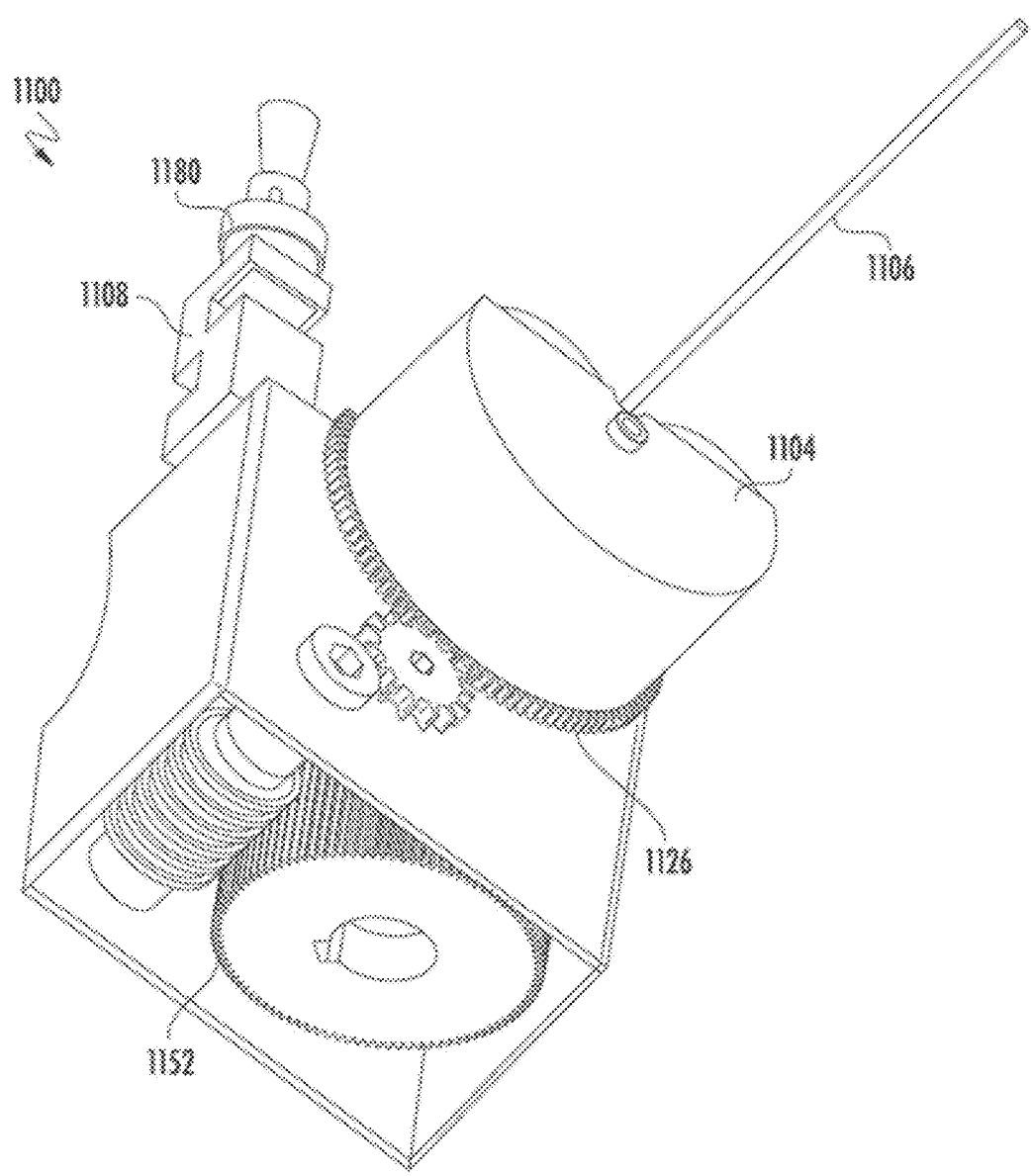

FIGS. 11A and 11B illustrate components of a bending robot 1100 according to another alternative embodiment. The bending robot 1100 in this embodiment includes a rod feeding subassembly 1104 including a rod feeding actuator 1124, a brake subassembly 1108 with a brake actuator 1146 having an integrated marking mechanism, and bending subassembly 1110 having a bending actuator 1150 including a pair of roller bearings 1154 configured to engage and bend the surgical rod 1106 without notching or otherwise damaging the surgical rod 1106.

In this example, the rod feeding actuator 1124 is controlled via a feeding gear mechanism 1126, and the bending actuator 1150 is controlled via a bending gear subassembly 1152. The brake actuator 1146 is controlled by a manual clamp mechanism 1180 in this embodiment. An integrated marking mechanism, e.g., a retractable marker, may mark points on the rod which, once marked, dictate the shape of the rod as needed to correct an injury, where the marked points indicate the points of the screws along the curve of the bend. This allows for additional control over the shape of the rod, and marking ensures that the surgeon is aware entirely of which screws the rod aligns with for a spinal fusion or other procedure. Alternatively, the surgical rod could be pre-marked, e.g., every five millimeters, with a corresponding number. By displaying these numbers on the screen of a monitor viewable by the surgeon during the procedure, the surgeon can ensure proper positioning of the rods.

Figure 12:
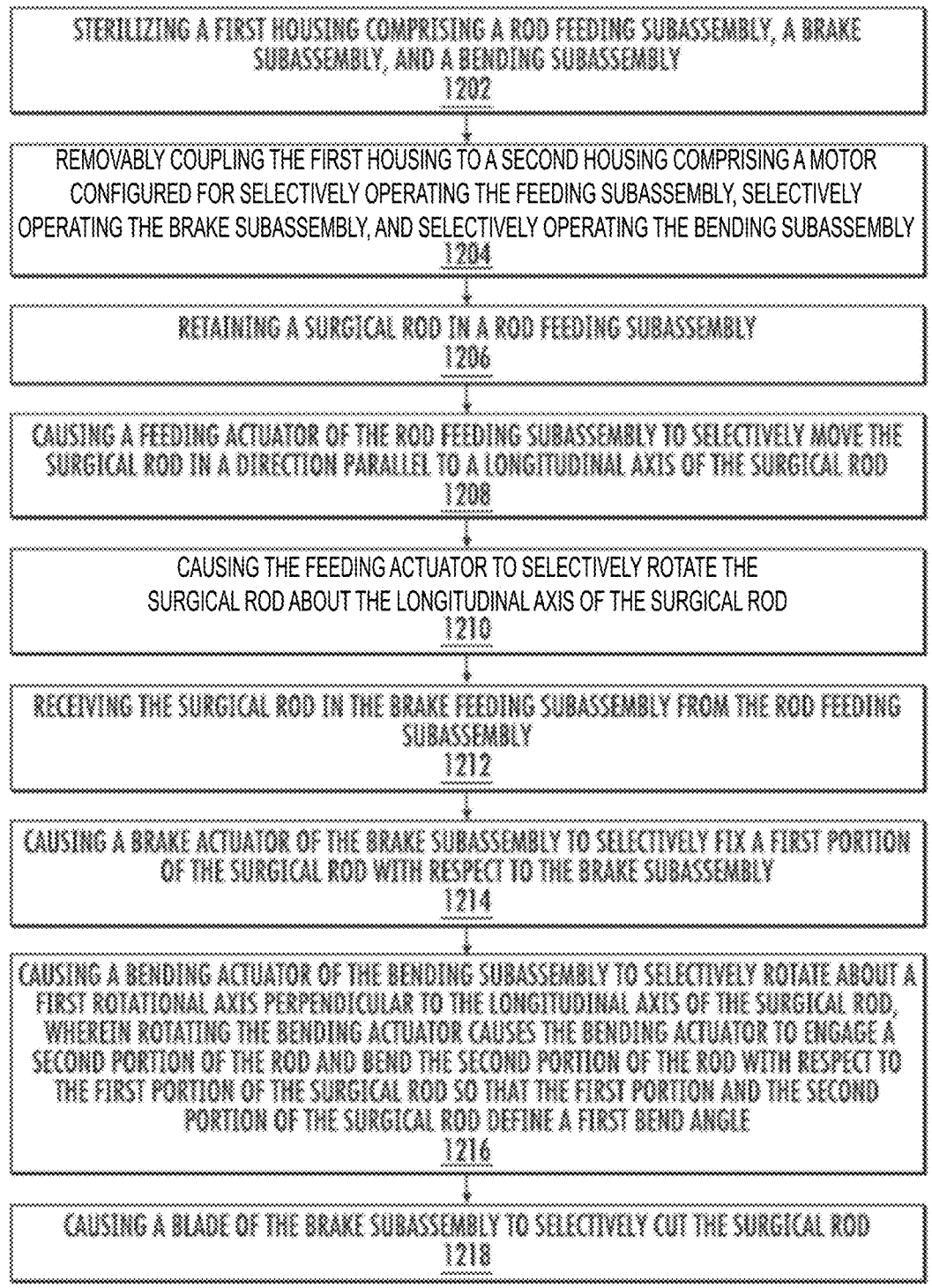
FIG. 12 is a flowchart of a method of operating a bending robot, according to some embodiments.

FIG. 12 is a flowchart of operations 1200 to operate a bending robot, according to some embodiments. The operations 1200 include sterilizing a first housing including a rod feeding subassembly, a brake subassembly, and a bending subassembly (Block 1202), and removably coupling the first housing to a second housing including a motor configured to selectively operate the rod feeding subassembly, the brake subassembly, and the bending subassembly (Block 1204). The operations 1200 further include retaining a surgical rod in the rod feeding subassembly (Block 1206), causing a feeding actuator of the rod feeding subassembly to selectively move the surgical rod in a direction parallel to a longitudinal axis of the surgical rod (Block 1208), and causing the feeding actuator to selectively rotate the surgical rod about the longitudinal axis of the surgical rod (Block 1210).

The operations 1200 further include receiving the surgical rod in the brake feeding subassembly from the rod feeding subassembly (Block 1212), and causing a brake actuator of the brake subassembly to selectively fix a first portion of the surgical rod with respect to the brake subassembly (Block 1214). The operations 1200 further include causing a bending actuator of the bending subassembly to selectively rotate about a first rotational axis perpendicular to the longitudinal axis of the surgical rod, wherein rotating the bending actuator causes the bending actuator to engage a second portion of the rod and bend the second portion of the rod with respect to the first portion of the surgical rod so that the first portion and the second portion of the surgical rod define a first bend angle. The operations 1200 further include causing a blade of the brake subassembly to selectively cut the surgical rod.

Additional operations may include data acquisition, which may occur prior to rod bending and after screws are properly placed via a camera system, which may send the data to the bending robot. Based on the data, the bending robot may perform the operations described above. In another embodiment, the data for bend points can be received through an acquisition camera and a probe that is tracked by the camera, where the probe is touched on the head of each of a plurality of pedicle screws after they have been placed on the patient's spine. Those points can be used to generate a curve that can be modified and fine-tuned by the surgeon, and that can be used to generate bend points, which can be used by the bending robot to make appropriate bends in the surgical rod. In another example, an intraoperative robot used for screw placement can be used to determine the coordinates of the pedicles and hence can be used to generate a bend curve. In some embodiments, preoperative planning software, such as Surgimap or GMAP, for example, can be used to configure the bend points, which can then be used by the bending robot to bend the surgical rod. Data from the camera may also be used to verify that the robot is operating correctly and/or within predetermined tolerances, and may generate data to instruct the robot to correct for errors in real time.

Further discussion of elements of bending robot 110 is provided below with respect to FIGS. 45-53.

Figure 45:
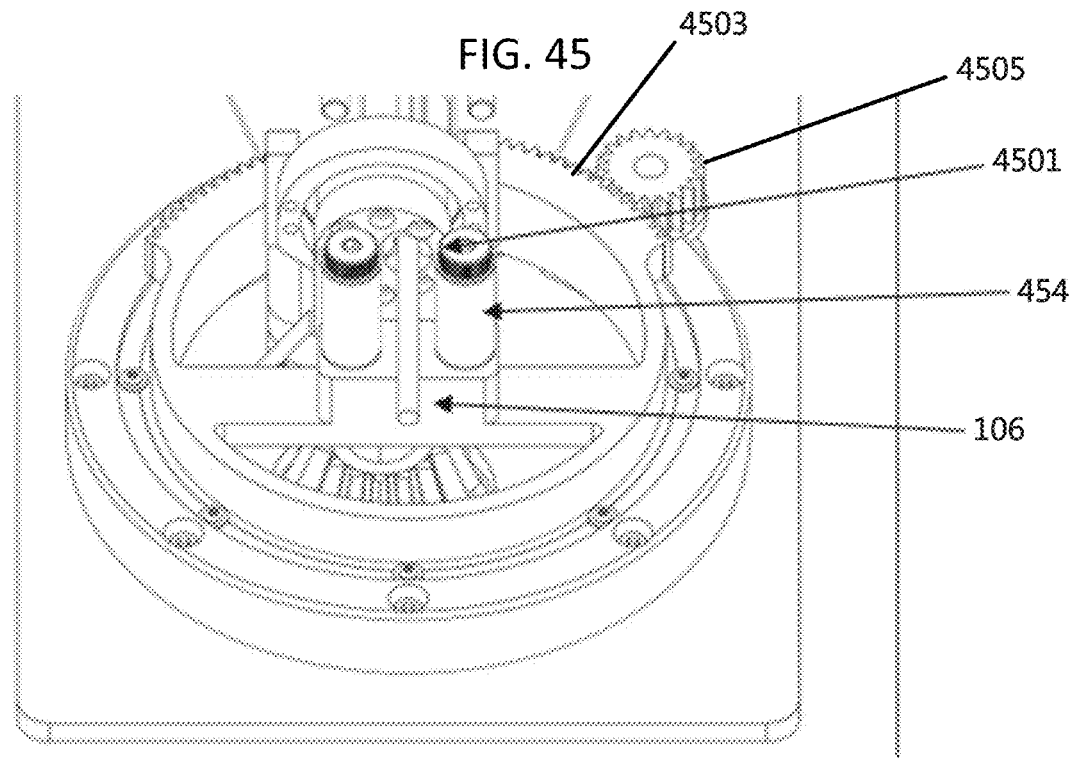
FIGS. 45-53 are exploded views of elements of mechanical housings of bending robots according to some additional embodiments of inventive concepts.
Figure 46:
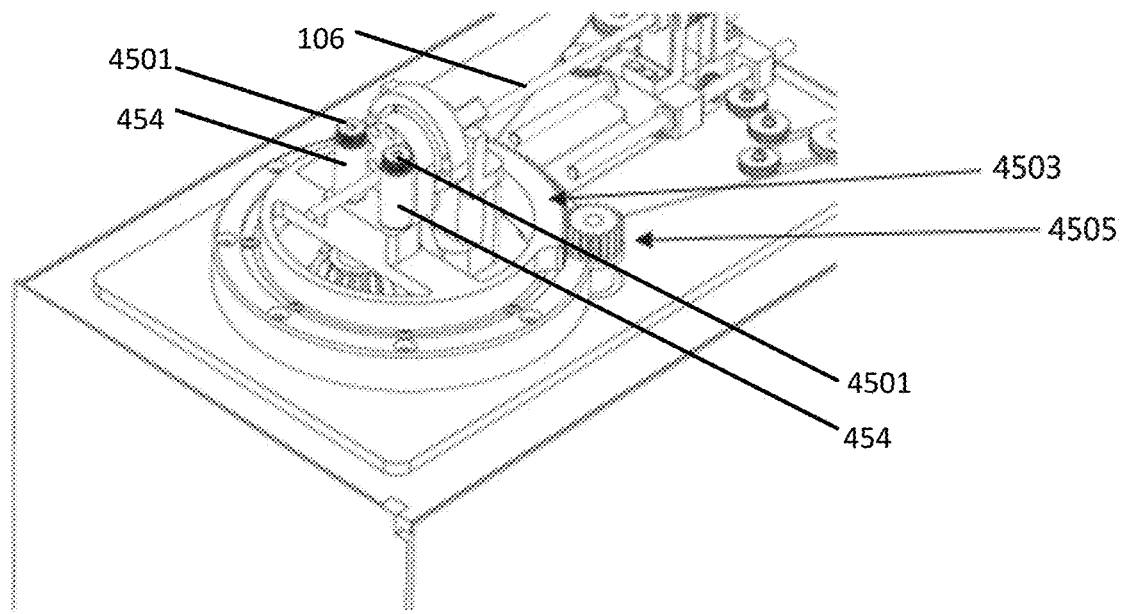
Figure 47:
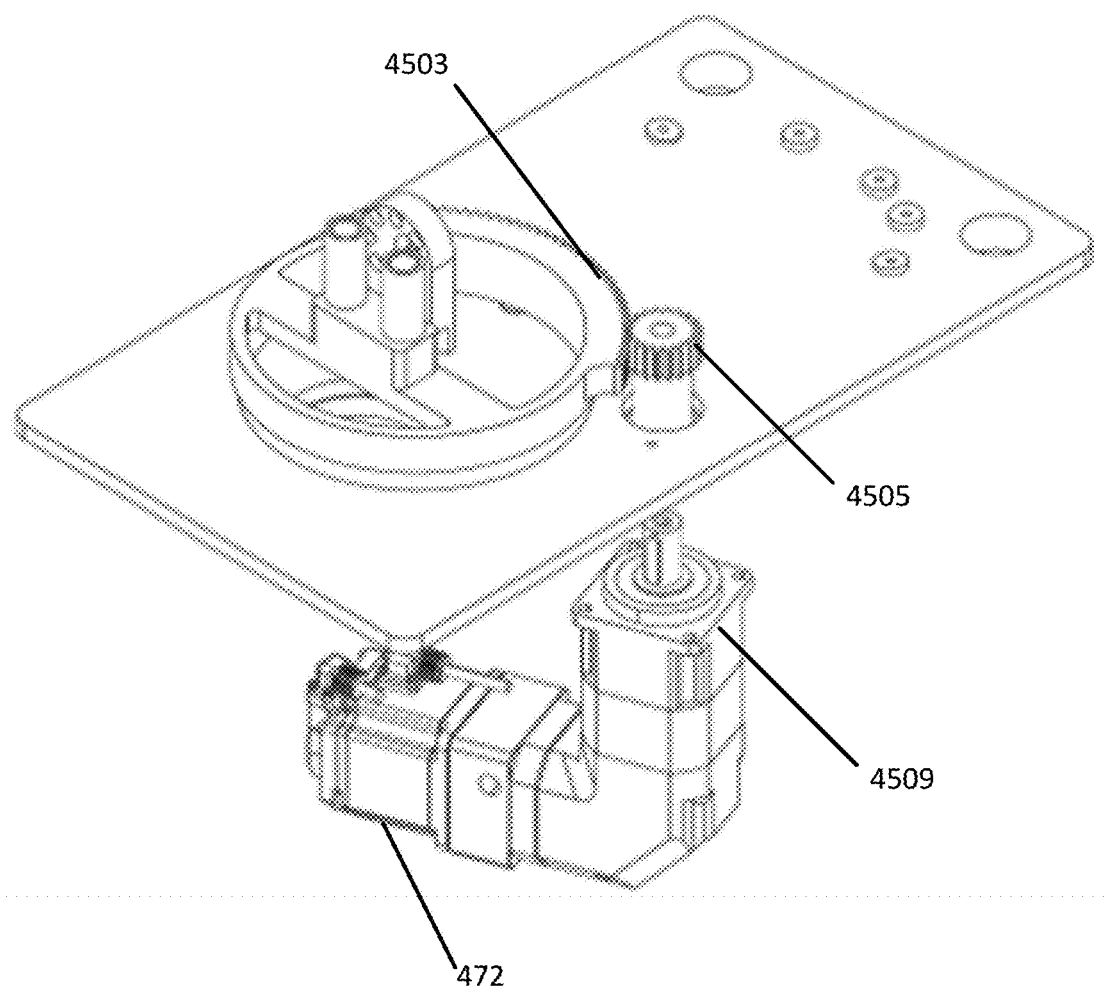

FIGS. 45, 46, and 47 illustrate additional details of a bending subassembly from a mechanical housing of a bending robot. As shown in FIGS. 45 and 46, surgical rod 106 is fed into the bending subassembly (also referred to as a bend mechanism) using a rod feeding subassembly (also referred to as a feed carriage). Roller bearings 454 (also referred to as bend rollers) surround respective bend posts 4501 which push the surgical rod 106 to create a precalculated bend in the surgical rod. Roller bearings (bend rollers) 454 roll on respective bend posts 4501 while pushing the surgical rod to reduce damage to the surface of the surgical rod while bending.

As shown, the roller bearings 454 and/or bend posts 4051 are attached to a plate of the bending actuator which includes a section of a spur gear referred to as driven gear 4503. This larger driven gear 4503 is controlled by a smaller spur gear referred to as drive gear 4505. This mechanism may provide sufficient mechanical advantage to match a torque value used/required to bend a metallic surgical rod. As shown in FIG. 47, drive gear 4505 is connected to bending actuator motor 472 via a gearbox 4509 to provide the gear reduction used/required to bend the strongest surgical rods used for spinal correction. Drive gear 4505 and driven gear 4503 may be provided as elements of bending gear subassembly.

Figure 48:
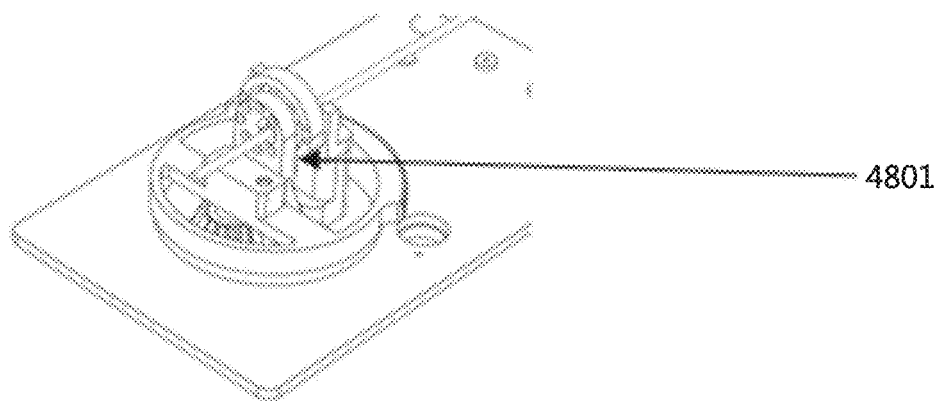
Figure 49:
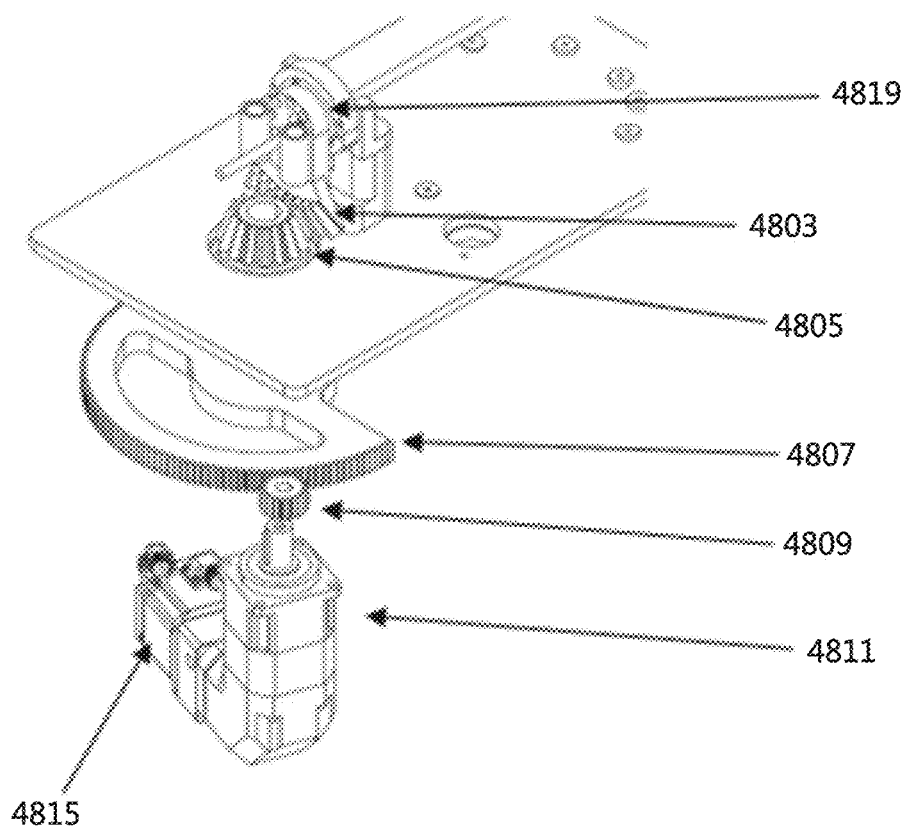

FIGS. 48 and 49 illustrate additional details of a braking/cutting subassembly from a mechanical housing of a bending robot. The cut axis may use/require more than a thousand times gear reduction to provide a torque used/required to cut the strongest surgical rods used for spinal correction. As shown in FIGS. 48 and 49, the cutter arm 4801 may be attached to a section of a bevel gear 4803. The section of the bevel gear 4803 may be compounded with a pinion bevel gear 4805, a big spur gear 4807, a small pinion spur gear 4809, and a right angle gearbox 4811 to provide sufficient gear reduction in a mechanical coupling with motor 4815 (which may be provided in a motor housing of the bending robot). The cutter arm rotates on a shear plane 4819 perpendicular to the top plate and cuts the rod through a shear mechanism. Rotation in a first direction may thus be provided to cut the rod, while rotation in a second direction may be used to brake the rod (i.e., to hold the rod in a fixed position to prevent lengthwise and rotational movement) while bending the rod as discussed below.

Figure 50:
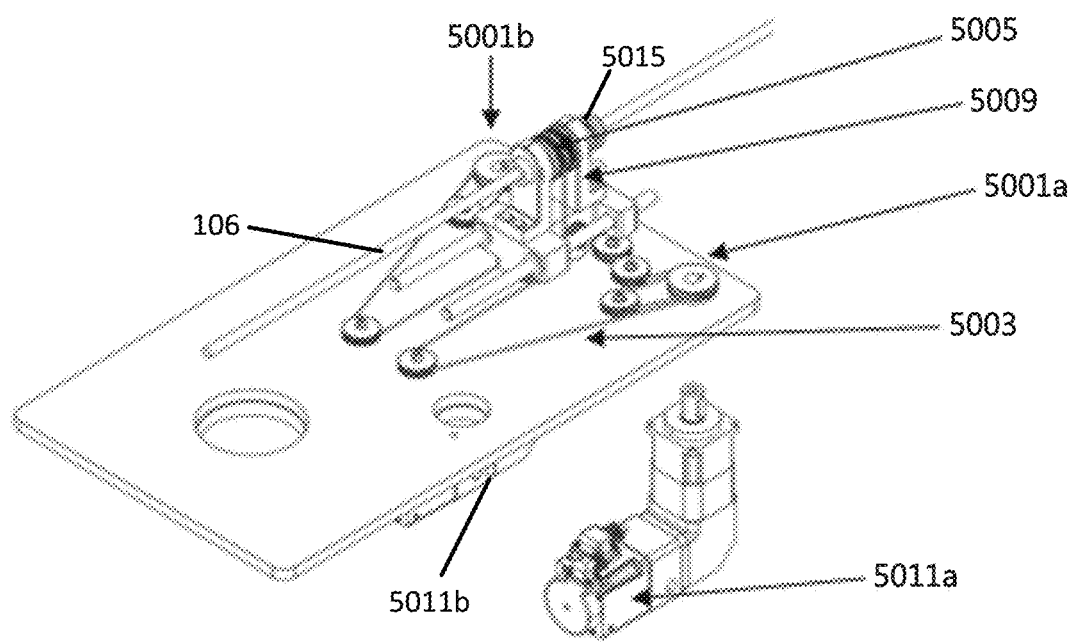
Figure 51:
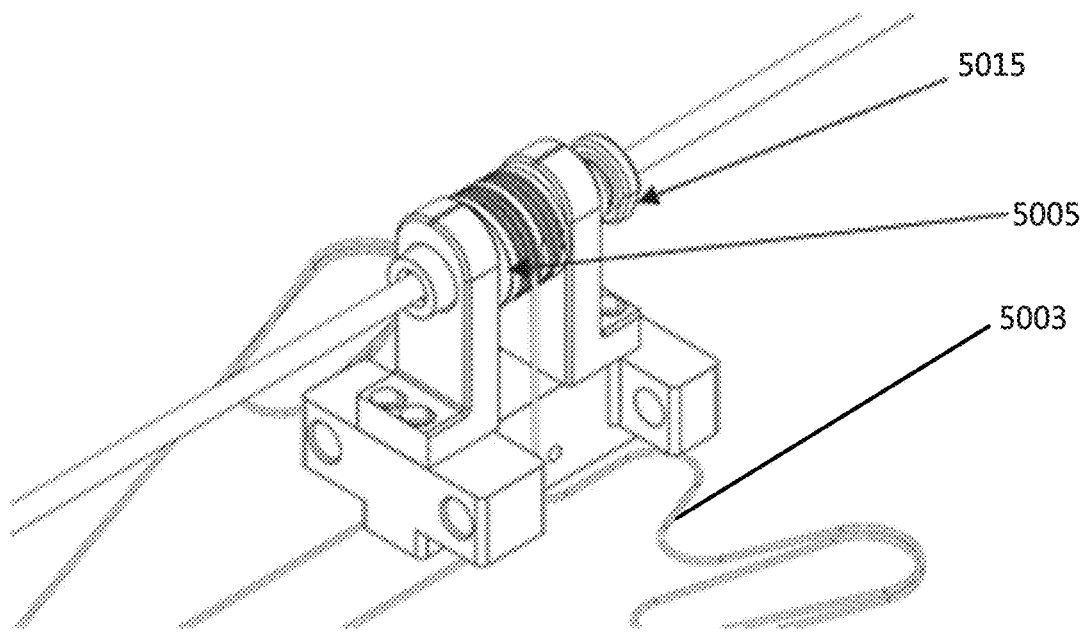
Figure 52:
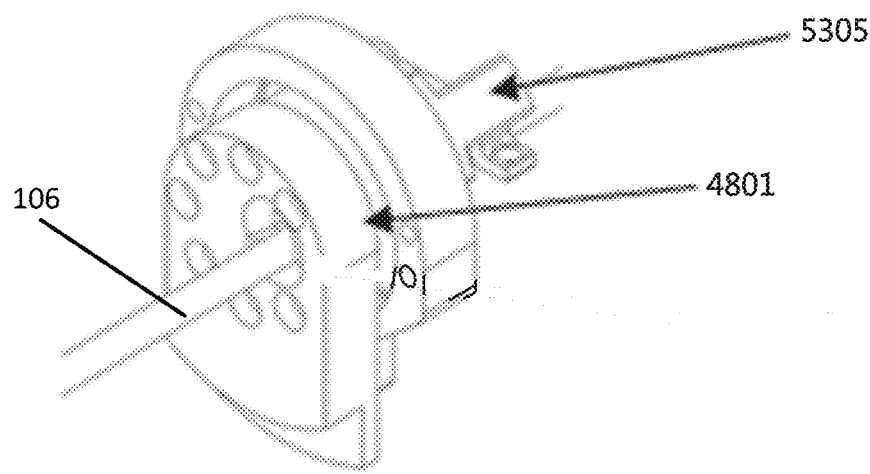
Figure 53:
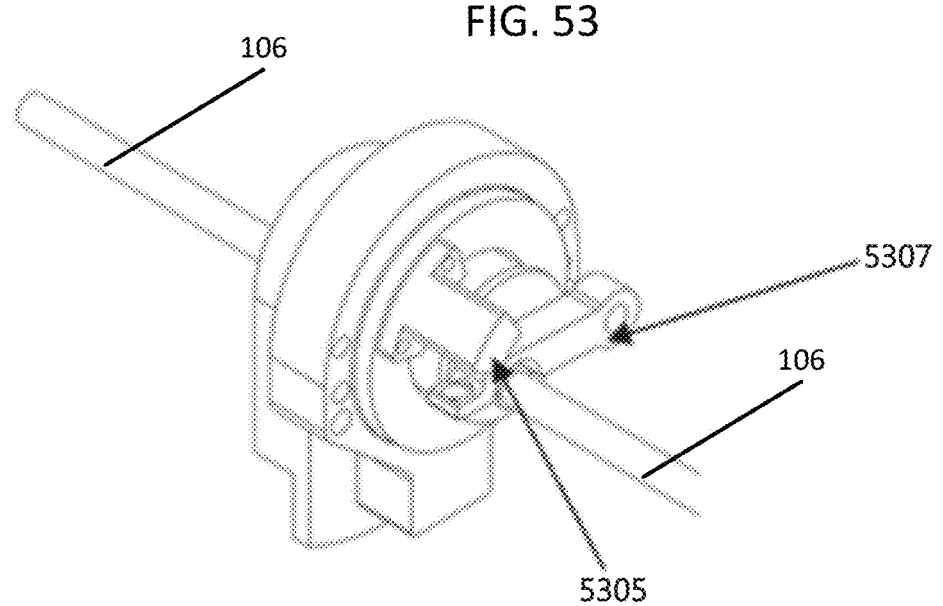

FIGS. 50 and 51 illustrate additional details of a rod feeding subassembly from a mechanical housing of a bending robot. The rod feeding subassembly may be used to feed and rotate a surgical rod 106. The feed/rotate axis may work using a differential drive assembly. A differential drive is achieved using a series of pulleys and a cable 5003. The cable 5003 is wrapped around the pulleys and a drum 5005 as shown in FIGS. 50 and 51. Rotating the drive pulleys 5001a and 5001b in the same direction rotates the drum 5005 in clockwise and counter-clockwise directions respectively. Rotating the drive pulleys in opposite directions moves the carriage 5009 forward and backward. An advantage of such a mechanism may be that both the feed and rotation of the rod is achieved using just one mechanism. The drive pulleys may be driven by respective motors 5011a and 5011b through respective gearboxes. Motors 5011a and 5011b may be provided in a motor housing. The rod 106 is passed through the drum and is held using a collar 5015. The drum rotates on the carriage, and the collar is threaded into the drum, holding the rod inside the drum.

The surgical rod 106 may need to be held firmly while bending it against the bend post and/or roller bearings. This may be achieved using a brake attached to the cutter arm 4801. The cutter arm 4801 cuts the rod when it rotates in the counter-clockwise direction and brakes the rod when it rotates in the clockwise direction. When the cutter arm 4801 rotates in the clockwise direction, it rotates the brake actuator 5305 which in turn presses the brake arm 5307 on the rod 106 resulting in a braking action.

The brake may also be also used during the feed mechanism. In order to feed the entire length of the rod the rod bender may works in the following sequence:
1. Tighten the rod 106 onto the drum 5005 using the collar 5015.
2. Feed the rod 106 into the bend subassembly/mechanism for bending operations until the carriage reaches the end of its range of motion closest to the bending subassembly.
3. Brake (e.g., brake arm and brake actuator) holds the rod 106
4. Carriage 5009 slides back on the rod 106. This can be achieved as the brake is much stronger than the holding collar.
5. Release the brake.
6. Repeat steps 2-5 as needed until rod bending operations are complete.

Stated in other words, carriage 5009 may have a limited range of motion, and an effective range of motion may be increased by sliding the carriage back on the rod (i.e., by braking the rod while sliding the carriage back to its starting position most distant from the bending subassembly.

According to additional embodiments of inventive concepts, methods may be provided to automatically bend rods using robotic processes intraoperatively, thereby saving time and effort for the surgeons, automating data acquisition, providing/maintaining sterility, and/or maintaining/retaining strength of the rods.

Some embodiments of inventive concepts may also provide methods to determine the springback in a rod of a known or unknown material intraoperatively. These methods may allow the user to put any rod in the rod bender without prior knowledge of the material/springback property of the rod.

Globus Rod Bender (GRB) systems disclosed herein may provide bending of rods (also referred to as implants or rod implants) for surgical use in patients. Prior techniques may require a surgeon to freehand transform the rod implant(s).

Freehand transforming can lead to inconsistencies in the planned bend and/or create weak points in the rod through continuous notching. GRB systems may use patient imaging from screw planning or intra-operative fluoroscopy to bend the implant using an autoclavable mechanical assembly, and the techniques used may allow the system to maintain the sterility of the implant throughout the procedure from bending to placement.

Figure 13:
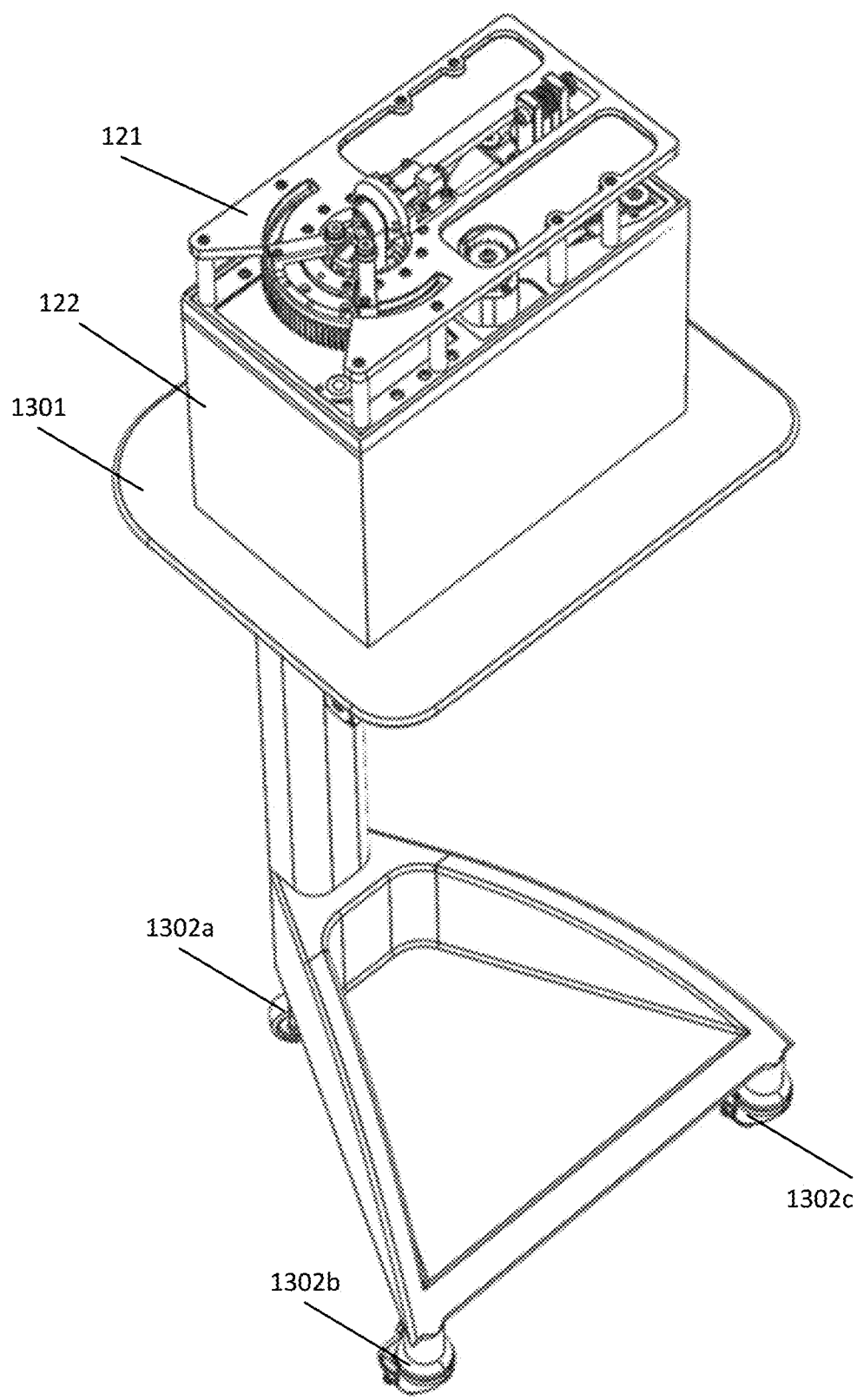
FIGS. 13 and 15 provide illustrations of a Rod Bender System without a drape according to some embodiments.
Figure 14:
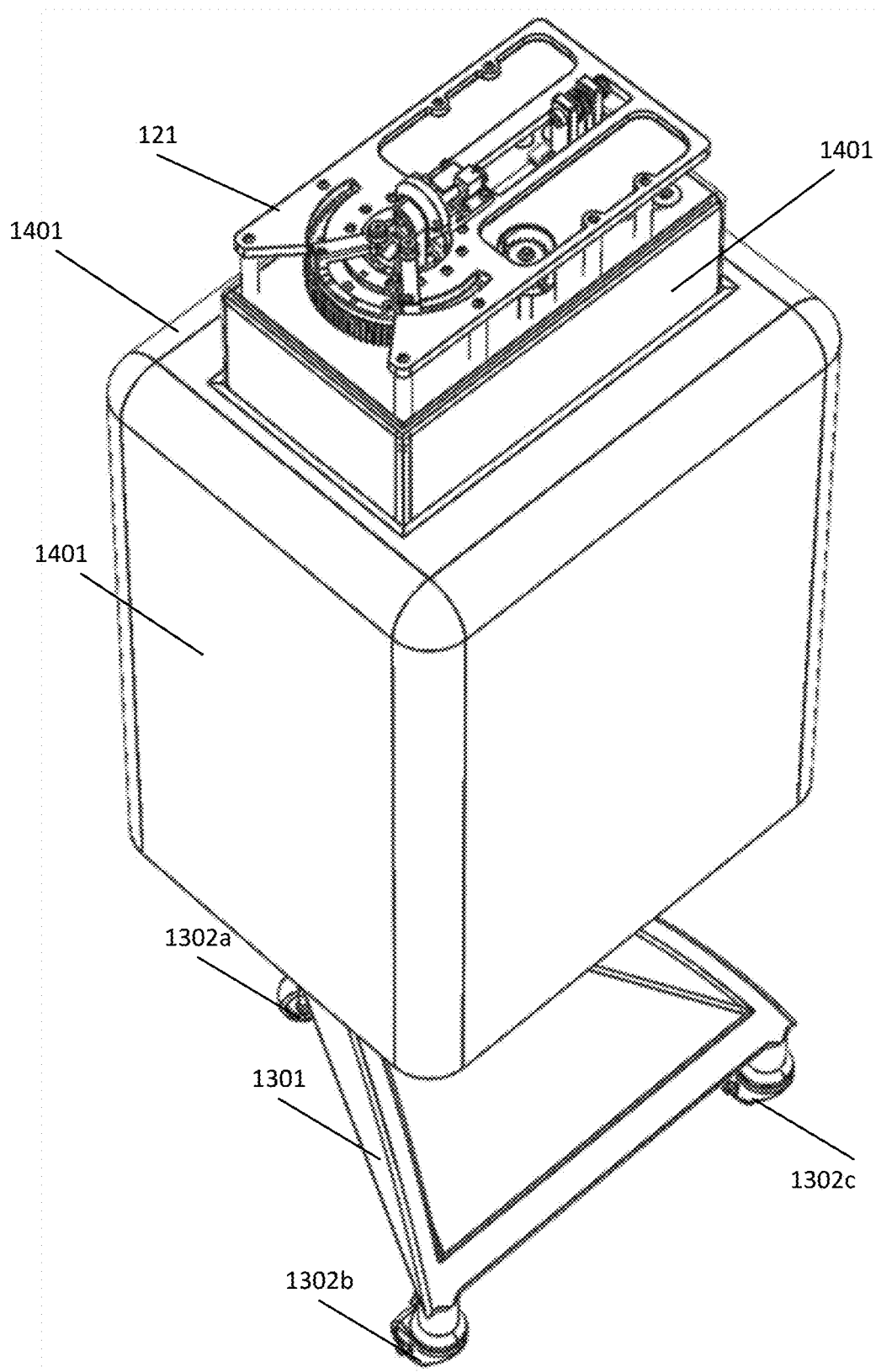
FIGS. 14 and 16 provide illustrations of a Rod Bender System with a drape according to some embodiments.

Hardware for such GRB systems may be provided as discussed herein with respect to FIGS. 13 and 14, which show the Rod Bender System without a drape.

The sterilizable rod bender system of FIG. 13 may include a cart 1301 with motor housing 122 (e.g., as shown in FIG. 3) on the cart 1301, and with mechanical housing 121 (e.g., as shown in FIG. 3) on motor housing 122. Motor housing 122 may also be referred to as an embedded motion control system and may include motors, gearboxes and other electronics. Mechanical housing 121 may also be referred to as an autoclavable top assembly and may include mechanical systems that are compatible with high temperature autoclave sterilization. FIG. 13 shows the cart 1301, motor housing 122, and mechanical housing 121 without a drape for ease of illustration. FIG. 14 shows a drape 1401 sandwiched between the mechanical housing 121 and the motor housing 122 and also covering upper portions of the cart 1301. Because the drape 1401 covers the motor housing 122 (also referred to as motion control system), the motor housing 122 is not visible in FIG. 14.

The mechanical housing 121 (also referred to as the autoclavable top assembly) does not include any electrical or electronic components that could be damaged by conventional preoperative or intraoperative sterilization techniques, such as autoclaving, high-temperature steam sterilization, chemical sterilization, etc. Accordingly, the cart 1301 and the motor housing 122 may be covered by the sterile drape 1401, while the sterile mechanical housing 121 is exposed. Cart 1301 may include wheels 1302a, 1302b, and 1302c to facilitate movement.

FIG. 14 provides illustration of the Globus Rod Bender system with the drape 1401 installed over the cart 1301 and motor housing 122.

Figure 15:
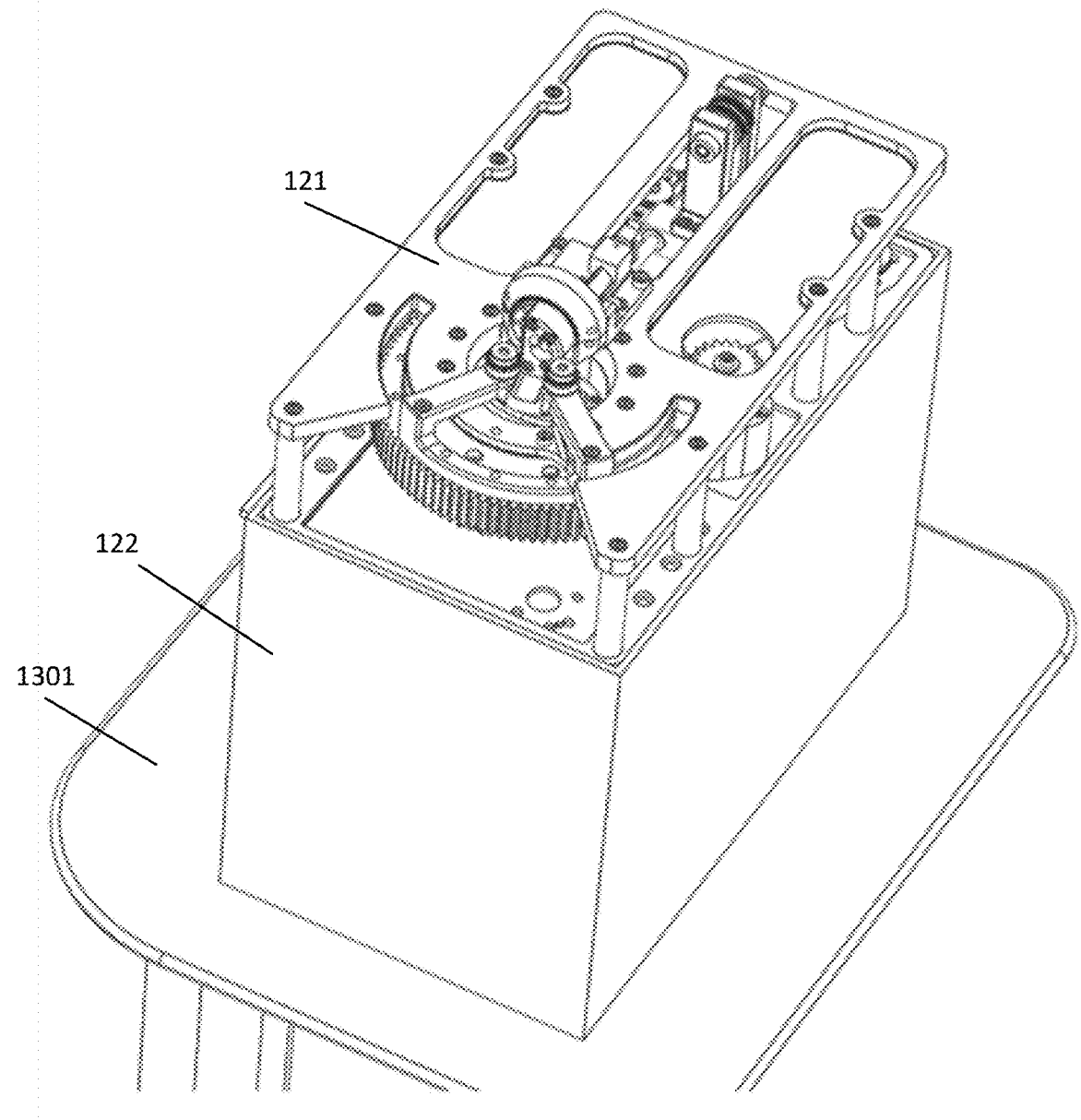
Figure 16:
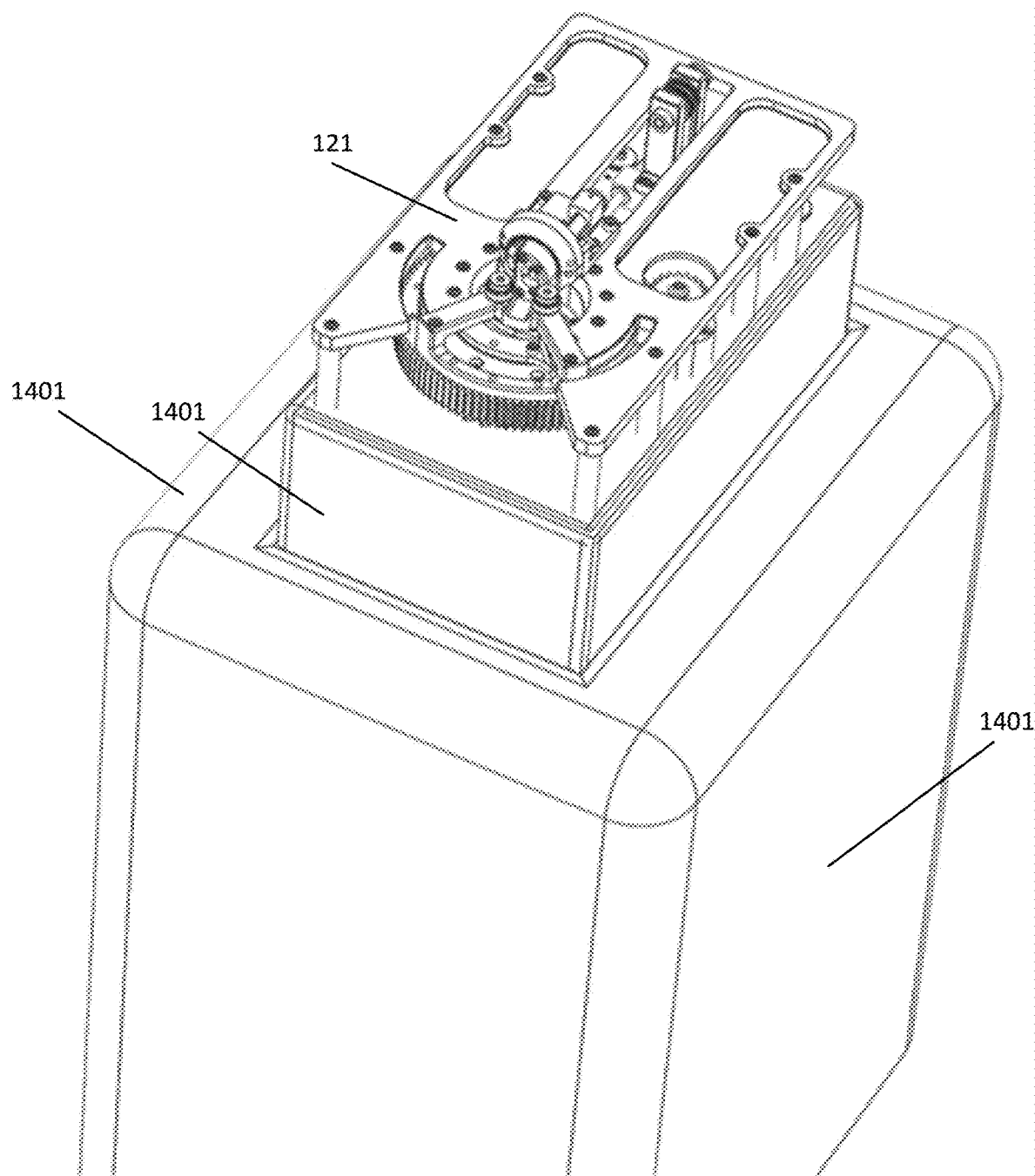

FIG. 15 illustrates an enlarged view of the rod bender system fully assembled, without the drape 1401 engaged over the cart 1301 and motor housing 122. FIG. 16 illustrates an enlarged view of the assembled rod bender system, with the drape 1401 engaged over the cart 1301 and over motor housing 122.

Figure 17:
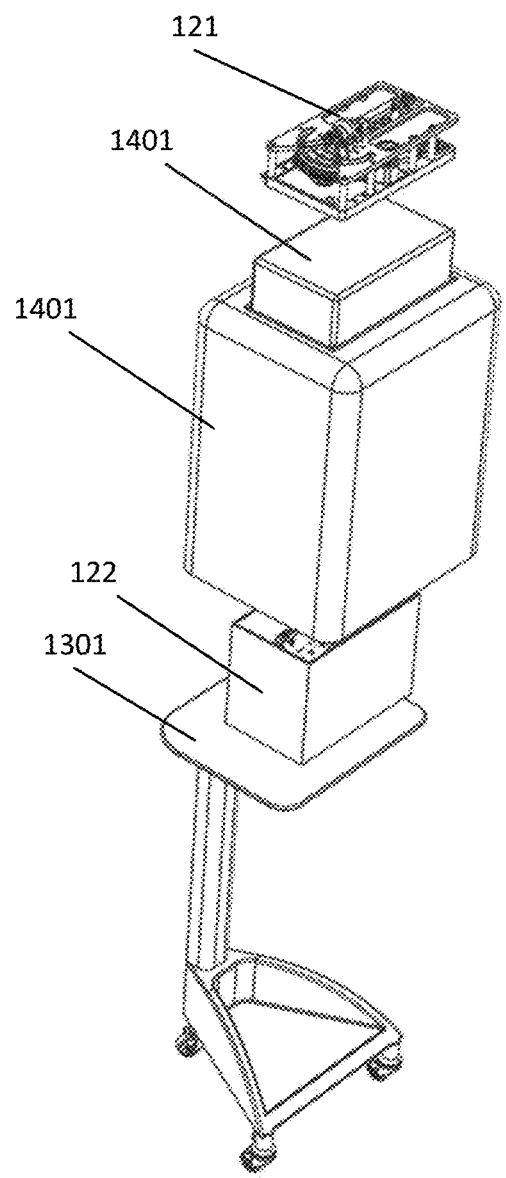
FIG. 17 illustrates an exploded view of a rod bender system according to some embodiments.

FIG. 17 illustrates an exploded view of mechanical housing 121 provided as an autoclavable top assembly, drape 1401, motor housing 122, and cart 1301 with an embedded motion control system included in motor housing 122.

The engagement between the mechanical housing 121 (provided as an autoclavable top assembly) and the motor housing 122 with embedded motion control system may work as follows. The mechanical housing 121 may have shafts (also referred to as transmission outputs) with rotary seals. Rotary seals (e.g., radial shaft seals) may be used to seal rotary elements, such as a shaft or rotating bores against fluids, dust, dirt etc. The rotary seals create a barrier between surfaces while allowing for rotary motion transfer. According to some embodiments, there may be four shafts (also referred to as transmission outputs) protruding from (or receiving elements on) the bottom of the mechanical housing 121 to facilitate bending (e.g., bending transmission output of FIG. 3), braking and/or cutting (e.g., brake transmission output 170 of FIG. 3), and feeding and/or rotating the rod (e.g., first and second pulley transmission outputs 164 and 166 of FIG. 3, also referred to as rod feeding/rotating transmission outputs). The bottom surface of the mechanical housing 121 (also referred to as a top mechanical assembly) does not have any other holes and may be completely sealed as shown in in FIG. 21.

Figure 22:
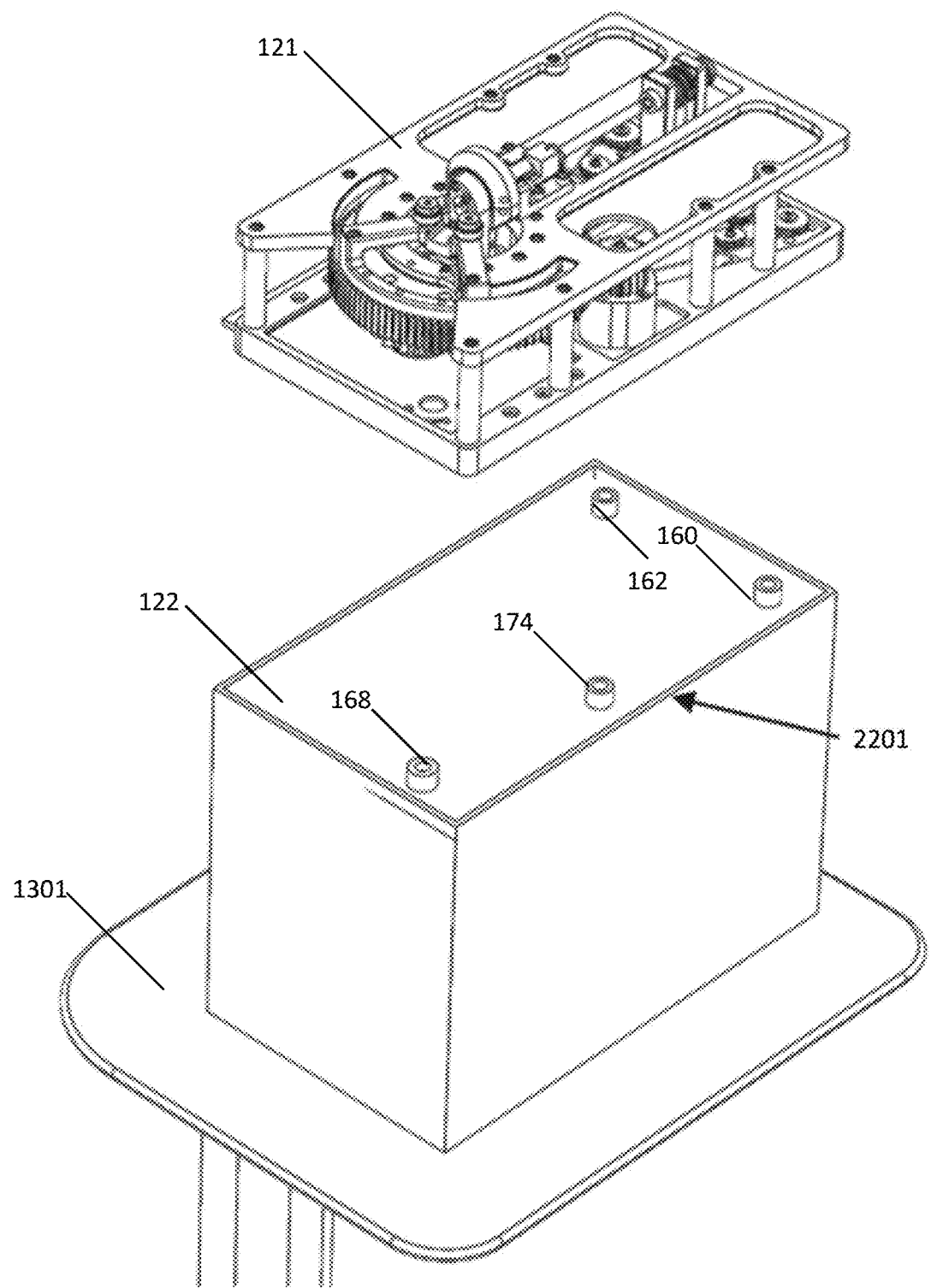
FIG. 22 illustrates a top surface of a motor housing dissembled from a mechanical housing according to some embodiments.

A bottom surface of mechanical housing 121 engages with a top surface of motor housing 122 through the drape 1401 and a gasket 2201 on an outer edge of the motor housing 122 embedded in the cart 1301. As shown in FIG. 22, the motor housing 121 embedded on the cart may have 4-shafts (also referred to as transmission inputs) 160, 162, 168, and 174 coming out from the top. According to some embodiments, the four shafts may facilitate bending (e.g., bending transmission input 174 of FIG. 3 corresponding to bending transmission output 176), braking and/or cutting (e.g., brake transmission input 168 of FIG. 3 corresponding to brake transmission output 170), and feeding and/or rotating the rod (e.g., first and second pully transmission inputs 160 and 162 of FIG. 3, also referred to as rod feeding/rotating transmission inputs, corresponding to first and second pully transmission outputs 164 and 166). The shaft housings accommodate for parallel and angular misalignment. The shafts coming out of the top of mechanical housing 121 engage with the shaft housings in the bottom motor housing 122 to facilitate motion transfer from the motors embedded in the motor housing 122 to the mechanisms on the top mechanical assembly 121. The engagement mechanism can be chosen from a plurality of mechanisms including splines, gears, clutches, and other couplings.

The type of engagement between the top plate and bottom plate shafts may be the same or different for all the axes, for example, based on the radial, axial and moment load. This engagement may provide the following characteristics:
 1. Self-centering;
 2. Indexing accuracy; and/or
 3. Capability to handle parallel, angular or combined misalignments.

Figure 18C:
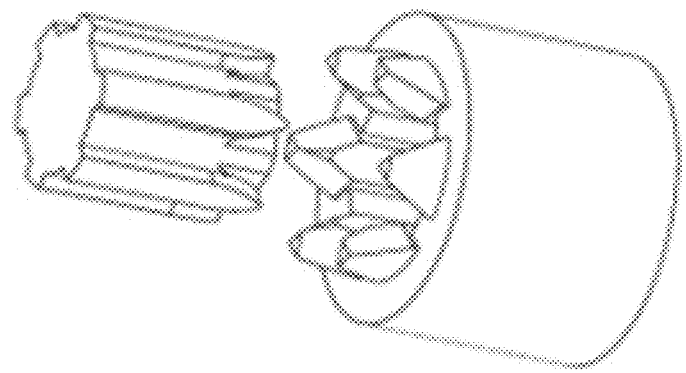
FIGS. 18A, 18B, and 18C illustrate examples of mechanical couplings between mechanical and motor housings according to some embodiments.
Figure 18B:
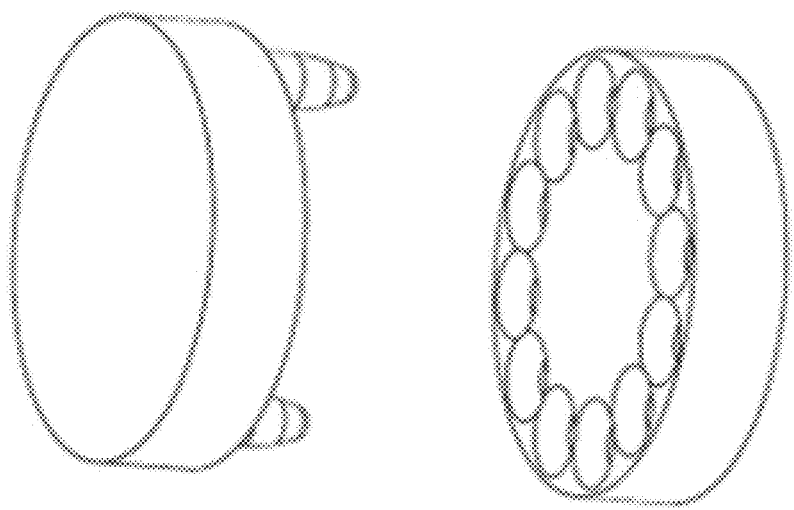
Figure 18A:
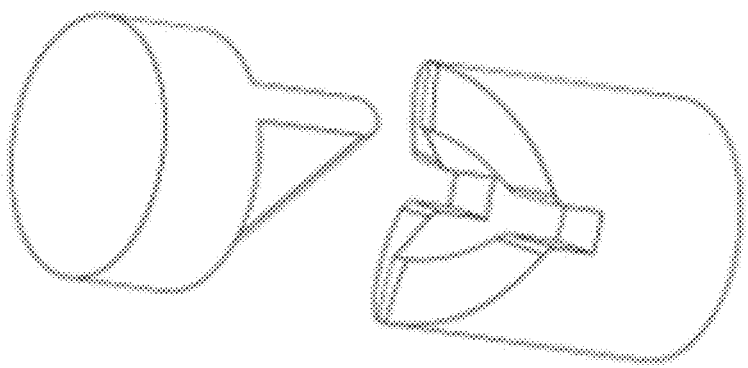

FIGS. 18A, 18B, and 18C show examples of self-indexing couplings for the rod bender between the mechanical housing 121 and the motor housing 122. According to some embodiments, a top coupling structure of FIG. 18A may be provided for each of bending transmission output 176, brake transmission output 170, first pully transmission output 164, and second pully transmission output 166, and a bottom coupling structure of FIG. 18A may be provided for each of bending transmission input 174, brake transmission input 168, first pully transmission input 160, and second pully transmission input 162 (or vice versa). According to some other embodiments, a top coupling structure of FIG. 18B may be provided for each of bending transmission output 176, brake transmission output 170, first pully transmission output 164, and second pully transmission output 166, and a bottom coupling structure of FIG. 18B may be provided for each of bending transmission input 174, brake transmission input 168, first pully transmission input 160, and second pully transmission input 162 (or vice versa). According to still other embodiments, a top coupling structure of FIG. 18C may be provided for each of bending transmission output 176, brake transmission output 170, first pully transmission output 164, and second pully transmission output 166, and a bottom coupling structure of FIG. 18C may be provided for each of bending transmission input 174, brake transmission input 168, first pully transmission input 160, and second pully transmission input 162 (or vice versa). According to some other embodiments, a different coupling types may be used for different couplings (e.g., one of the coupling types from FIGS. 18A (flat head and corresponding slot), 18B (pin and slot), or 18C (male and female splines) may be used to provide couplings between first/second pully transmission outputs and first and second pully transmission inputs, and another of the coupling types from FIGS. 18A, 18B, or 18C may be used to provide coupling between bending transmission output and bending transmission input and/or between brake transmission output and brake transmission input.

Figure 19:
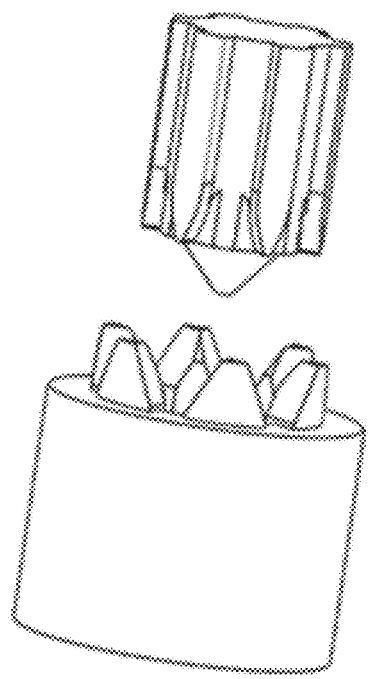
FIG. 19 illustrates an example of a mechanical coupling providing self-centering according to some embodiments.

As can be seen in FIGS. 18A, 18B, and 18C, each of the couplings may have a capability of self-indexing. One way to achieve self-centering is to add a central projection to the center of top shafts (analogous to a live center in a lathe machine) as shown, for example, in FIG. 19 (which illustrates a modification of the coupling of FIG. 18C), with a corresponding central depression of the opposing shafts. A central projection may be similarly added to couplings of FIG. 18A and/or 18B. FIG. 19 shows an example how self-centering can be achieved using a spline shaft with a central projection. While the central projection is discussed with respect to the top shaft(s), the central projection may be instead be provided on the bottom shaft with a corresponding central depression on the top shaft. The central projection, for example, may be cone shaped, e.g., conical, paraboloidal, etc., and the corresponding depression may have a shape matching that of the central projection.

Figure 20:
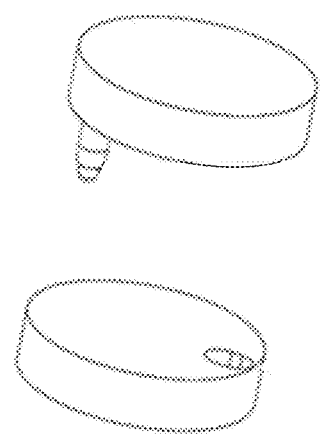
FIG. 20 illustrates a pin that can be used to lock a mechanical coupling according to some embodiments.

Another method to engage the shafts of top plate and bottom plate is illustrated in FIG. 20. As shown in FIG. 20, a spring controlled pin can be placed on the top plate shaft and can be pressed against the bottom plate shaft. If the pin does not fall within the slot, the spring will be compressed. Once the motor starts rotating and the pin falls within the area of the slot, the spring is relaxed and both the shafts start rotating together in order to accomplish motion transfer from the bottom plate to the top plate. FIG. 18B shows an embodiment with two such pins that can be spring controlled as discussed above with respect to FIG. 20.

Figure 21:
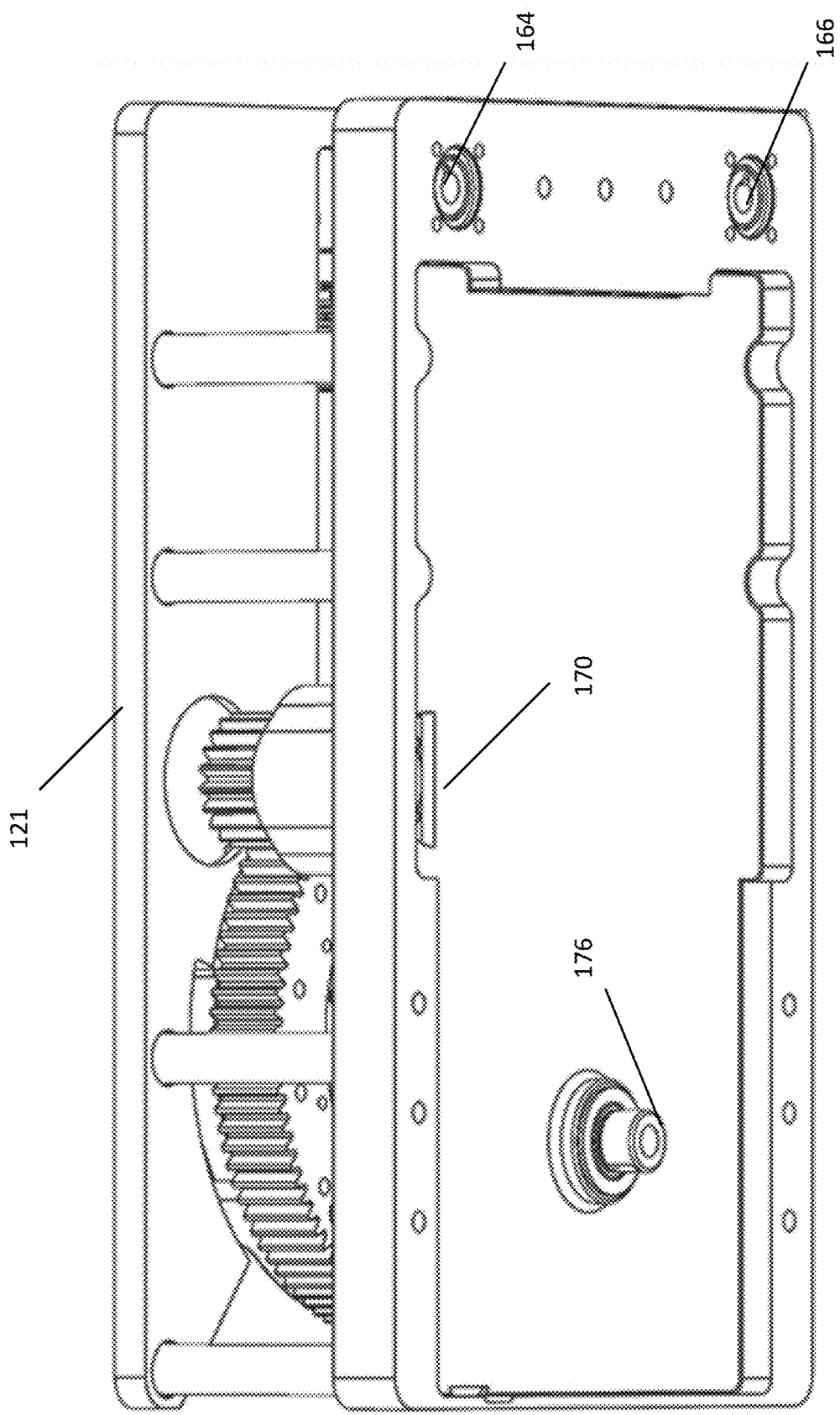
FIG. 21 illustrates a bottom surface of a mechanical housing according to some embodiments.

FIG. 21 illustrates a bottom surface of the mechanical housing 121 including bending transmission output 176, brake transmission output 170, first pully transmission output 164, and second pully transmission output 166.

FIG. 22 shows the cart 1301 with embedded motor housing 122 (Drape not shown) and with mechanical housing 121 pulled away. As shown in FIG. 22, bending transmission input 174, brake transmission input 168, first pully transmission input 160, and second pully transmission input 162 may extend from a top surface of motor housing 122.

Figure 23:
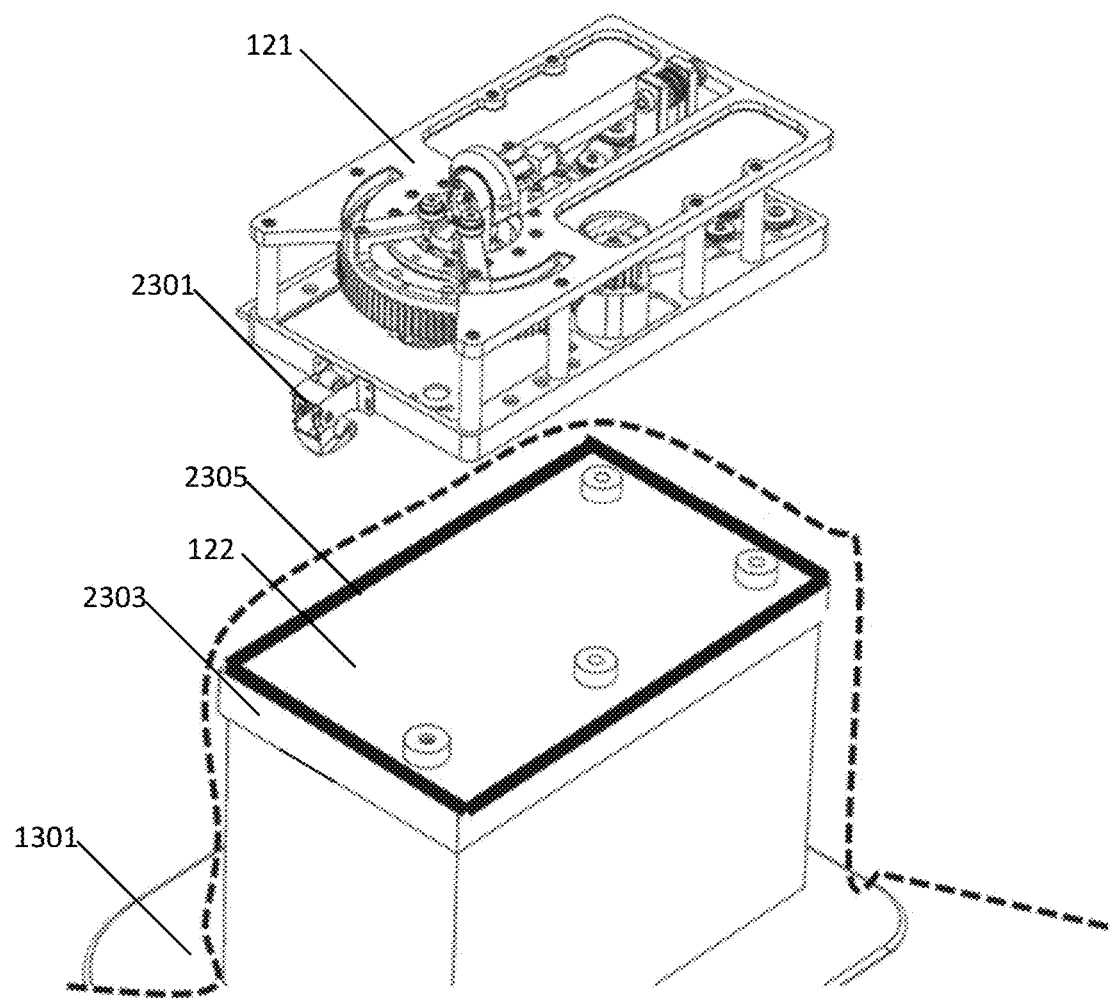
FIG. 23 illustrates an exploded view of a rod bender system according to some embodiments.

Steps of engagement are discussed below with respect to FIG. 23 which shows an exploded view of the components of the sterilizable rod bender. The top autoclavable mechanical housing 121 may include multiple roller latches 2301 as shown. The cart/motor mount has a movable engagement plate 2303 with a gasket 2305. Once the mechanical housing 121 is placed on the movable engagement plate 2303 and the roller latches 2301 (also referred to as roller ratchets) are engaged, the gasket 2305 is compressed and the mechanical housing 121 is sealed from the motor housing 122. In alternative embodiments, the gasket 2305 may be provided on the top (non-moving) surface of motor housing 122 or the bottom surface of mechanical housing 121. The gasket 2305 may provide a two-fold functionality, that is: providing a seal between motor and mechanical housings 122 and 121 and/or providing that the drape is softly held between a rigid surface and a flexible surface to provide that the drape does not tear with axial or shear loads. Then, the mechanical housing 121 is pushed down which enables the shafts to be engaged with the shaft housings by pushing/puncturing through the drape. Given that the mechanical housing 121 first seals on the gasket and the shafts have rotary seals on them, the sterility may be preserved throughout the assembly procedure.

Figure 24:
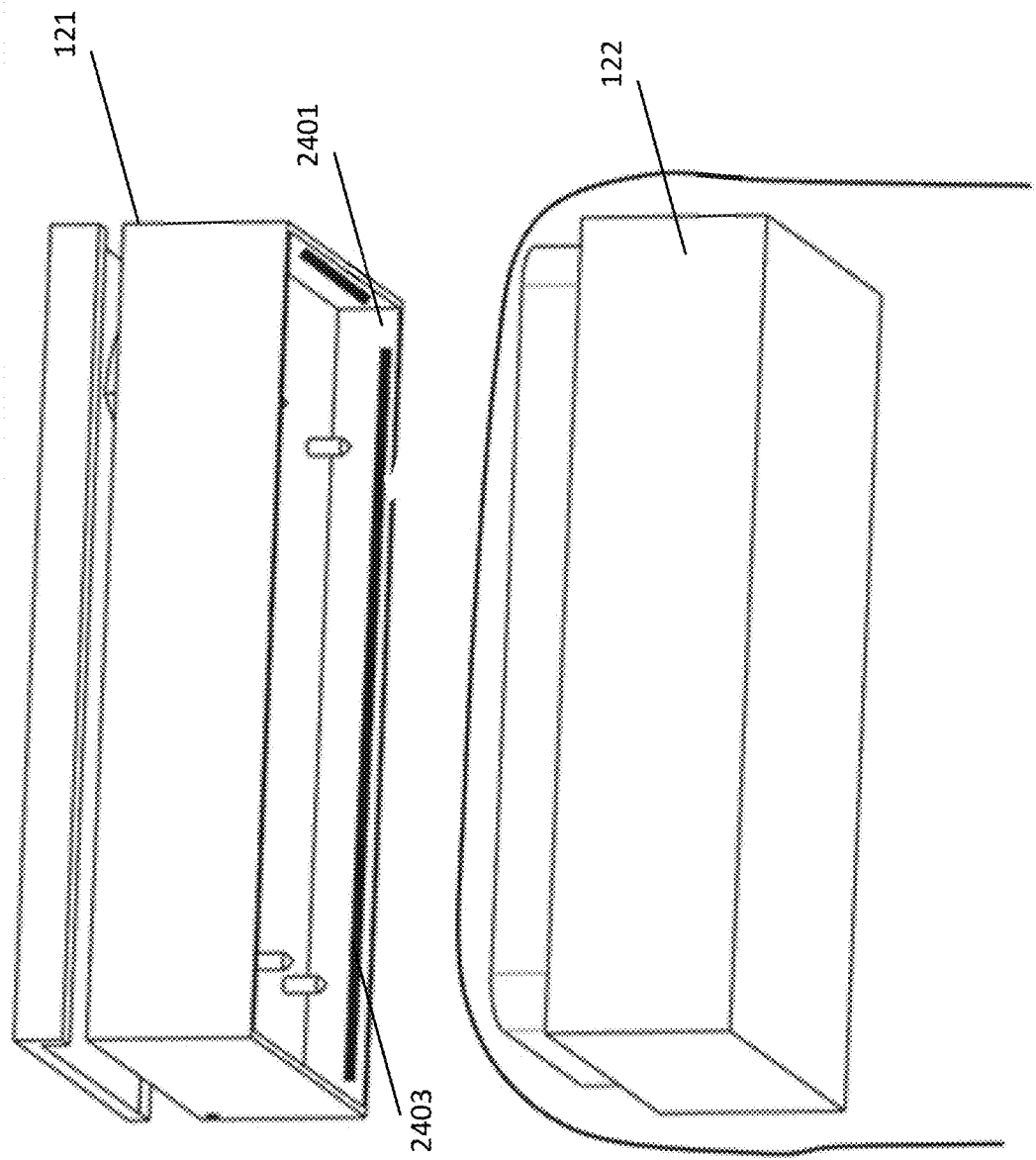
FIG. 24 illustrates a sterile mechanical housing with a flange and internal side gasket according to some embodiments.

In another embodiment of FIG. 24, the mechanical housing 121 may have a flange 2401 with an internal gasket 2403 to facilitate a seal between the mechanical housing 121 and the motor housing 122 after assembly. The gasket 2403 can also serve as a tensioner to provide that the drape is pulled down along with the top plate prior to drape puncture and shaft engagement.

Figure 25:
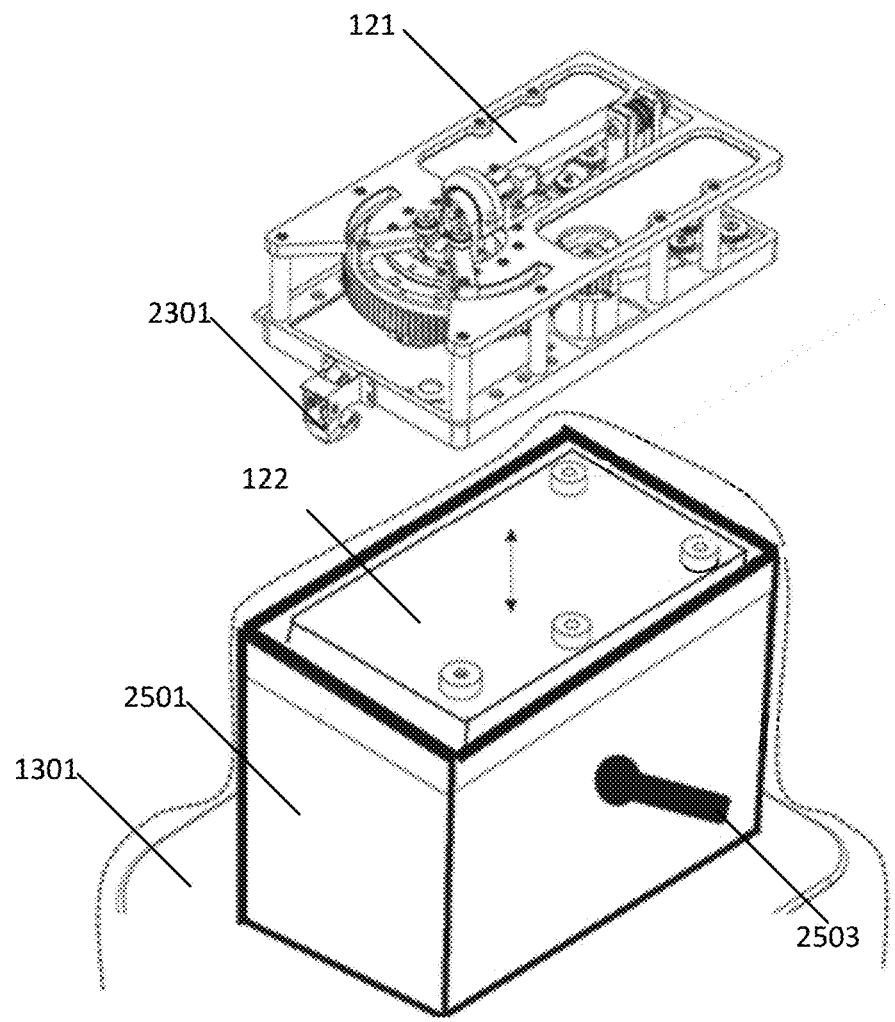
FIG. 25 illustrates a rod bender system providing engagement between mechanical and motor housings using a locking mechanism according to some embodiments.

An alternative way to engage the shafts in the mechanical and motor housings 121 and 122 is to place the motor housing on a linear rail and actuate it (up and down), for example, using a cam controlled with a manual lever arm 2503 as shown in FIG. 25 or a motor. The motor housing 122 may be housed inside a stationary bottom box 2501 and may be actuated up and down, for example, using a lead screw, a cam mechanism, and/or a motor.

Operation for embodiments of FIG. 25 are discussed below.

The mechanical housing 121 is placed on the bottom box 2501 and latches 2301 are closed. This provides that the mechanical housing 121 is sealed on the bottom box 2501.

The lever arm 2503 is rotated manually, which raises the motor housing 122. The motor housing 122 may have the bottom shafts shaped analogous to die cutters to facilitate the cutting of the drape where the upper and lower shafts meet. This leads the shafts of the motor housing 122 to push through the drape and engage with the shafts in the mechanical housing 121. The motor housing 122 can be locked in this raised position. After the functionality of the rod bender has been achieved, the lever arm 2503 can disengage the motor housing 122 from the mechanical housing 121.

Figure 26:
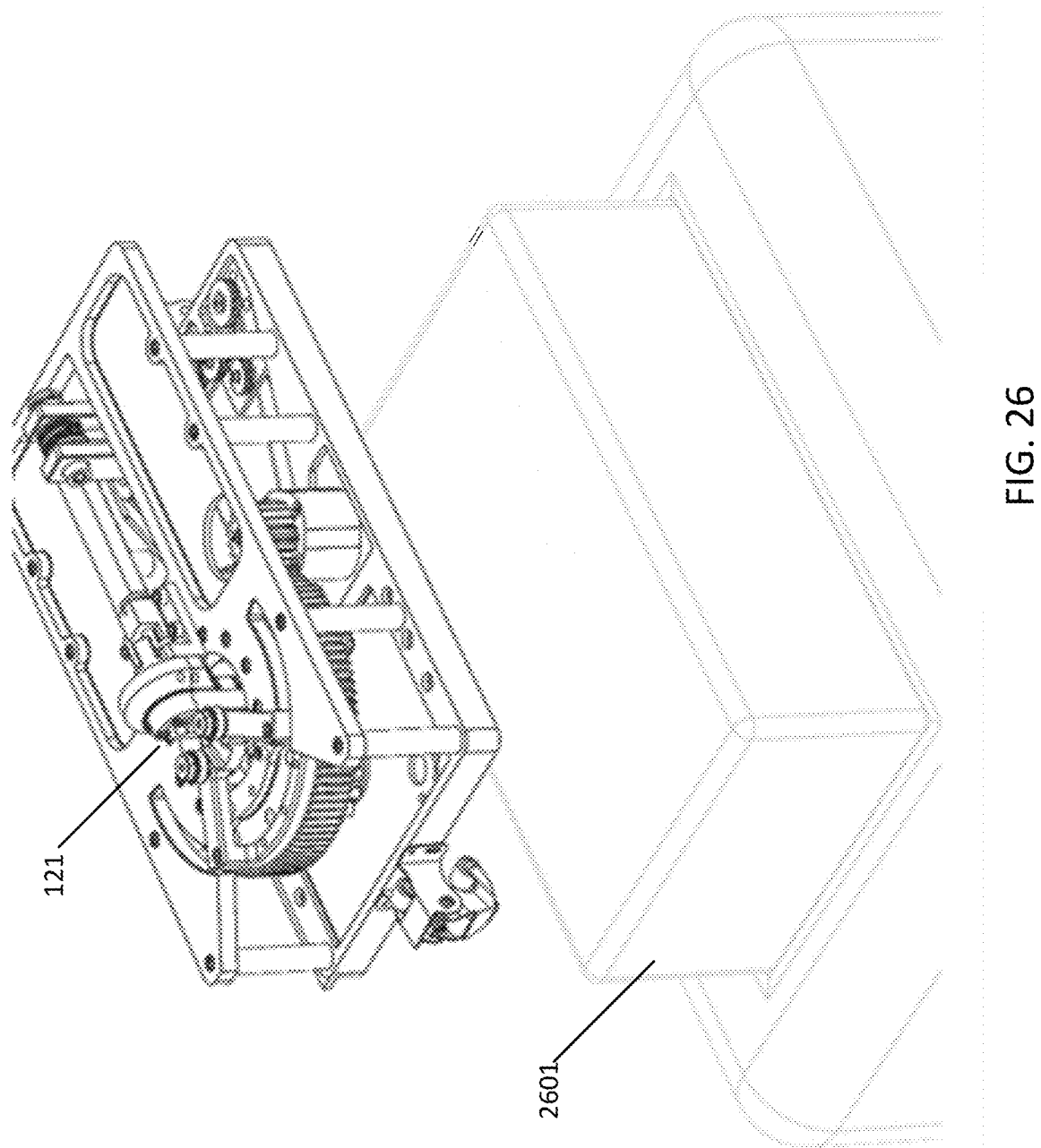
FIG. 26 illustrates a rod bender system with a fenestrated drape according to some embodiments.

An alternative to pushing/puncturing through the drape is to have a peelable drape 2601 where the shown portion (on top of motor housing 122) in FIG. 26 can have a peel-able top to allow the shafts to engage through the peeled window. Fenestrated drapes can be used for this purpose. Such a design may omit a movable engagement plate.

Some embodiments of inventive concepts may provide intraoperative Springback measurement. Bending rods intraoperatively may require knowledge of spring back on the rod in order to bend the rod accurately to a predetermined position. Springback refers to the change in the angle of the rod after it has been released from the bending load. It might be cumbersome to input the material properties of each rod that can potentially be bent by the intraoperative rod bender.

Figure 27:
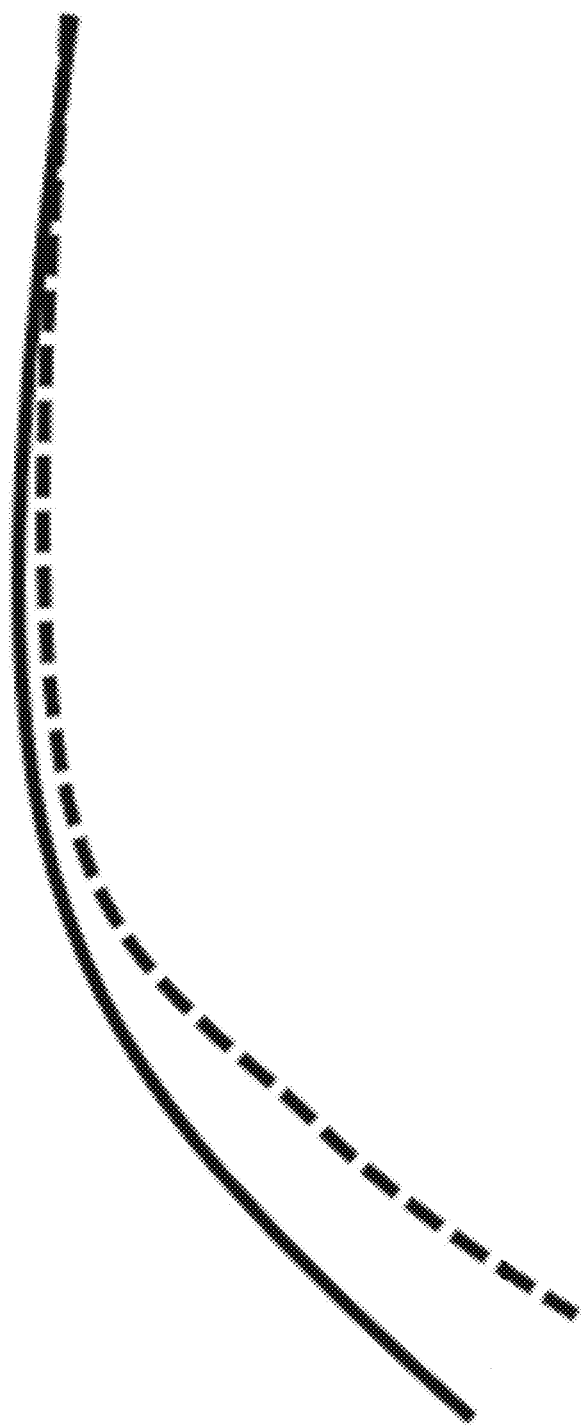
FIG. 27 illustrates springback in a rod after bending according to some embodiments.

As shown in FIG. 27, the change in the angle of the rod while bending can lead to erroneous results during bending. In FIG. 27, the dashed line indicates a desired bend position to which the rod bender may bend the rod, and the solid line indicates an actual bend position (or springback position) to which the rod returns after the bending force is released from the rod. To achieve the desired bend position, the rod bender may thus need to bend the rod past the desired bend position to compensate for the springback.

Figure 28:
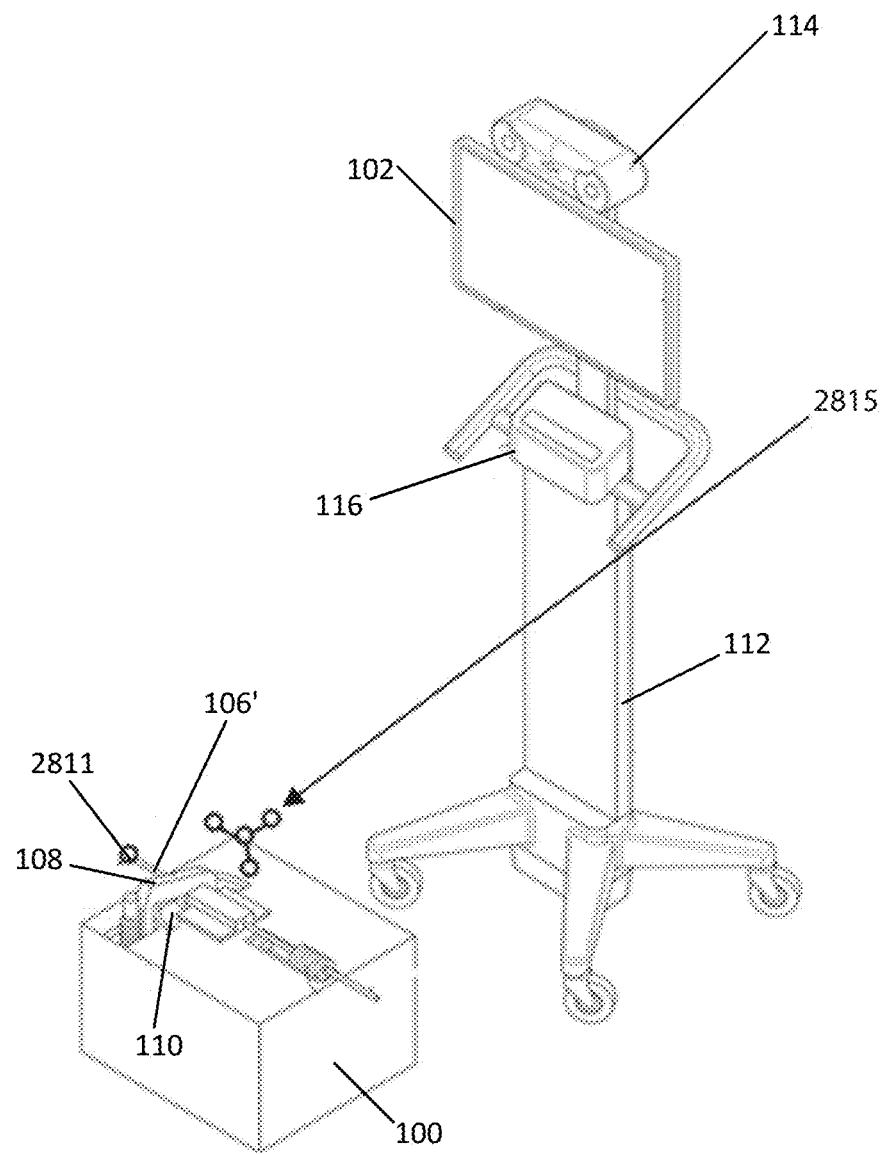
FIG. 28 illustrates a rod bender system configured to determine springback for a rod according to some embodiment.

Hence, methods of the following embodiments may provide ways to determine the springback as a function of angle for a rod of any material. FIG. 28 illustrates an example of a setup of the rod bending system that may be used to determine springback characteristics (e.g., by determining a springback equation) using a sacrificial rod 106'.

The sacrificial rod 106' end can have a detachable reflective marker 2811 (also referred to as a reflective sphere), which can be tracked in three-dimensional (3D) space using intraoperative camera 114. The camera 114 can be used to determine the position of the reflective marker 2811 on the sacrificial rod 106' with respect to a known reflective marker array 2815 (also referred to as a tracking array) placed on the rod bending robot 100. The tracking array 2815 may include at least three reflective markers in a known orientation with respect to the bending robot to allow controller 102 to determine both a position and orientation of bending robot 100 and components thereof. The rod bending robot 100 may need to bend the end of the sacrificial rod 106' to a known angle and once the rod bending robot 100 releases the load on sacrificial the rod 106', the controller 102 and camera 114 can monitor the springback. This may need to occur for two data points (e.g., for two different bend angles) for the rod as discussed below with respect to FIG. 28 to determine springback characteristics of the rod over a range of bend angles (e.g., using a springback equation).

The springback equation for any material can be approximated to a straight line and hence the two different data points for springback on the rod can be used to determine an equation for the material properties of the rod. The two data points can be obtained by choosing two different bend angles at two different positions on the rod and calculating the corresponding springback for each bend angle using the camera 114. This equation can be used to bend the surgical rod 106 accurately to the required position without having prior knowledge regarding the material of the surgical rod. For example, a sacrificial rod may be provided with the surgical rod where the sacrificial and surgical rods were manufactured together so that both have the same characteristics (e.g., the same diameter, the same material, the same springback characteristics, etc.). Accordingly, springback characteristics of the sacrificial and surgical rods will be the same, and a springback equation developed using the sacrificial rod can be used to accurately bend the surgical rod. The bending system 10 can thus bend the sacrificial rod to two different angles at two different points to determine the springback equation that is used to bend the surgical rod.

According to some other embodiments, the spring back equation may be determined by monitoring motor current for the motor used to bend the rod (e.g., bending actuator motor 172).

In such embodiments, the following operations may be performed.

A load may be applied on the sacrificial rod 106' using the bend rotor (e.g., using bending actuator motor 172 to rotate bending actuator 150) and bend the sacrificial rod 106' to the desired bend angle.

The bend rotor may be rotated back to its original position so as to release the sacrificial rod 106' from bend load.

The sacrificial rod 106' will undergo a springback once the bend rotor stops contacting the sacrificial rod 106'.

Then, the bend rotor may be rotated back until it touches the sacrificial rod 106'. This can be determined by monitoring the motor current as there will be a slight spike in motor current (e.g., current to the bending actuator motor 172) when the bend rotor touches the sacrificial rod 106'. This is the position of the sacrificial rod 106' after the springback. The angular difference between the two points indicates the springback.

The above process may need to be repeated at a second position on the sacrificial rod 106' for a different bend angle.

Using two springback data points, the springback equation for the sacrificial rod 106' can be calculated and the surgical rod 106 can then be bent accurately using the springback equation determined using the sacrificial rod 106' without requiring any prior knowledge of material properties of the surgical rod 106.

Because the sacrificial and surgical rods may be produced together in a same batch, lot, etc., the springback characteristics of the two may be the substantially the same and/or identical. Accurate calibration of the rod bender may thus be provided for each surgical rod based on actual characteristics of that rod. Accordingly, accuracy of bending may be substantially unaffected by different characteristics of rods produced in different batches, lots, etc.

Intraoperative transformation point capture is discussed below according to some embodiments of inventive concepts.

The GRB software provides ways to shape a surgical implant device (e.g., rod) based on captured transformation points. These points may be captured using a probe including a probe handle that has an array which can be optically tracked using the camera 114 and a probe tip that attaches to the handle and that fits into a screw or that is used to locate where a rod will be placed. The handle includes its array which is tracked and also an additional moveable stray marker as discussed below with respect to FIGS. 29A and 29B.

FIGS. 29A and 29B illustrate embodiments of rod bender capture probe tip/handle assemblies according to some embodiments.

Figures 30A, 30B:
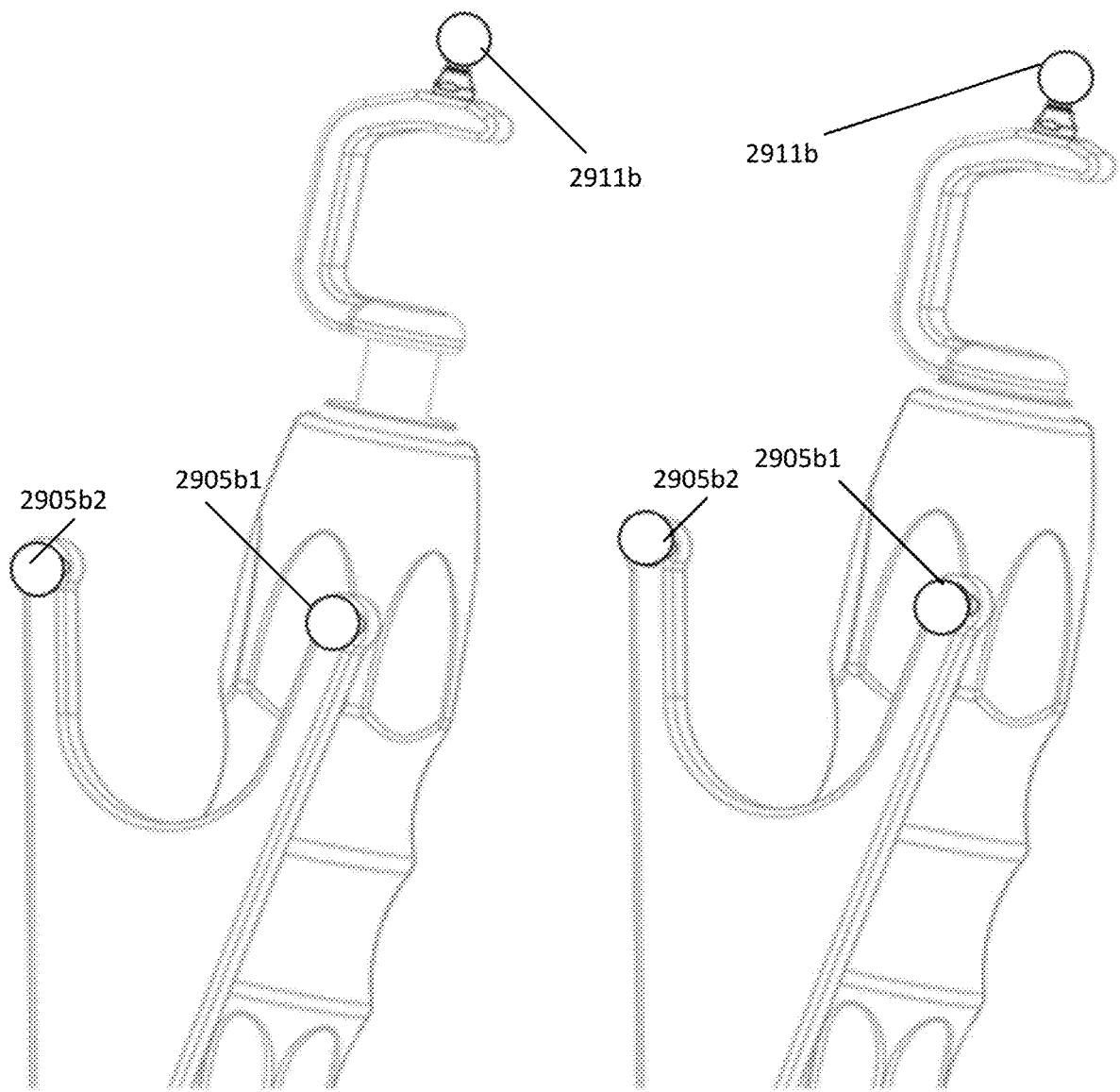
FIGS. 30A and 30B illustrate examples of a rod bender capture probe tip/handle assembly including a stray marker according to some embodiments.

In FIG. 29A, the probe 2901a includes a probe tip 2907a and a tracking array 2903a with fixed markers 2905a1, 2905a2, 2905a3, and 2905a4 and a moveable/stray marker 2911a. The fixed markers are fixed relative to each other and relative to the probe tip 2907a so that a position and orientation of probe tip 2907a may be determined using camera 114 to determine positions of the fixed markers in three dimensional space and to thereby determine the position and orientation of the probe tip 2907a in the three dimensional space. The moveable stray marker 2911a may be used to signal that the probe tip is in the position to be captured by the surgeon pressing the plunger so that the stray marker 2911a moves relative to the fixed markers. Upon detecting motion of stray marker 2911a, controller 102 may determine the position and orientation of probe tip 2907a and this position/orientation may be recorded as a transformation point. The stray marker 2911a can be actuated by a finger or thumb movement along a defined path in relation to the array 2903a. When the stray marker 2911a is moved (pressed) the system knows to capture the transformation point at the location of the probe tip 2907a. In FIG. 29B, the probe 2901b includes a probe tip 2907b, a tracking array 2903b (with fixed markers 2905b1, 2905b2, 2905b3, and 2905b4), and a moveable/stray marker 2911b. The fixed markers are fixed relative to each other and relative to the probe tip 2907b so that a position and orientation of probe tip 2907b may be determined using camera 114 to determine positions of the fixed markers in three dimensional space and to thereby determine the position and orientation of the probe tip 2907b in three dimensional space. The moveable stray marker 2911b may be used to signal that the probe tip is in the position to be captured by the surgeon pressing the plunger so that the stray marker 2911b moves relative to the fixed markers. Upon detecting motion of stray marker 2911b, controller 102 may determine the position and orientation of probe tip 2907b as a transformation point. This stray marker 2911b can be actuated by a finger or thumb movement along a defined path in relation to the array 2903b. When the stray marker 2917b is moved (pressed) the system knows to capture the transformation point at the location of the probe tip 2907b. If the array is able to rotate around the axis of the handle as shown in FIG. 29B, the stray marker 2917b will still be in the same position because it is in line with the axis of the handle. This embodiment of FIG. 29B is shown in greater detail in FIGS. 30A and 30B. In FIG. 30A, the plunger is in an initial extended position, and in FIG. 30B, the plunger has been depressed to indicated that the position and orientation of the probe tip 2907*b* should be captured as a transformation point.

Figure 31A:
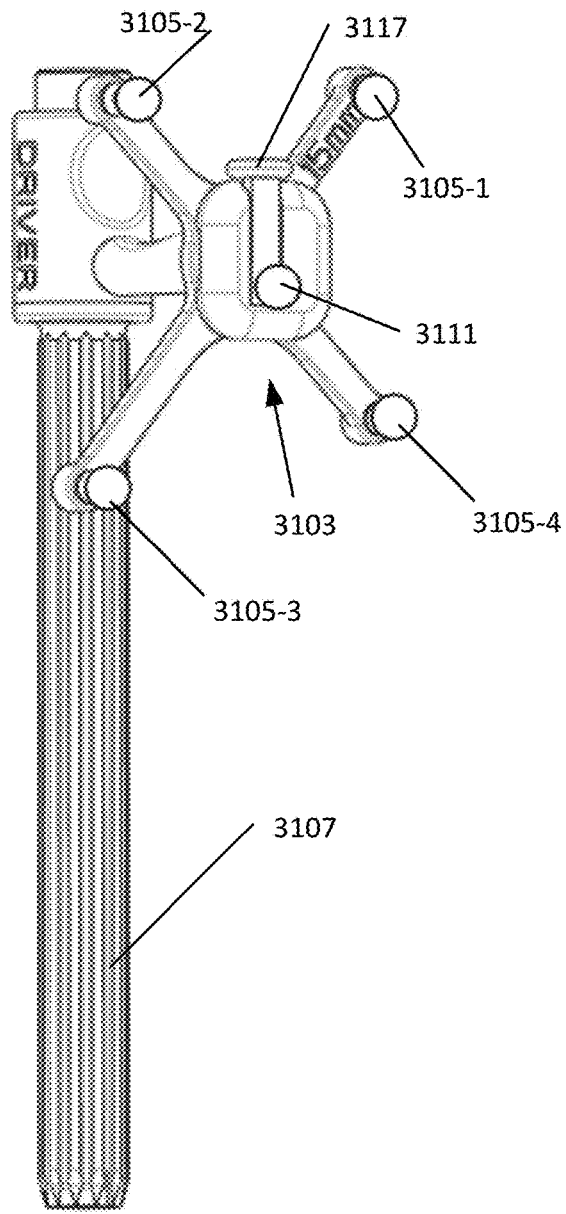
FIGS. 31A and 31B illustrate examples of a rod bender capture probe tip/handle assembly including a stray marker according to some other embodiments.
Figure 31B:
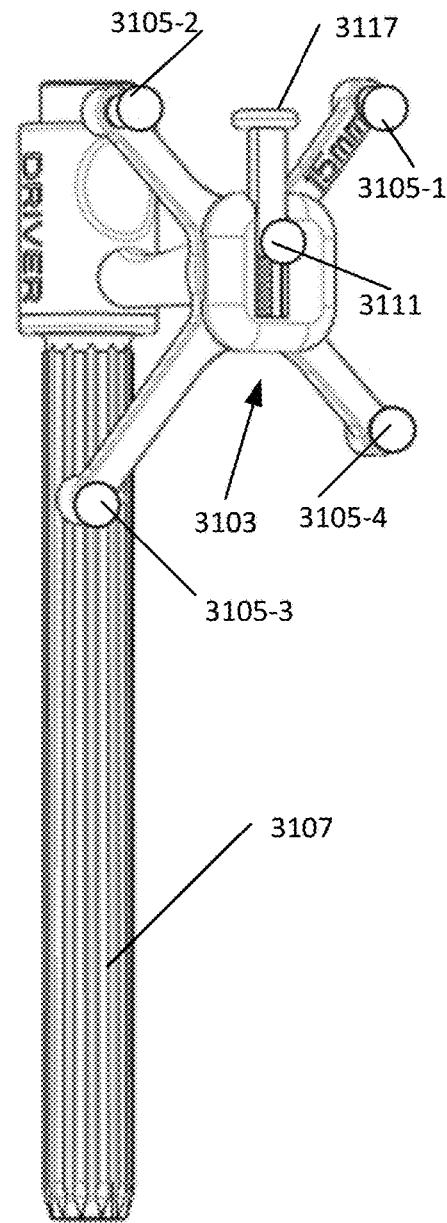

It is also possible to have a different type of stray marker that clips onto an array. Such a detachable stray marker may allow any probe or instrument with an array to capture a specific tool location and orientation via the movement of a specific stray marker. FIGS. 31A and 31B illustrate a stray marker 3111 attached to the center of a face of array 3103 including fixed markers 3105-1, 3105-2, 3105-3, and 3105-4. When the button 3117 is pressed, the probe tip location and orientation can be captured.

The Probe tip may be made to interface with a screw or other rod holding implant, so that when the probe tip is engaged with a compatible screw a precise location and orientation of the screw/head can be determined. As shown in FIG. 32D, for example, a spinal implant screw 3251 may have a threads 3257 configured to secure the screw into bone and a tulip head 3255 configured to receive a surgical rod 106. The tulip head 3255 may have a U-shaped recess 3259 configured to receive the surgical rod 106 and a threaded recess configured to receive a locking cap 3261 to lock the rod into place. Locking cap 3261, for example, may be threaded to screw into an upper portion of the tulip head 3255 after placing the rod.

Figures 32A, 32B, 32C:
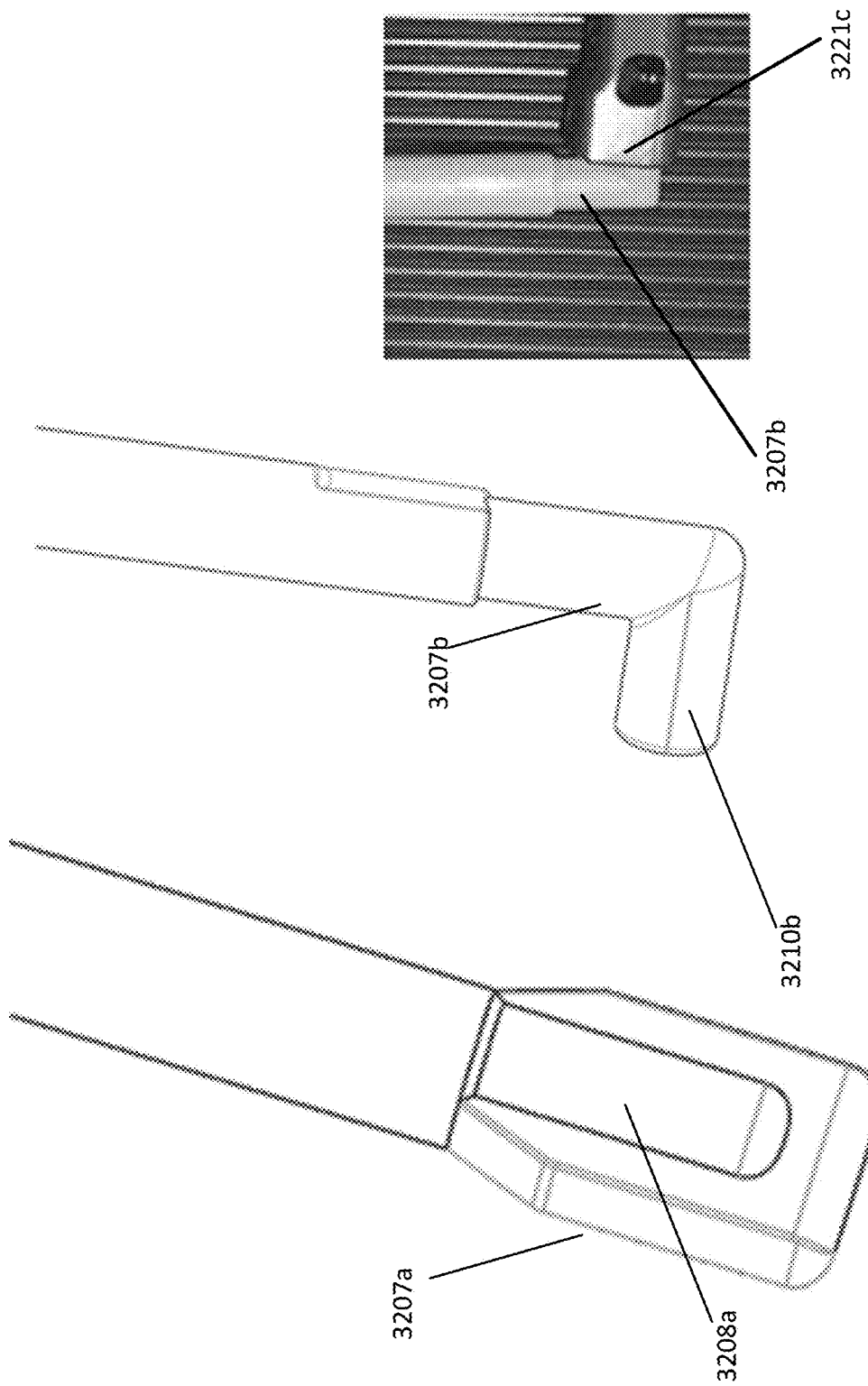
FIGS. 32A, 32B, and 32C illustrate examples of probe tips that interface with instruments such as the spinal screw of FIG. 32D according to some embodiments.
Figure 32D:
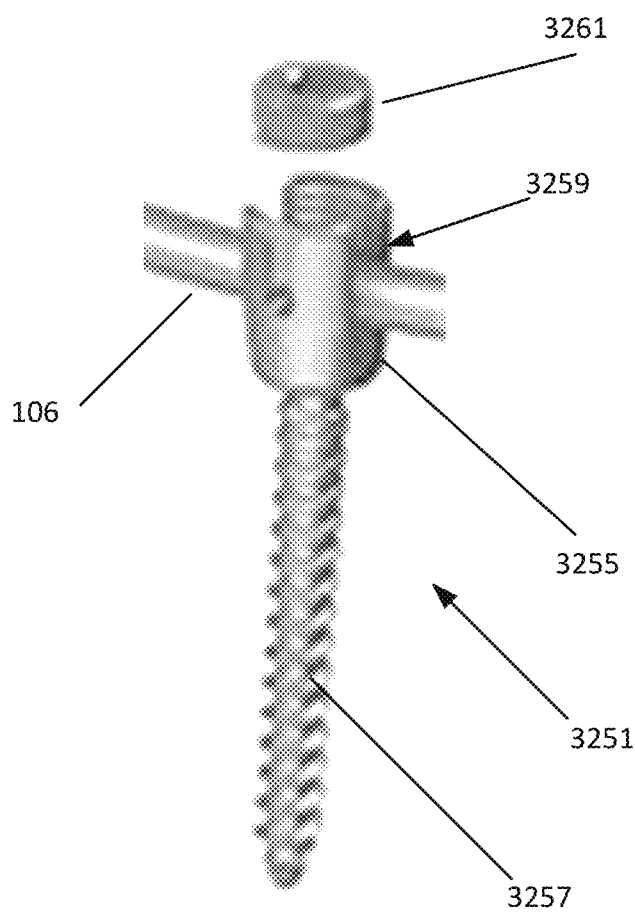

As shown in FIG. 32A, the probe tip 3207*a* may be paddle shaped with a cylindrical center 3208*a* which interfaces with the center of the screw's tulip head (before placement of the rod and locking cap). The probe geometry of FIG. 32A may allow it to be used to manipulate the tulip head 3255 to better represent the direction which the rod would be facing. Because the paddle portion of probe tip 3207*a* aligns with the U-shaped recess of the tulip head and the cylindrical portion aligns with the opening for the locking cap, when properly placed, the probe tip 3207*a* will align with both the center of the tulip head and a direction of the rod through the tulip head allowing determination of both the location and alignment of the U-shaped opening.

As shown in FIG. 32B, a side loading probe 3207*b* may interface with different connectors or screws that cannot be accessed from the top. The hook 3210*b* of the probe would represent the rod and allow the capture of a specific trajectory without requiring top access. FIG. 32C shows the side loading probe 3207*b* interfacing with a connector 3221*c* (with hook 3210*b* inside connector 3221*c*).

Software and/or control components of the rod bending system 10 are discussed below according to some embodiments of inventive concepts.

Figure 33:
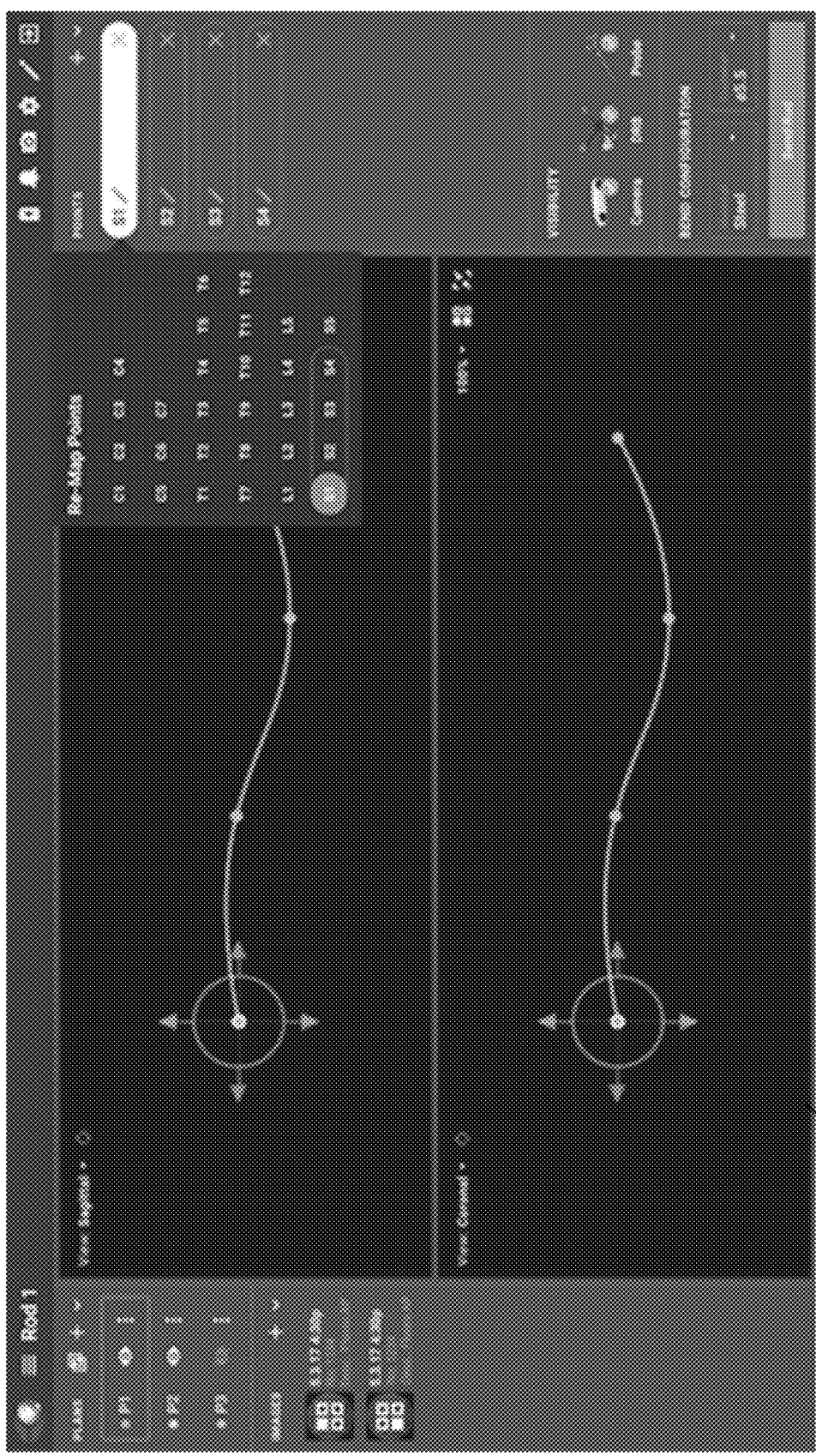
FIG. 33 is a screen shot showing transformation points in two orthogonal planes (e.g., the sagittal plane and the coronal plane) corresponding to a patient's anatomy according to some embodiments.

Software and/or control components (e.g., controller 102) of some embodiments of inventive concepts may provide a way to overlay captured transforms over patient images using display 118. Utilizing the transformation points, the controller/software may control the bending robot 100 to shape an implant for operational use. Additionally, prior to shaping the implant, the user (e.g., the surgeon) may also label transformation points to correspond to the patient's anatomy where bends may be needed (e.g., the S1-S4 vertebrae), a feature illustrated in FIG. 33. As shown in FIG. 33, four transformation points are illustrated in the upper and lower views taken in orthogonal planes/views (e.g., the Sagittal and Coronal planes), and these transformation points are identified as the first, second, third, and fourth sacral vertebrae (i.e., S1, S2, S3, and S4). These transformation points may be optically determined using camera 114 to determine probe tip placements in respective screws or other implants, for example, as discussed above with respect to FIGS. 29A, 29B, 30A, 30B, 31A, 31B, 32A, 32B, and 32C. Because the transformation points may be determined based on the existing spinal alignment, the user (e.g., surgeon) may adjust the transformation points on display 118 before initiating rod bending as indicated by the circle and arrow at the left most transformation point in each of the views of FIG. 33.

Controller/software operations to acquire transformation points may include pre-operative and/or intraoperative workflows, for example, as discussed below.

Intra-Operative acquisition of transformation points is discussed below.

To track rod attachment point acquisition, the controller/software may have the ability to automatically capture rod attachment points at respective screws (after screw placement), including the screw head orientation and position. Probes used to capture such rod attachment points are discussed above. Using the controller/software, the user (e.g., surgeon) can then send this captured information to the rod bender (e.g., rod bending robot) to shape the rod implant for clinical use.

Figure 34:
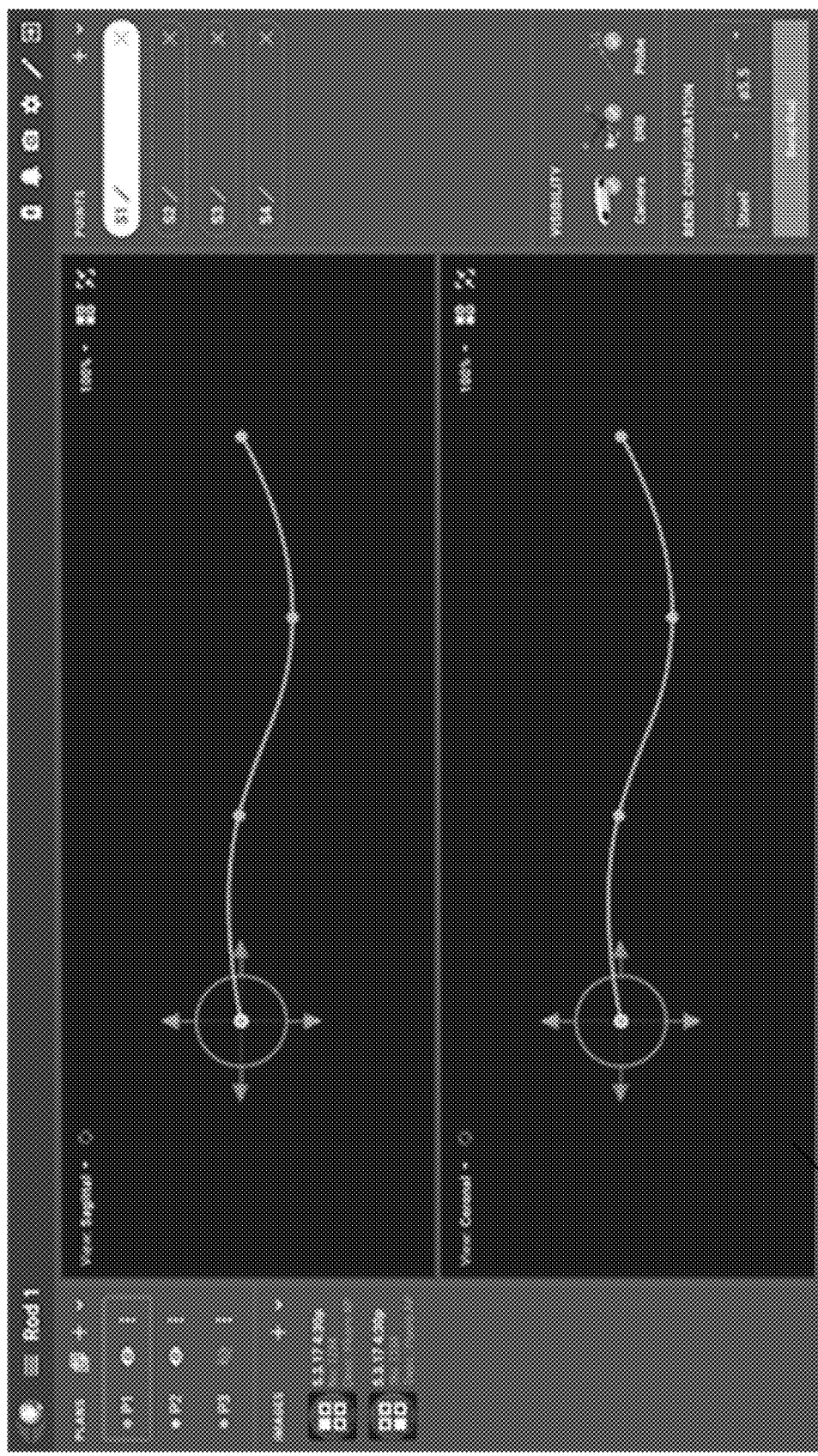
FIG. 34 is a screen shot showing adjustments to the transformation points of FIG. 33 in the two orthogonal planes according to some embodiments.

The controller/software can provide a way to optically capture attachment points using camera 114, for example, based on a position of a probe in camera space and/or a position of a probe with respect to a patient fixation tracking array. The controller/software may track probe position based on information from camera 114 and capture a current position/orientation of the probe tip responsive to stray movement (e.g., using a movable stray marker/reflector as discussed above with respect to FIGS. 29A, 29B, 30A, 30B, 31A and/or 31B) relative to the camera 114 or responsive to user interface (UI) action (e.g., via a touch sensitive portion of display 118, a physical button, a pedal, etc.). The user (e.g., surgeon) is also able to make adjustments in cardinal directions of transformation points before bending/shaping the implant, as shown in FIG. 34. In FIG. 34, initial transformation points have been input (e.g., optically captured) for screws in the first, second, third, and fourth sacral vertebrae (i.e., S1, S2, S3, and S4), with the transformation point for the first sacral vertebrae S1 selected for adjustment as indicated by highlighting "S1" on the right of the screen and by displaying a circle around the S1 transformation point in both of the sagittal and coronal views. In this configuration, the user (e.g., surgeon) can adjust the location of the S1 transformation point in the sagittal view and/or coronal view to affect movement of the S1 transformation point in three dimensions. Any of the other transformation points (e.g., the S2, S3, and/or S4 transformation points) may be selected and adjusted in a similar manner. Adjustment may be performed by controller/software responsive to user input through touch sensitive portions of display 118, and/or responsive to user input through a separate user input interface (e.g., a mouse, joystick, track ball, keypad, etc.). For example, the user may touch the respective label (e.g., "S1", "S2", "S3", or "S4") on the right side of display 118 to select the respective transformation point, or the user may touch a transformation point in either the sagittal view or coronal view to select the transformation point. Once a transformation point is selected, the user may touch and drag the selected transformation point in the sagittal view to adjust a position of the transformation point in the sagittal plane, and/or the user may touch and drag the selected transformation point in the coronal view to adjust a position of the transformation point in the coronal view.

Figure 35:
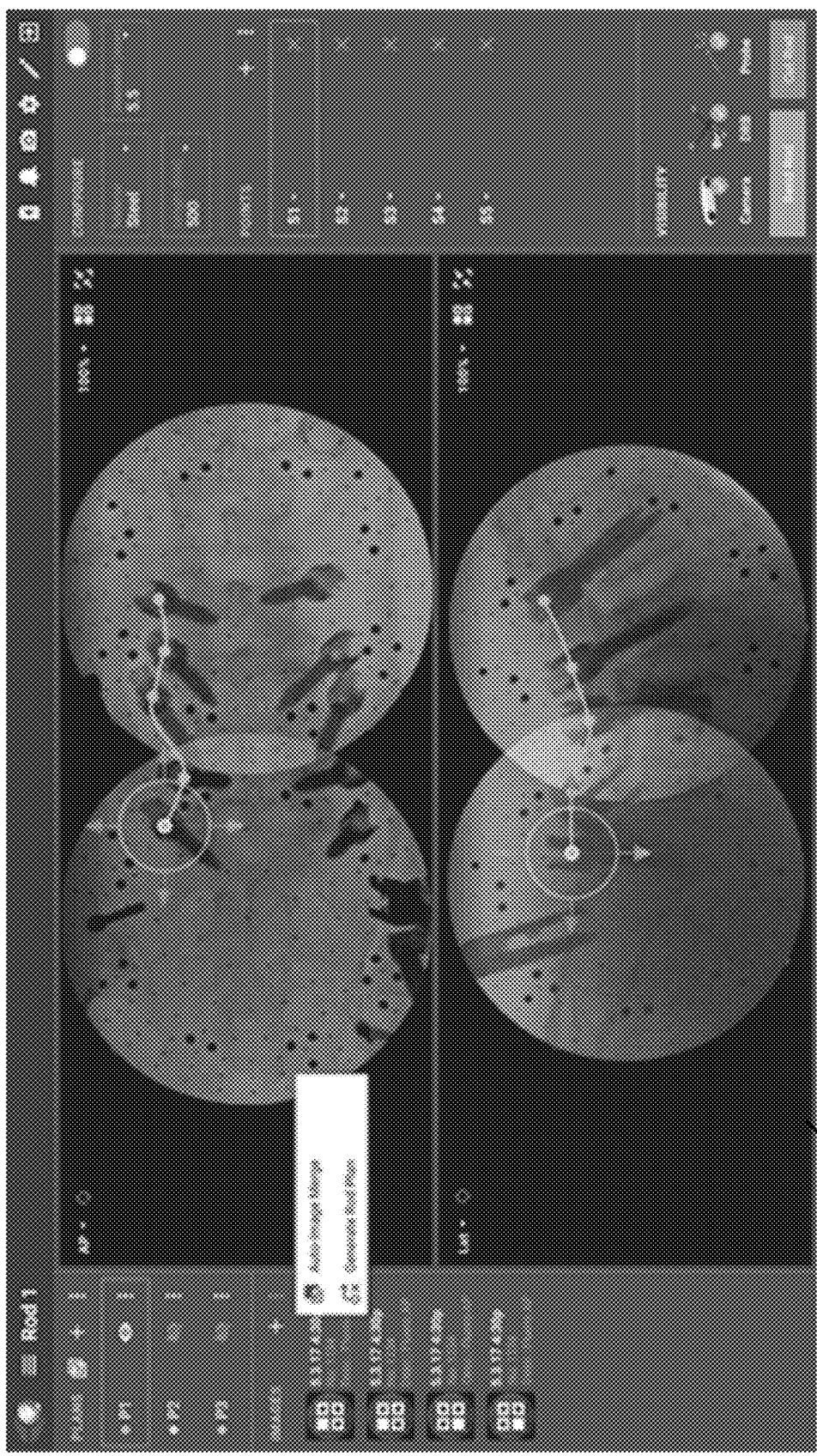
FIG. 35 is a screen shot showing a use of orthogonal fluoroscope images to construct a bend plan according to some embodiments.

According to some embodiments, fluoroscopy can be used for attachment point acquisition (also referred to as capture). The GRB can use fluoroscopic images to construct a bend plan for the rod intraoperatively. The user (e.g., surgeon) may capture fluoroscopy images of the patient. The controller/software will automatically locate and label attachment points for the rod based on screw placement as shown in FIG. 35. The user (e.g., surgeon) will be able to view these points in the sagittal and coronal views as shown in FIG. 35 and make adjustments as useful/necessary to obtain the desired bend plan for the rod.

Once the user (e.g., surgeon) reviews and accepts the bend plan, the GRB will shape the rod implant for surgical use.

Shaping the rod implant based on screw location in fluoroscopy is illustrated in FIG. 35. In FIG. 35, display 118 provides two orthogonal fluoroscopic images with 5 spinal screws identified for placement of surgical rod 106, and the 5 screws are identified as screws for the first, second, third, fourth, and fifth sacral vertebrae (i.e., S1, S2, S3, S4, and S5). The controller/software may automatically identify the five illustrated initial transformation points for the rod based on locations of the respective screws and create an initial bend plan for the rod based on the initial transformation points. The user (e.g., surgeon) may then select a transformation point on the display 118 for adjustment (e.g., by selecting/touching the respective label on the right of display 118, or by selecting/touching the respective transformation point in the sagittal or coronal view). In FIG. 35, the transformation point corresponding the S1 vertebrae is selected for adjustment as indicated by the box highlighting the label "S1" on the right side of display 118 and the circle (with arrows) surrounding the respective transformation point. The user may select and adjust one or more of the transformation points to provide a modified bend plan for the rod before initiating actual rod bending. Selection and/or adjustment may be provided as discussed above with respect to FIG. 34.

Pre-Operative operations are discussed below according to some embodiments of inventive concepts.

According to some embodiments, a screw plan may be used to generate a bend plan for a rod. The controller/software may allow the surgeon to plan a shape (also referred to as a bend plan) for the surgical rod implant based on attachment point placement created using the ExcelsiusGPS system. In such embodiments, pre-operative imaging (e.g., CAT scan imaging, MRI imaging, fluoroscopic imaging, etc.) may be used to provide images of the patient's anatomy (e.g., spine) in different (e.g., orthogonal) planes (e.g., sagittal and coronal planes) on display 118. Controller/software may then accept user input (e.g., using touch sensitive portions of display 118) to place virtual screws for the procedure on the display to provide the screw plan for the procedure. After placement of the virtual screw implants, the controller/software can automatically identify rod placement points for each virtual screw to provide initial transformation points for an initial rod bend plan, and the user can modify one or more of the initial transformation points to provide modified transformation points used to generate a modified bend plan for the rod. Once the user approves the bend plan, the user can send the bend plan (e.g., surgical shape) to the rod bender and shape the rod implant to fixate to attachment points of the screws.

Generation of a rod bend plan based on pre-operative virtual screw placement may be similar to intra-operative bend planning discussed above with respect to FIGS. 33, 34, and 35 that are based on actual screw placement. With both intra-operative and pre-operative bend planning, initial transformation points for an initial bend plan for the rod may be generated based on respective (real or virtual) screw placements, and the user may adjust one or more of the initial transformation points to generate the final bend plan for the rod. The imaging used for virtual screw placements may be similar to that of FIGS. 33, 34, and/or 35 except that the images of the virtual screws are added by the controller/software based on user input (as opposed to being included as a part of the original imaging.

If the surgeon does not use the GPS to insert the actual screw implants, the controller/software can still shape the surgical implant based on virtual/real attachment/screw point placement with other means, provided the plan is produced in proprietary format. After placing the real/virtual screw implants, the user can send the bend plan to the GRB, which will then shape the rod to allow fixation to the screw attachment points.

Merging of plans between pre-operative and intraoperative plans may also be provided according to some embodiments of inventive concepts. The controller/software may provide a way to combine two or more plans to form a merged plan. The user will be able to assign weights to both predicate plans that are used to calculate the merged bend plan, depending on the accuracy of each of the desired bend locations, as shown, for example, in FIG. 36.

Whether using placement of actual or virtual screws to generate a bend plan for a surgical rod, controller 102 may generate the bend plan to both: 1) fit points on the rod to respective transformation points (corresponding to respective attachment implants, e.g., screws); and 2) orient a trajectory of the rod at each transformation point to match a trajectory of the respective attachment implant (e.g., a trajectory/direction of a tulip head of the respective screw). Accordingly, the bend plan for the rod may consider both the positions of the attachment implants (e.g., screws) and the orientations of the attachment implants (e.g., orientations of tulip heads of the screws).

According to some embodiments of inventive concepts, software-based implant shaping verification may be provided.

After shaping the implant, the controller/software may provide verification that the implant is properly shaped using one or more approaches discussed below.

Tip verification may be provided as discussed below after completion of rod bending but before cutting the rod.

Using a tracked array 2815 on a base of the system, the user may be able to touch a tip of a tracked instrument to the tip/end of the rod implant after completion of bending but before cutting the rod. A numerical estimate of the accuracy of the bend may be provided on display 118 to the user for shape verification. Based on the intended bend plan, the controller/software can determine a planned/calculated position of the tip/end of the rod after completion of all bends, and the planned/calculated position of the tip/end of the rod can be compared with the actual position of the tip/end to generate the numerical estimate of accuracy of the rod shape. A single data point may thus be used to provide the numerical estimate of the overall accuracy of the rod shape.

Shape verification may be provided as discussed below after completion of rod bending but before cutting the rod.

Using a tracked array 2815 on the base of system, the user may be able to run a circular probe over the length of the implant and sample probe locations corresponding to respective rod locations to generate a numerical estimate of an accuracy of the rod shape after completion of rod bending but before cutting the rod. Based on the intended bend plan, the controller/software can determine planned/calculated positions along the length of the bend plan for the rod, and these planned/calculated positions may be compared with the actual sampled probe locations at corresponding positions along the length of the actual bent rod to generate the numerical estimate of the accuracy of the rod shape. A plurality of data points may thus be used to provide the numerical estimate of the overall accuracy of the rod shape.

Tool verification may be provided as discussed below after completion of rod bending and after cutting the rod.

Using two tracked instruments/probes, the user may touch both ends of the implant to verify shape accuracy using calculations based on where the tips of the rod implant are in relation to the center of the rod implant after completion of bending and before/after cutting. Based on the intended bend plan, the controller/software can determine a planned/calculated distance between the two tips/ends of the rod, and an actual distance between the two tips/ends of the actual bent rod can be determined based on an optical determination of the actual tips/ends of the bent rod using camera 114 and the tracked probes.

Placement of the rod implant is discussed below according to some embodiments of inventive concepts.

After checking/ensuring accuracy of the rod implant shape/properties (e.g., bends, length, etc.), the user may cut the rod implant and then place the implant into the tulips of the screw heads and secure the rod in each screw using a respective locking cap.

After the automatic rod bender has bent the rod, it may be difficult for the user (e.g., surgeon) to know the proper orientation of the rod with respect to the spine. Even after the user (e.g., surgeon) is able to determine the proper orientation of the rod, the user (e.g., surgeon) may need to fix an end of the rod to the first/last screw to provide/ensure that the rod does not slide while fixing it to the other/remaining screws. The fixing of the rod to the last/first screw may also help to provide/ensure that the rod falls accurately where it needs to be without the rod sliding on the screws.

The following approaches may help the user (e.g., surgeon) to orient the rod 106 with respect to the spine and/or to fix the rod 106 on the first/last screw.

Figure 37:
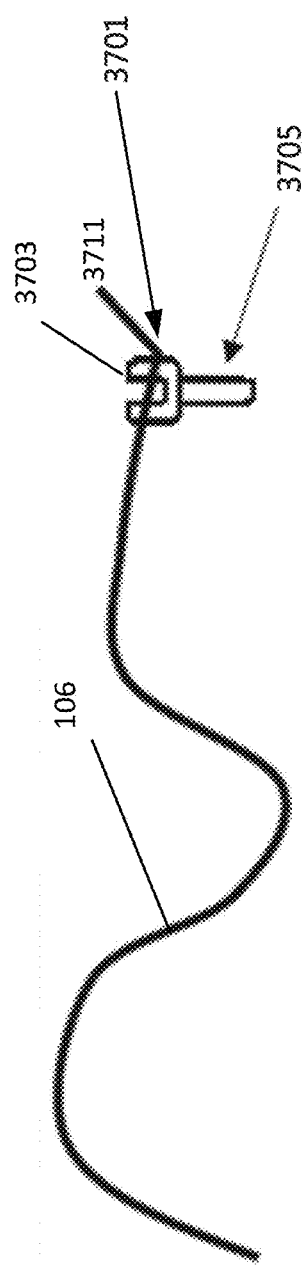
FIG. 37 illustrates use of a bend at the end of the rod to reduce/prevent movement of the rod.

According to some embodiments, an extra bend 3801 may be added to the rod 106 before cutting as shown in FIG. 37.

The extra bend 3701 can be added to the end of the already bent rod 106 using the automatic rod bender. The extra bend 3701 can be used both to assist the user (e.g., surgeon) to orient the rod and/or to reduce/prevent sliding of the rod during/after the procedure as shown, for example, in FIG. 37. As shown in FIG. 37, the extra bend 3701 may stop the bent rod 106 from sliding to the left through the tulip head 3703 of screw 3705 while securing the rod to other screws (not shown). The extra bend can also assist in proper placement of the rod relative to the first/last screw 3805 by providing a "stop" against the tulip head 3703 when the rod is properly positioned. In addition, a direction of the extra bend 3701 can be used to indicate a proper rotation of the rod relative to screw 3705. For example, the portion of the rod between the extra bend 3701 and rod end 3711 may be configured to lay horizontal (or vertical) when the rod is in a proper rotational position. By providing that portions of the rod between the extra bend 3701 and the end of the rod 3711 are configured to extend in a direction that is orthogonal with respect to sides of the U-shaped opening in the tulip head, the bend may act as a "stop" with respect to rod 106 sliding to the left in FIG. 37.

Figure 38:
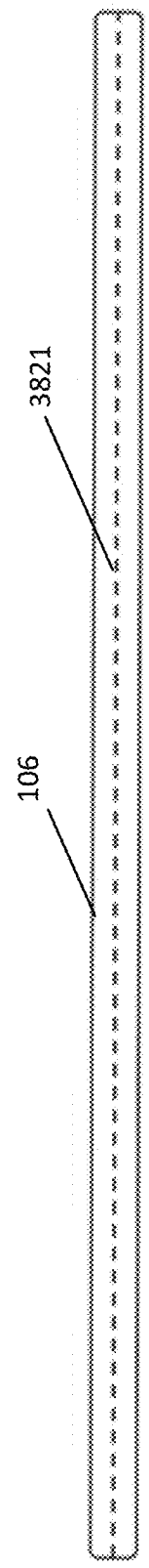
FIG. 38 illustrates markings on the rod according to some embodiments.

According to some embodiments, markings 3821 on the rod 106 may be used to orient the rod 106 as shown in FIG. 38. Many spinal rods may come with a distinct dotted or solid midline marking 3821, as illustrated in FIG. 38. The following operations can be followed to use the midline 3821 as an orientation marker.

According to some embodiments, the rod 106 may be inserted into the rod bender (e.g., into rod feeding subassembly 104) in a way that the midline 3821 faces up. There can also be a central line on the rod bender to help the user match the rod to this line. This may be referred to as the home position of the rod 106 prior to initiating bending.

According to some embodiments, the rod bender controller/software may know precisely the total rotation the rod needs to go through to achieve the 3D bending.

At the start of bending operations the rod bender can rotate the rod to such a position such that after the rod has been completely bent by the rod bender, the midline faces up when oriented as intended for fixation to the patient.

Figure 39:
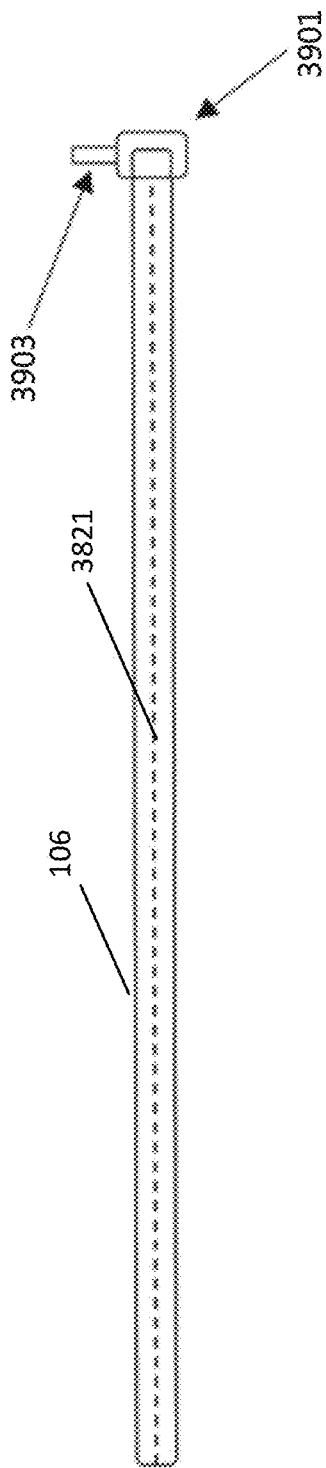
FIG. 39 illustrates a cap on an end of the rod according to some embodiments.

According to some embodiments, a biocompatible cap 3901 may be provided at the end of the rod 106 as shown in FIG. 39.

A biocompatible cap 3901 as illustrated in FIG. 39 can be placed at the end of the rod 106 to help the user (e.g., surgeon) determine the orientation of the rod 106 with respect to the spine after the rod 106 is bent and at the same time reduce/prevent sliding of the rod on the polyaxial screw head. The cap may need to be placed on the front end of the rod 106 (i.e., the end that is first fed into the rod feeding subassembly 104 and the bending subassembly 110) as the other end of the rod is cut. The cap can be threaded or pressfit to the end of the rod. After the rod has been fixed to the spine, the cap can be removed. As mentioned with respect to embodiments discussed above, the controller/software may know exactly the amount of rotation that the rod has to go through to facilitate 3D (three dimensional) bending. After the rod is inserted into the rod bender (but before initiating bending), the cap can be placed in such a way that a standoff feature 3903 on the cap faces up. This may indicate a home position. Now the rod bender can rotate the rod to a position so that after the rod is bent completely, the standoff feature 3903 faces up when properly oriented for fixation to the patient. In this way a desired orientation of the rod may be indicated to the user (e.g., surgeon) when placing/fixing the rod to the spinal screws.

According to some embodiments of inventive concepts, sterility of the mechanical housing 121 (also referred to as a top assembly) may be maintained throughout rod bending operations. In particular, the mechanical housing 121 may be compatible with autoclave sterilization, and a sterile drape can be used to isolate the motor housing 122 from the sterile surgical environment while providing mechanical coupling between the mechanical and motor housings. During rod bending operations, the rod is thus in contact with components of the sterile mechanical housing 121 while the rod is isolated from the motor housing 122 which may be incompatible with autoclave sterilization.

According to some embodiments of inventive concepts, placement of the rod bender system on a cart may improve mobility of the system.

According to some embodiments of inventive concepts, an automatic springback equation calculation can be performed on a sacrificial rod (matched to the actual rod implant) to enable the rod bender to bend rods of any material without any prior data regarding the rod's material/springback properties.

According to some embodiments of inventive concepts, a rod bending system may be able to seamlessly capture and shape surgical rod implants based on multiple different acquisition methods. The open platform design may allow a user to select the implant system that best suits the patient.

According to some embodiments of inventive concepts, a rod bending system may also be able to rapidly shape the rod implant in under two minutes, reducing an amount of time the patient is under anesthesia as well as reducing stress on the patient when inserting the rod implant.

According to some embodiments of inventive concepts, a rod bending system may use patient specific transformation points (including live transformation points generated based on fluoroscopy) to capture attachment points. This may assist in generating a best-fit shape for the attachment/bend plan.

Figure 40:
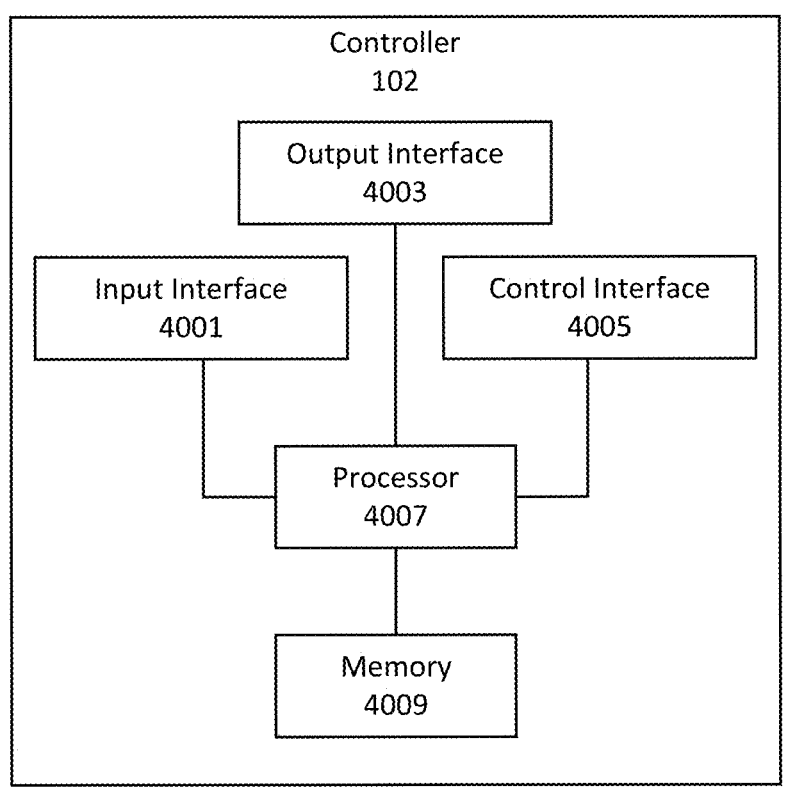
FIG. 40 is a block diagram illustrating a controller according to some embodiments of inventive concepts.

FIG. 40 is a block diagram illustrating elements of controller 102 of rod bending system 10. As shown, controller 102 may include processor 4007 (also referred to as a processor circuit or processor circuitry) coupled with input interface 4001 (also referred to as an input interface circuit or input interface circuitry), output interface 4003 (also referred to as an output interface circuit or output interface circuitry), control interface 4005 (also referred to as a control interface circuit or control interface circuitry), and memory 4009 (also referred to as a memory circuit or memory circuitry). Memory 4009 may include computer readable program code that when executed by processor 4007 causes processor 4007 to perform operations according to embodiments disclosed herein. According to other embodiments, processor 4007 may be defined to include memory so that a separate memory circuit is not required.

As discussed herein, operations of controlling a rod bending system according to some embodiments of the present disclosure may be performed by controller 102 including processor 4007, input interface 4001, output interface 4003, and/or control interface 4005. For example, processor 4007 may receive user input through input interface 4001, and such user input may include user input received through a touch sensitive portion of display 118 and/or through other user input such as a keypad(s), joystick (s), track ball(s), mouse(s), etc. Processor 4007 may also receive optical input information from camera 114 and/or feedback information from bending robot 100 through input interface 5001. Processor 4007 may provide output through output interface 4003, and such output may include information to render graphic/visual information on display 118. Processor 4007 may provide robotic control information/instruction through control interface 4005 to bending robot 100, and the robotic control instruction may be used, for example, to control operation of rod feeding subassembly 106, brake subassembly 108, and/or bending subassembly 110.

Figure 41:
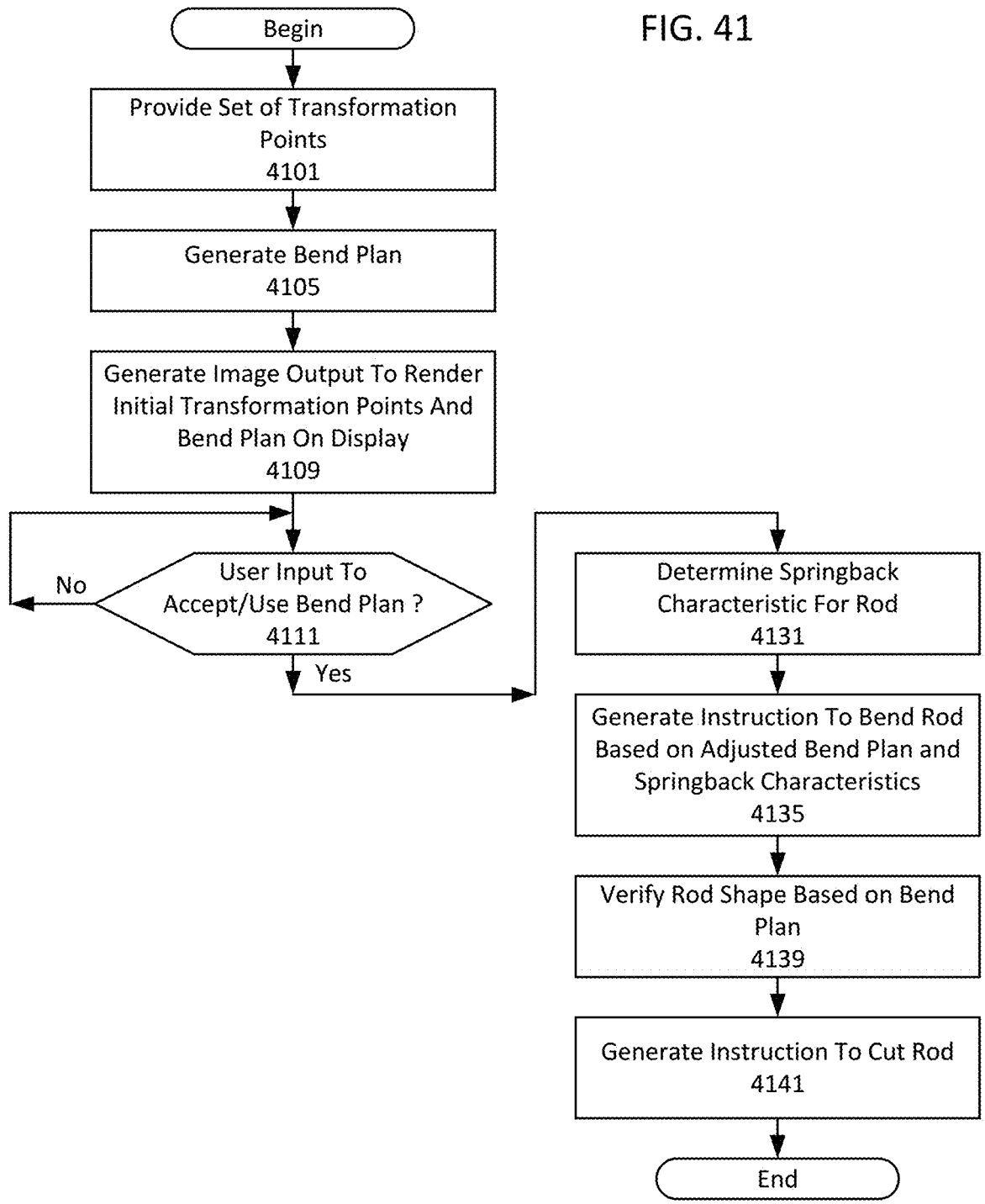
FIGS. 41-44 are flow charts illustrating operations of the controller of FIG. 40 according to some embodiments of inventive concepts.

FIG. 41 illustrates operations of controller 102 according to some embodiments of inventive concepts.

At block 4101, processor 4007 may provide a set of transformation points corresponding to respective attachment implants (e.g., screws). The transformation points of the set may be provided, for example, based on at least one of: optically capturing locations of attachment implants affixed to a patient using camera 114 (e.g., using a tracked probe to point to attachment implants); locations of actual attachment implants in a medical image; and/or locations of virtual attachment implants in a medical image.

At block 4105, processor 4007 may generate a bend plan for the surgical rod based on the set of transformation points. The bend plan, for example, may define a plurality of bend angles at respective bend positions along the surgical rod and corresponding rotational positions.

At block 4109, processor 4007 may generate an image output (provided through output interface 4003 to display 118) to render the set of transformation points and the bend plan on display 118 as discussed above, for example, with respect to FIGS. 33, 34, 35, and 36. As shown in embodiments of FIGS. 33, 34, 35, and 36, the image output may be generated to render the set of transformation points and the bend plan in a first plane (e.g., the Sagittal plane) on a first portion of the display 118 and to render the set of transformation points and the bend plan in a second plane (e.g., the coronal plane) on a second portion of the display 118, with the first and second planes being different (e.g., orthogonal). As shown in embodiments of FIG. 35, the image output may be generated to render the set of transformation points and the bend plan together with a medical image (e.g., a computed tomography CT scan image, an magnetic resonance imaging MRI image, and/or a fluoroscopy image) on the display 118. As further shown in FIG. 35, the image output may be generated to render the set of transformation points and the bend plan on the display 118 with a medical image including real/virtual attachment implants (e.g., screws).

At block 4111, processor 4007 may proceed with rod bending responsive to receiving user input (through input interface 4001) to proceed. For example, the user (e.g., surgeon) may adjust one or more of the transformation points on the display 118 to adjust the bend plan before actually bending the surgical rod.

At block 4131, a sacrificial rod 106' may be used to determine a springback characteristic for the surgical rod 106 before bending the surgical rod as discussed above, for example, with respect to FIGS. 27 and 28. Responsive to user input to accept/use the bend plan at block 4111, processor 4007 may generate image output (provided through output interface 4003 to display 118) to render a prompt on display 118 to load sacrificial rod 106' into bending robot 100, and once the sacrificial rod has been loaded, processor 4007 may proceed with determining the springback characteristic for the surgical rod using the sacrificial rod 106'. Processor 4007 may proceed with springback characteristic determination responsive to determining loading of the sacrificial rod based on feedback (received through input interface 4001) from bending robot 100 and/or camera 118 and/or based on user input (e.g., received through a touch sensitive portion of display 118 and input interface 4001) that loading is complete.

As discussed above, the springback characteristic may be determined based on a detected springback of the sacrificial rod 106' at two different bend angles. Accordingly, processor 4007 may generate instruction (provided through control interface 4005 to bending robot 100) to bend the sacrificial rod 106' at a first test position to a first test bend angle, and responsive to this instruction, rod feeding subassembly 104 of bending robot 100 may feed the sacrificial rod 106' to the first test position, brake subassembly 108 may lock the sacrificial rod 106' in the first test position, and bending subassembly 110 may bend the sacrificial rod to the first test bend angle. Processor 4007 may then determine a first springback from the first test bend angle, for example, based on optical feedback received through camera 114 and/or based on detecting a point at which the bending subassembly reengages the sacrificial rod after release. Processor 4007 may then generate instruction (provided through control interface 4005 to bending robot 100) to bend the sacrificial rod 106' at a second test position to a second test bend angle, and responsive to this instruction, rod feeding subassembly 104 of bending robot 100 may feed the sacrificial rod 106' to the second test position, brake subassembly 108 may lock the sacrificial rod 106' in the second test position, and bending subassembly 110 may bend the sacrificial rod 106' to the second test bend angle. Processor 4007 may then determine a second springback from the second test bend angle, for example, based on optical feedback received through camera 114 and/or based on detecting a point at which the bending subassembly reengages the sacrificial rod 106' after release. Processor 4007 may then determine the springback characteristic for the surgical rod based on the first springback from the first test bend angle from the sacrificial rod 106' and the second springback from the second test bend angle for the sacrificial rod 106'. While determination of the springback characteristic is shown after generating the bend plan, the springback characteristic may be determined at any time prior to rod bending.

Once the springback characteristic for the surgical rod 106 has been determined, processor 4007 may generate a prompt on display 118 to load the surgical rod 106 into bending robot 100, and once the surgical rod has been loaded, processor 4007 may proceed with bending operations of block 4135 as discussed below. Processor 4007 may proceed with bending operations responsive to determining loading of the surgical rod based on feedback (received through input interface 4001) from bending robot 100 and/or camera 118 and/or based on user input (e.g., received through a touch sensitive portion of display 118 and input interface 4001) that loading is complete.

At block 4135, processor 4007 may generate instruction to bend the surgical rod based on the bend plan and based on the springback characteristic for the surgical rod in block 4131. Accordingly, instruction for each bend may be provided so that bending subassembly 110 bends the surgical rod (based on the springback characteristic) past the desired bend angle so that that the desired bend angle is achieved after springback. Rod bending operations of block 4135 are illustrated in greater detail in FIG. 44.

At block 4401, processor 4007 may generate instruction (provided through control interface 4005 to bending robot 100) to feed the surgical rod to a first bend position of the plurality of bend positions. Responsive to this instruction, rod feeding subassembly 104 may feed the surgical rod to the first bend position.

At block 4405, processor 4007 may generate instruction (provided through control interface 4005 to bending robot 100) to rotate the surgical rod to a first rotational position. Responsive to this instruction, rod feeding subassembly 104 may rotate the surgical rod to the first rotational position.

At block 4409, processor 4007 may generate instruction (provided through control interface 4005 to bending robot 100) to bend the surgical rod to a first bend angle of the plurality of bend angles while the surgical rod is maintained at the first bend position and the first rotational position. Responsive to this instruction, brake subassembly 108 may lock the surgical rod in the first bend position and the first rotational position while bending subassembly 110 bends the surgical rod to the first bend angle (e.g., bending the surgical rod past the first bend angle in accordance with the springback characteristic so that the first bend angle is achieved after completion of the operation).

At block 4411, processor 4007 may generate (4401) instruction (provided through control interface 4005 to bending robot 100) to feed the surgical rod to a next bend position of the plurality of bend positions. Responsive to this instruction, rod feeding subassembly 104 may feed the surgical rod to the next bend position.

At block 4415, processor 4007 may generate instruction (provided through control interface 4005 to bending robot 100) to rotate the surgical rod to a next rotational position. Responsive to this instruction, rod feeding subassembly 104 may rotate the surgical rod to the next rotational position.

At block 4419, processor 4007 may generate instruction (provided through control interface 4005 to bending robot 100) to bend the surgical rod to a next bend angle of the plurality of bend angles while the surgical rod is maintained at the next bend position and the next rotational position. Responsive to this instruction, brake subassembly 108 may lock the surgical rod in the next bend position and the next rotational position while bending subassembly 110 bends the surgical rod to the next bend angle (e.g., bending the surgical rod past the next bend angle in accordance with the springback characteristic so that the next bend angle is achieved after completion of the operation).

Operations of blocks 4411, 4415, and 4419 may be repeated for each bend of the bend plan provided to fit the surgical rod to the attachment implants (e.g., screws) corresponding to the transformation points, until rod bending is complete at block 4421.

According to some embodiments, operations 4431, 4435, and 4439 may be performed to provide a final bend (also referred to as an extra bend) configured to provide a stop with respect to an attachment implant (e.g., screw) corresponding to the last of the transformation points. Such bends are discussed above with respect to FIG. 37.

At block 4431, processor 4007 may generate instruction (provided through control interface 4005 to bending robot 100) to feed the surgical rod to a final bend position after the last of the transformation points for the bend plan. Responsive to this instruction, rod feeding subassembly 104 may feed the surgical rod to the final bend position.

At block 4435, processor 4007 may generate instruction (provided through control interface 4005 to bending robot 100) to rotate the surgical rod to a final rotational position. Responsive to this instruction, rod feeding subassembly 104 may rotate the surgical rod to the final rotational position.

At block 4439, processor 4007 may generate instruction (provided through control interface 4005 to bending robot 100) to bend the surgical rod to the final bend angle while the surgical rod is maintained at the final bend position and the final rotational position. Responsive to this instruction, brake subassembly 108 may lock the surgical rod in the final bend position and the final rotational position while bending subassembly 110 bends the surgical rod to the final bend angle. As noted above, the final bend angle may be configured to provide a stop with respect to the attachment implant corresponding to the last of the transformation points.

Figure 44:
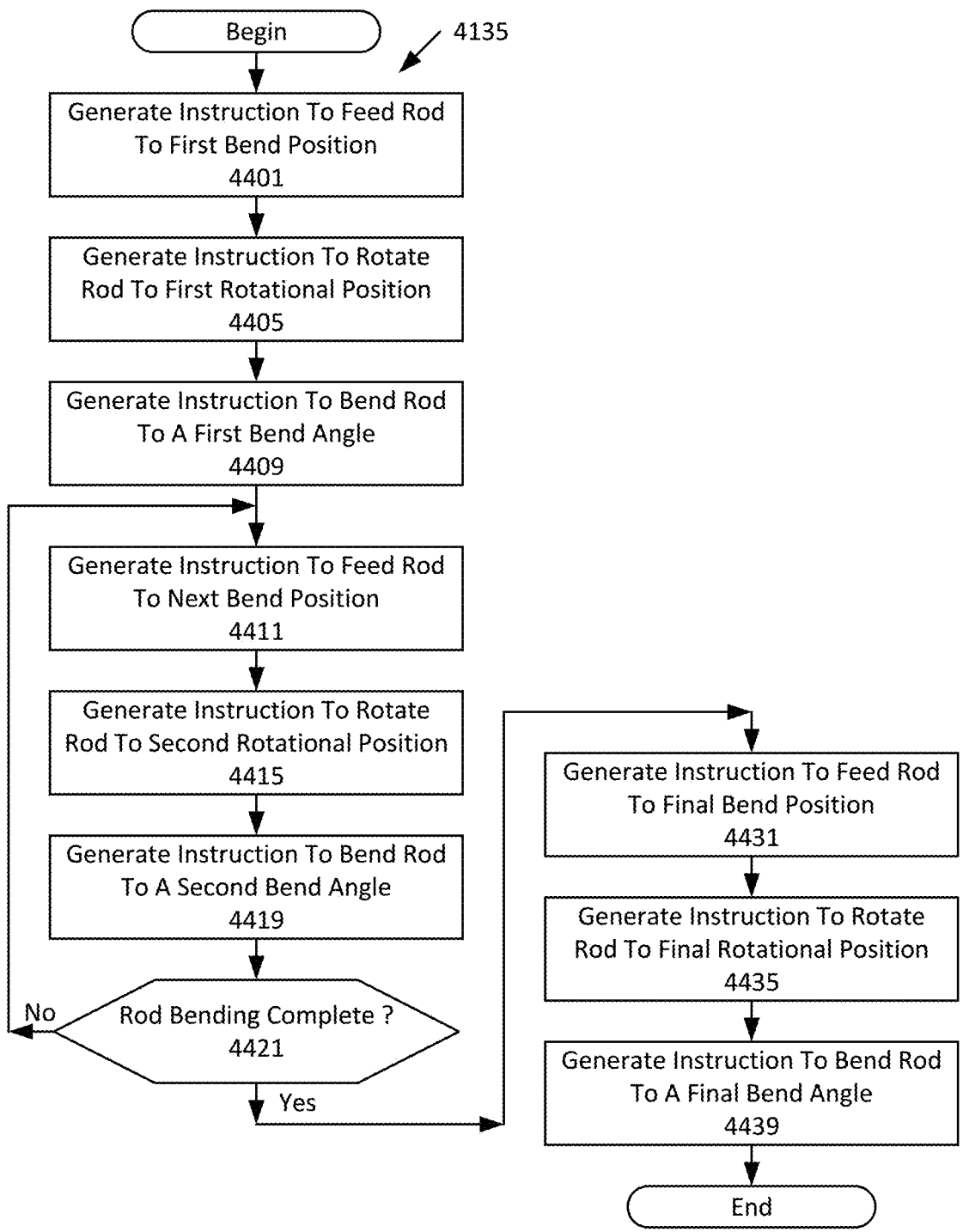

According to some embodiments, instructions from different blocks of FIG. 44 may be provided separately to bending robot 100 as each operation is performed, or instructions from different blocks of FIG. 44 may be provided to bending robot 100 together so that bending robot may perform instructions from a group of blocks with some autonomy. According to some embodiments, controller 102 may be defined to include control elements at bending robot 100, and according to some other embodiments, bending robot 100 may include a separate controller that received instruction from controller 102 to control bending operations at bending robot 100 based on instruction from controller 102.

At block 4139 of FIG. 41, processor 4007 may verify a shape of the surgical rod based on the bend plan and based on optical feedback received through camera 114 after completion of bending the surgical rod at each of the bend positions. For example, the optical feedback may be used to identify a location of at least one point of the rod in space based on a position of a probe tracked using camera 118. Such verification may be performed, for example, as discussed above with respect to implant shaping verification (e.g., tip verification, shape verification, tool verification, etc.). Processor 4007, for example, may determine a numerical verification score that is provided on display 118, and/or may provide a pass/fail indication on display 118.

At block 4141, processor 4007 may generate instruction (provided through control interface 4005 to bending robot 100) to cut the surgical rod after completion of bending the surgical rod at each of the bend positions. Responsive to this instruction, bending robot 100 may cut the surgical rod to remove excess portions there so that the surgical rod can be secured to the attachment implants (screws). While instruction to cut the surgical rod may follow instruction to verify rod shape according to some embodiments, according to some other embodiments, the order may be reversed.

Figure 42:
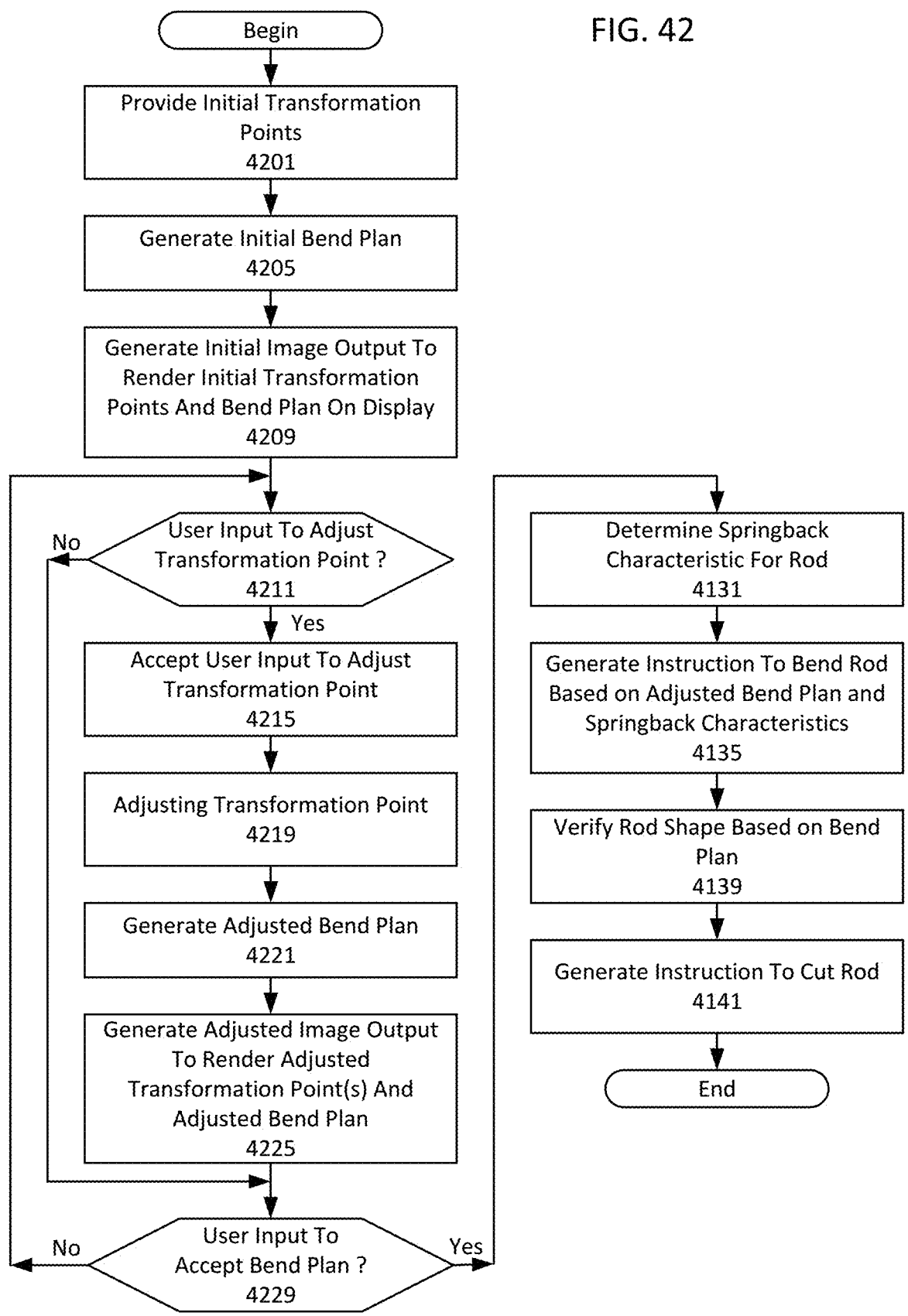

FIG. 42 illustrates operations of controller 102 according to some other embodiments of inventive concepts.

At block 4201, processor 4007 may provide an initial set of transformation points corresponding to respective attachment implants (e.g., screws). The transformation points of the initial set may be provided, for example, based on at least one of: optically capturing locations of attachment implants affixed to a patient using camera 114 (e.g., using a tracked probe to point to attachment implants); locations of actual attachment implants in a medical image; and/or locations of virtual attachment implants in a medical image.

At block 4205, processor 4007 may generate an initial bend plan for the surgical rod based on the initial set of transformation points. The initial bend plan, for example, may define a plurality of bend angles at respective bend positions along the surgical rod and corresponding rotational positions.

At block 4209, processor 4007 may generate an initial image output (provided through output interface 4003 to display 118) to render the initial set of transformation points and the initial bend plan on display 118, as discussed above, for example, with respect to FIGS. 33, 34, and 35. As shown in embodiments of FIGS. 33, 34, and 35, the initial image output may be generated to render the initial set of initial transformation points and the initial bend plan in a first plane (e.g., the Sagittal plane) on a first portion of the display 118 and to render the initial set of transformation points and the initial bend plan in a second plane (e.g., the coronal plane) on a second portion of the display 118, with the first and second planes being different (e.g., orthogonal). As shown in embodiments of FIG. 35, the initial image output may be generated to render the initial set of transformation points and the initial bend plan together with a medical image (e.g., a computed tomography CT scan image, an magnetic resonance imaging MRI image, and/or a fluoroscopy image) on the display 118. As further shown in FIG. 35, the initial image output may be generated to render the initial set of transformation points and the bend plan on the display 118 with a medical image including real/virtual attachment implants (e.g., screws).

After providing the initial image output on display 118, processor 4007 may accept user input to adjust one or more transformation points of the initial set as discussed below. At blocks 4211 and 4215, processor 4007 may accept user input to adjust one of the transformation points. As discussed above with respect to FIGS. 33, 34, and 35, for example, one of the transformation points (e.g., transformation point S1, as shown) may be selected (e.g., via touch sensitive portions of display 118 or other user input) and moved/dragged (e.g., via touch sensitive portions of display 118 or other user input). Responsive to user input to adjust the transformation point (e.g., transformation point S1, as shown), processor 4007 may adjust the transformation point to provide an adjusted set of transformation points at block 4219.

At block 4221, processor 4007 may generate an adjusted bend plan for the surgical rod based on the adjusted set of transformation points. The adjusted bend plan may thus define an adjusted plurality of bend angles at respective adjusted bend positions along the surgical rod and corresponding adjusted rotational positions determined based on the adjusted transformation point.

At block 4225, processor 4007 may generate an adjusted image output (provided through output interface 4003 to display 118) to render the adjusted set transformation points and the adjusted bend plan on display 118. the adjusted image output may be generated to render the adjusted set of transformation points and the adjusted bend plan in a first plane (e.g., the Sagittal plane) on a first portion of the display 118 and to render the adjusted set of transformation points and the adjusted bend plan in a second plane (e.g., the coronal plane) on a second portion of the display 118, with the first and second planes being different (e.g., orthogonal). Moreover, the adjusted image output may be generated to render the adjusted set of transformation points and the adjusted bend plan together with a medical image (e.g., a computed tomography CT scan image, an magnetic resonance imaging MRI image, and/or a fluoroscopy image) on the display 118. In addition, the adjusted image output may be generated to render the adjusted set of transformation points and the adjusted bend plan on the display 118 with a medical image including real/virtual attachment implants (e.g., screws).

Operations of blocks 4211, 4215, 4219, 4221, 4225, and 4229 may be repeated any number of times to adjust any number of the transformation points any number of times until user input is received (e.g., through a touch sensitive portion of display 118 or other user input device) to accept the bend plan at block 4229. If no user input is provided at block 4221, the initial bend plan may be accepted at block 4229 to provide an accepted bend plan. If one or more transformation points are adjusted at blocks 4211, 4215, 4219, one or more adjusted bend plans may be generated at block 4221, and the final adjusted bend plan may become the accepted bend plan. The resulting accepted bend plan may then be used to proceed with operations of blocks 4131, 4135, 4139, and/or 4141, which may be performed as discussed above with respect to FIG. 41.

Figure 43:
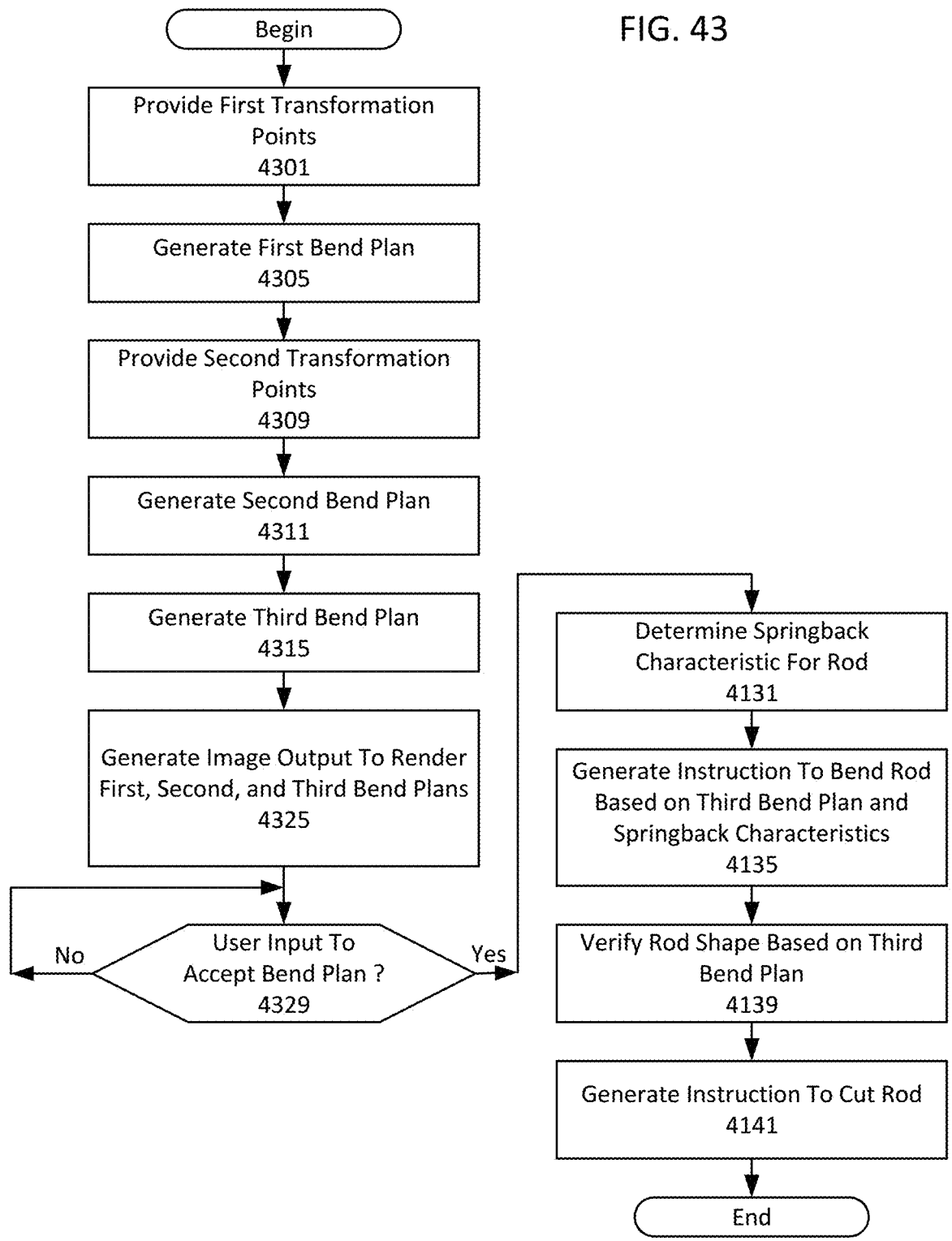

FIG. 43 illustrates operations of controller 102 according to still other embodiments of inventive concepts.

At block 4301, processor 4007 may provide a first set of transformation points corresponding to respective attachment implants. The transformation points of the first set may be provided, for example, based on at least one of: optically capturing locations of attachment implants affixed to a patient using camera 114 (e.g., using a tracked probe to point to attachment implants); locations of actual attachment implants in a medical image; and/or locations of virtual attachment implants in a medical image.

At block 4305, processor 4007 may generate a first bend plan for the surgical rod based on the first set of transformation points. The first bend plan, for example, may define a first plurality of bend angles at respective bend positions along the surgical rod and corresponding rotational positions.

At block 4309, processor 4007 may provide a second set of transformation points corresponding to the respective attachment implants, with the first and second sets of transformation points being different. The transformation points of the second set may be provided, for example, based on at least one of: optically capturing locations of attachment implants affixed to a patient using camera 114 (e.g., using a tracked probe to point to attachment implants); locations of actual attachment implants in a medical image; and/or locations of virtual attachment implants in a medical image. For example, the first set of transformation points may be provided based on preoperative medical imaging with virtual attachment implants (e.g., screws) placed therein, and the second set of transformation points may be provided based on intra-operative medical imaging after fixation of real/actual attachment implants (e.g., screws).

At block 4311, processor 4007 may generate a second bend plan for the surgical rod based on the second set of transformation points, with the first and second bend plans being different. The second bend plan, for example, may define a second plurality of bend angles at respective bend positions along the surgical rod and corresponding rotational positions.

At block 4315, processor 4007 may generate a third bend plan for the surgical rod based on merging the first and second bend plans and/or based on merging the first and second sets of transformation points as discussed above, for example, with respect to FIG. 36. In addition, processor 4007 may generate a third set of transformation points based on merging the first and second sets of transformation points. Processor 4007, for example, may generate the transformation points of the third set based on averaging/merging respective transformation points of the first and second sets and/or based on determining midpoints between respective transformation points of the first and second sets. Processor 4007 may then generate the third bend plan based on the third set of transformation points. The third bend plan (also referred to as a merged bend plan) may thus define a plurality of bend angles at respective bend positions along the surgical rod and corresponding rotational positions.

At block 4325, processor 4007 generate an image output (provided through output interface 4003 to display 118) to render the first, second, and third bend plans on display 118 as discussed above, for example, with respect to FIG. 36.

Figure 36:
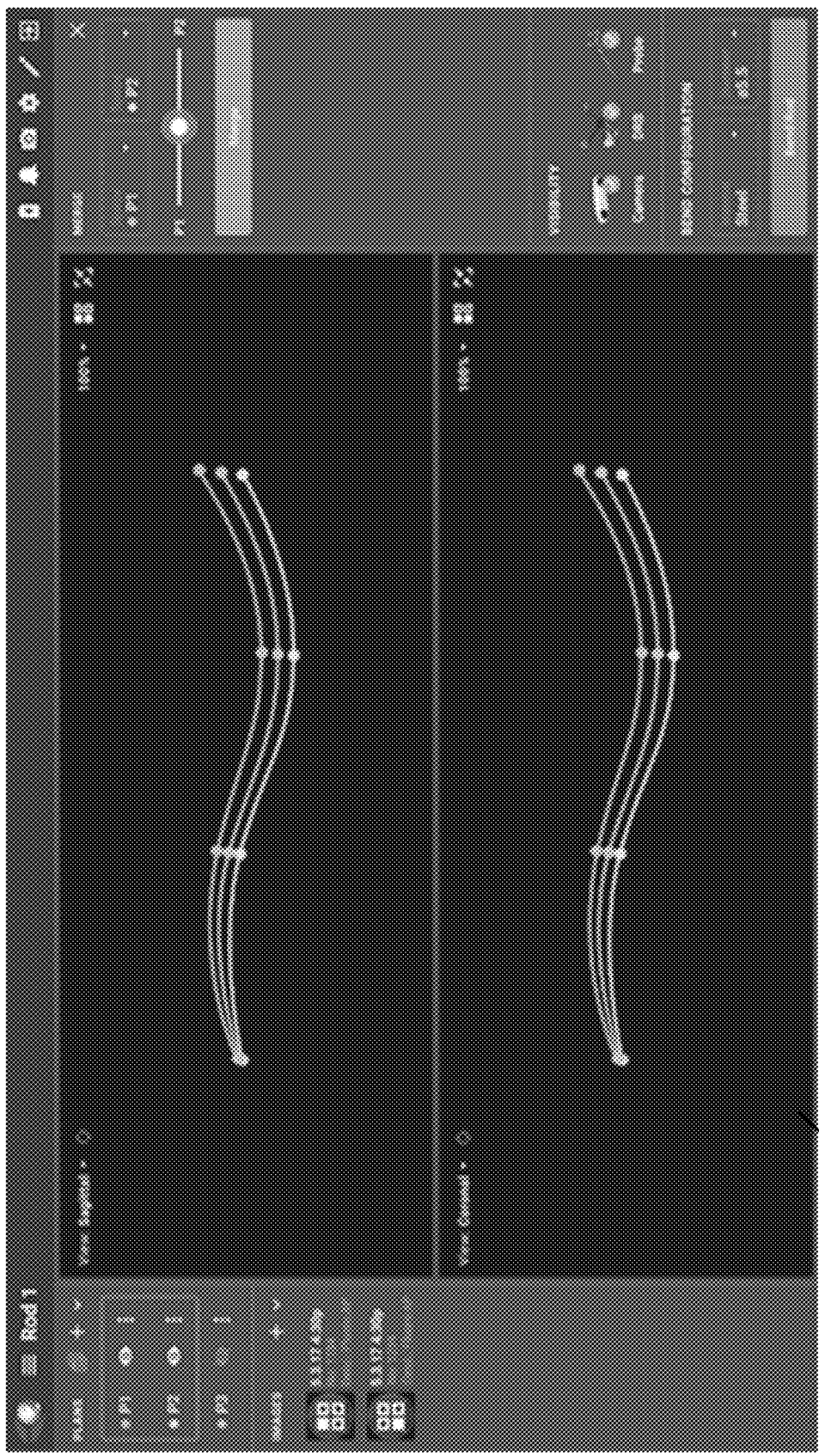
FIG. 36 is a screen shot showing merging of multiple bend plans to for a merged plan according to some embodiments.

As shown in embodiments of FIG. 36, the image output may be generated to render the first, second, and third sets of transformation points and the respective first, second, and third bend plans in a first plane (e.g., the Sagittal plane) on a first portion of the display 118 and to render the first, second, and third sets of transformation points and the respective first, second, and third bend plans in a second plane (e.g., the coronal plane) on a second portion of the display 118, with the first and second planes being different (e.g., orthogonal). In addition, the image output may be generated to render the sets of transformation points and the bend plans together with a medical image (e.g., a computed tomography CT scan image, an magnetic resonance imaging MRI image, and/or a fluoroscopy image) on the display 118. Moreover, the image output may be generated to render the sets of transformation points and the bend plans on the display 118 with a medical image including real/virtual attachment implants (e.g., screws).

At block 4319, processor 4007 may wait for user acceptance of the third bend plan before proceeding with operations of blocks 4131, 4135, 4139, and/or 4141. For example, processor 4007 may wait until user input is received (e.g., through a touch sensitive portion of display 118 or other user input device) to accept the third bend plan at block 4329. While not explicitly shown in FIG. 43, operations similar to those of FIG. 42 may allow the user to adjust one or more of the first, second, and/or third sets of transformation points that are used to generate the respective bend plans before accepting the third bend plan. The resulting accepted bend plan may then be used to proceed with operations of blocks 4131, 4135, 4139, and/or 4141, which may be performed as discussed above with respect to FIG. 41.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, operations, components, functions or groups but do not preclude the presence or addition of one or more other features, integers, elements, steps, operations, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit (also referred to as a processor) of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure to implement the functions/acts/operations specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A mechanical housing for a robotic rod bender, wherein the mechanical housing is configured to couple with a motor housing, the mechanical housing comprising:
    a rod feeding subassembly configured to feed a surgical rod in a longitudinal direction of the surgical rod;
    a brake subassembly configured to receive the rod from the rod feeding subassembly and to fix the surgical rod in place;
    a bending subassembly configured to bend the surgical rod while the surgical rod is fixed in place by the brake subassembly;
    a rod feeding transmission output configured to provide a first self-indexing output coupling with a rod feeding transmission input from the motor housing and to drive the rod feeding assembly responsive to torque coupled from the rod feeding transmission input;
    a brake transmission output configured to provide a second self-indexing output coupling with a brake transmission input from the motor housing and to drive the brake subassembly responsive to torque coupled form the brake transmission input; and
    a bending transmission output configured to provide a third self-indexing output coupling with a bending transmission input from the motor housing and to drive the bending subassembly responsive to torque coupled from the bending transmission input.

2. The mechanical housing of claim 1, wherein the rod feeding subassembly is a rod feeding/rotating subassembly configured to feed the surgical rod in the longitudinal direction of the surgical rod and/or to rotate the surgical rod about an axis of the surgical rod, wherein the rod feeding transmission output is a first rod feeding/rotating transmission output, and wherein the rod feeding transmission input is a first rod feeding/rotating transmission input, the mechanical housing further comprising:
    a second rod feeding/rotating transmission output configured to provide a fourth self-indexing output coupling with a second rod feeding/rotating transmission input from the motor housing, and wherein the first and second rod feeding/rotating transmission outputs are configured to drive the rod feeding/rotating assembly to feed and/or rotate the surgical rod responsive to torque coupled form the first and/or second rod feeding/rotating transmission inputs.

3. The mechanical housing of claim 1, wherein at least one of the first, second, and/or third self-indexing output couplings comprises a spline configured to engage with a corresponding spline of the motor housing.

4. The mechanical housing of claim 1, wherein at least one of the first, second, and/or third self-indexing output couplings comprises a slot configured to engage with a flat head of the motor housing, or wherein at least one of the first, second, and/or third self-indexing output couplings comprises a flat head drive configured to engage with a slot of the motor housing.

5. The mechanical housing of claim 1, wherein at least one of the first, second, and/or third self-indexing output couplings comprises a pin configured to engage with a slot of the motor housing, or wherein at least one of the first, second, and/or third self-indexing output couplings comprises a slot configured to engage with a pin of the motor housing.

6. The mechanical housing of claim 1, wherein at least one of the first, second, and/or third self-indexing output couplings comprises a spring controlled pin configured to engage with a slot of the motor housing.

7. The mechanical housing of claim 1, wherein at least one of the first, second, and/or third self-indexing output couplings comprises a central projection that is configured to engage with a corresponding central depression of the motor housing.

8. The mechanical housing of claim 1, wherein the mechanical housing includes first and second latches on opposite sides of the mechanical housing configured to detachably secure the mechanical housing in position relative to the motor housing.

9. The mechanical housing of claim 1 further comprising:
 a surface configured to couple with the motor housing, wherein the surface provides separation between the motor housing and each of the rod feeding, brake, and bending subassemblies, and wherein the rod feeding transmission output, the brake transmission output, and the rod feeding transmission output extend through the surface;
 a first rotary seal configured to provide a seal between the surface and the rod feeding transmission output;
 a second rotary seal configured to provide a seal between the surface and the brake transmission output; and
 a third rotary seal configured to provide a seal between the surface and the bending transmission output.

10. A motor housing for a robotic rod bender, wherein the motor housing is configured to couple with a mechanical housing, the motor assembly comprising:
 a rod feeding motor configured to drive a rod feeding subassembly of the mechanical housing;
 a brake motor configured to drive a brake subassembly of the mechanical housing;
 a bending motor configured to drive a bending subassembly of the mechanical housing;
 a rod feeding transmission input configured to provide a first self-indexing input coupling with a rod feeding transmission output from the mechanical housing and to couple torque from the rod feeding motor to the rod feeding transmission output;
 a brake transmission input configured to provide a second self-indexing input coupling with a brake transmission output from the mechanical housing and to couple torque from the brake motor to the brake transmission output; and
 a bending transmission input configured to provide a third self-indexing input coupling with a bending transmission output from the mechanical housing and to couple torque from the bending motor to the bending transmission output.

11. The motor housing of claim 10, wherein the rod feeding subassembly is a rod feeding/rotating subassembly, wherein the rod feeding motor is a first rod feeding/rotating motor, wherein the rod feeding transmission input is a first rod feeding/rotating transmission input, and wherein the rod feeding transmission output is a first rod feeding/rotating transmission output, the motor housing further comprising:
 a second rod feeding/rotating motor configured to drive the rod feeding/rotating subassembly of the mechanical housing; and
 a second rod feeding/rotating transmission input configured to provide a fourth self-indexing input coupling with a second rod feeding/rotating transmission output from the mechanical housing and to couple torque from the second rod feeding/rotating motor to the rod feeding/rotating subassembly.

12. The motor housing of claim 10, wherein at least one of the first, second, and/or third self-indexing input couplings comprises a spline configured to engage with a corresponding spline of the mechanical housing.

13. The motor housing of claim 10, wherein at least one of the first, second, and/or third self-indexing input couplings comprises a slot configured to engage with a flat head of the mechanical housing, or wherein at least one of the first, second, and/or third self-indexing input couplings comprises a flat head configured to engage with a slot of the mechanical housing.

14. The motor housing of claim 10, wherein at least one of the first, second, and/or third self-indexing input couplings comprises a pin configured to engage with a slot of the mechanical housing, or wherein at least one of the first, second, and/or third self-indexing input couplings comprises a slot configured to engage with a pin of the mechanical housing.

15. The motor housing of claim 10, wherein at least one of the first, second, and/or third self-indexing input couplings comprises a spring controlled pin configured to engage with a slot of the mechanical housing.

16. The motor housing of claim 10, wherein at least one of the first, second, and/or third self-indexing input couplings comprises a central projection that is configured to engage with a corresponding central depression of the mechanical housing.

17. The motor housing of claim 10 further comprising:
 an engagement assembly configured to receive the mechanical housing, wherein the engagement assembly is moveable relative to the rod feeding transmission input, the brake transmission input, and the bending transmission input so that after the mechanical housing is secured to the engagement assembly, the engagement assembly is configured to move to provide engagement between the rod feeding transmission input and the rod feeding transmission output through the first self-indexing input coupling, engagement between the brake transmission input and the brake transmission output through the second self-indexing input coupling, and engagement between the bending transmission input and the bending transmission output through the third self-indexing input coupling.

18. The motor housing of claim 10 further comprising:
 an engagement assembly configured to receive the mechanical housing, wherein the rod feeding transmission input, the brake transmission input, and the bending transmission input are moveable relative to the engagement assembly so that after the mechanical housing is secured to the engagement assembly, the rod feeding transmission input, the brake transmission input, and the bending transmission input are configured to move to provide engagement between the rod feeding transmission input and the rod feeding transmission output through the first self-indexing input coupling, engagement between the brake transmission input and the brake transmission output through the second self-indexing input coupling, and engagement between the bending transmission input and the bending transmission output through the third self-indexing input coupling.

19. A robotic rod bender comprising:
 a motor housing comprising, a first and second rod feeding/rotating motors,
a brake motor,
a bending motor,
a first rod feeding/rotating transmission input configured to couple torque from the first rod feeding/rotating motor through a first self-indexing input coupling,
a second rod feeding/rotating transmission input configured to couple torque from the first rod feeding/rotating motor through a first self-indexing input coupling,
a brake transmission input configured to couple torque from the brake motor through a third self-indexing input coupling, and
a bending transmission input configured to couple torque from the bending motor through a fourth self-indexing input coupling; and
a mechanical housing coupled with the motor housing, the mechanical housing comprising,
a rod feeding/rotating subassembly configured to feed a surgical rod in a longitudinal direction of the surgical rod and/or to rotate the surgical rod,
a brake subassembly configured to receive the rod from the rod feeding/rotating subassembly and to fix the surgical rod in place,
a bending subassembly configured to bend the surgical rod while the surgical rod is fixed in place by the brake subassembly,
a first rod feeding/rotating transmission output providing a first self-indexing output coupling with the first self-indexing input coupling from the motor housing and configured to drive the rod feeding/rotating assembly responsive to torque coupled from the first rod feeding/rotating motor,
a second rod feeding/rotating transmission output providing a second self-indexing output coupling with the second self-indexing input coupling from the motor housing and configured to drive the rod feeding/rotating assembly responsive to torque coupled from the second rod feeding/rotating motor,
a brake transmission output providing a third self-indexing output coupling with the third self-indexing input coupling from the motor housing and configured to drive the brake subassembly responsive to torque coupled form the braking motor, and
a bending transmission output providing a fourth self-indexing output coupling with the fourth self-indexing input coupling from the motor housing and configured to drive the bending subassembly responsive to torque coupled from the bending motor.

20. The robotic bender of claim 19 further comprising:
a drape on the motor housing and between the motor housing and the mechanical housing, wherein a seal is provided between the drape and the mechanical housing to isolate the motor housing.

* * * * *